US009486156B2

(12) United States Patent
Kato et al.

(10) Patent No.: US 9,486,156 B2
(45) Date of Patent: Nov. 8, 2016

(54) EYE FATIGUE DETERMINATION APPARATUS AND EYE FATIGUE DETERMINATION METHOD

(71) Applicant: Panasonic Corporation, Osaka (JP)

(72) Inventors: Yumiko Kato, Osaka (JP); Jun Ozawa, Nara (JP); Tsuyoshi Inoue, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 106 days.

(21) Appl. No.: 14/083,680

(22) Filed: Nov. 19, 2013

(65) Prior Publication Data

US 2014/0081117 A1 Mar. 20, 2014

Related U.S. Application Data

(63) Continuation of application No. PCT/JP2013/001356, filed on Mar. 5, 2013.

(30) Foreign Application Priority Data

Mar. 21, 2012 (JP) ................................ 2012-064350

(51) Int. Cl.
*A61B 5/0496* (2006.01)
*A61B 5/16* (2006.01)
(Continued)

(52) U.S. Cl.
CPC ............. *A61B 5/0496* (2013.01); *A61B 3/113* (2013.01); *A61B 5/04012* (2013.01); *A61B 5/053* (2013.01); *A61B 5/16* (2013.01); *A61B 5/6803* (2013.01); *A61B 5/7278* (2013.01)

(58) Field of Classification Search
CPC ... A61B 3/113; A61B 5/0496; A61B 5/0531
USPC ....................................................... 600/547
See application file for complete search history.

(56) References Cited

U.S. PATENT DOCUMENTS 5,127,708 A    7/1992    Kishi et al.
5,649,061 A *   7/1997    Smyth .................... A61B 3/113
                                                              250/221

(Continued)

FOREIGN PATENT DOCUMENTS

JP          3-47207          2/1991
JP          9-18894          1/1997

(Continued)

OTHER PUBLICATIONS

International Search Report issued May 14, 2013 in corresponding International Application No. PCT/JP2013/001356.

*Primary Examiner* — Adam J Eiseman
(74) *Attorney, Agent, or Firm* — Wenderoth, Lind & Ponack, L.L.P.

(57) ABSTRACT

An eye fatigue determination apparatus includes: an electrooculogram obtainment unit that obtains an electrooculogram indicating a potential measured using an electrode placed near an eye of a viewer who is viewing video content, the electrooculogram being measured in a plurality of predetermined time sections during display of the video content; an impedance obtainment unit that obtains an impedance between the electrode and the viewer's skin at a position where the electrode is placed, the impedance being measured in the plurality of predetermined time sections; an electrooculogram correction unit that corrects the electrooculogram measured in the plurality of predetermined time sections and obtained by the electrooculogram obtainment unit, based on the impedance measured in the plurality of predetermined time sections and obtained by the impedance obtainment unit; and a fatigue determination unit that determines fatigue of the viewer's eye, based on the electrooculogram corrected by the electrooculogram correction unit.

13 Claims, 37 Drawing Sheets

(51) Int. Cl.
*A61B 3/113* (2006.01)
*A61B 5/00* (2006.01)
*A61B 5/04* (2006.01)
*A61B 5/053* (2006.01)

(56) References Cited

U.S. PATENT DOCUMENTS

| | | | |
|---|---|---|---|
| 5,792,063 | A | 8/1998 | Danielsson et al. |
| 5,921,939 | A | 7/1999 | Danielsson et al. |
| 6,346,887 | B1 * | 2/2002 | Van Orden ............ G08B 21/06 |
| | | | 180/272 |
| 6,475,163 | B1 | 11/2002 | Smits et al. |
| 8,333,475 | B2 | 12/2012 | Sugio et al. |
| 8,449,116 | B2 | 5/2013 | Sato et al. |
| 8,741,003 | B2 * | 6/2014 | Inoue ................ G02B 27/0093 |
| | | | 359/462 |
| 9,268,145 | B2 * | 2/2016 | Kato ................ H04N 13/0438 |
| 9,285,599 | B2 * | 3/2016 | Imai ................... G02B 27/2264 |
| 2008/0188777 | A1 | 8/2008 | Bedziouk et al. |
| 2011/0170065 | A1 | 7/2011 | Sugio et al. |
| 2011/0178784 | A1 | 7/2011 | Sato et al. |
| 2012/0071743 | A1 * | 3/2012 | Todorov .............. G06F 19/3481 |
| | | | 600/372 |
| 2013/0044291 | A1 * | 2/2013 | Kato .................... A61B 3/0025 |
| | | | 351/209 |

FOREIGN PATENT DOCUMENTS

| | | |
|---|---|---|
| JP | 10-28680 | 2/1998 |
| JP | 10-99287 | 4/1998 |
| JP | 2001-231768 | 8/2001 |
| JP | 2006-305325 | 11/2006 |
| JP | 2011-120887 | 6/2011 |
| JP | 2011-125693 | 6/2011 |
| WO | 93/02616 | 2/1993 |

* cited by examiner

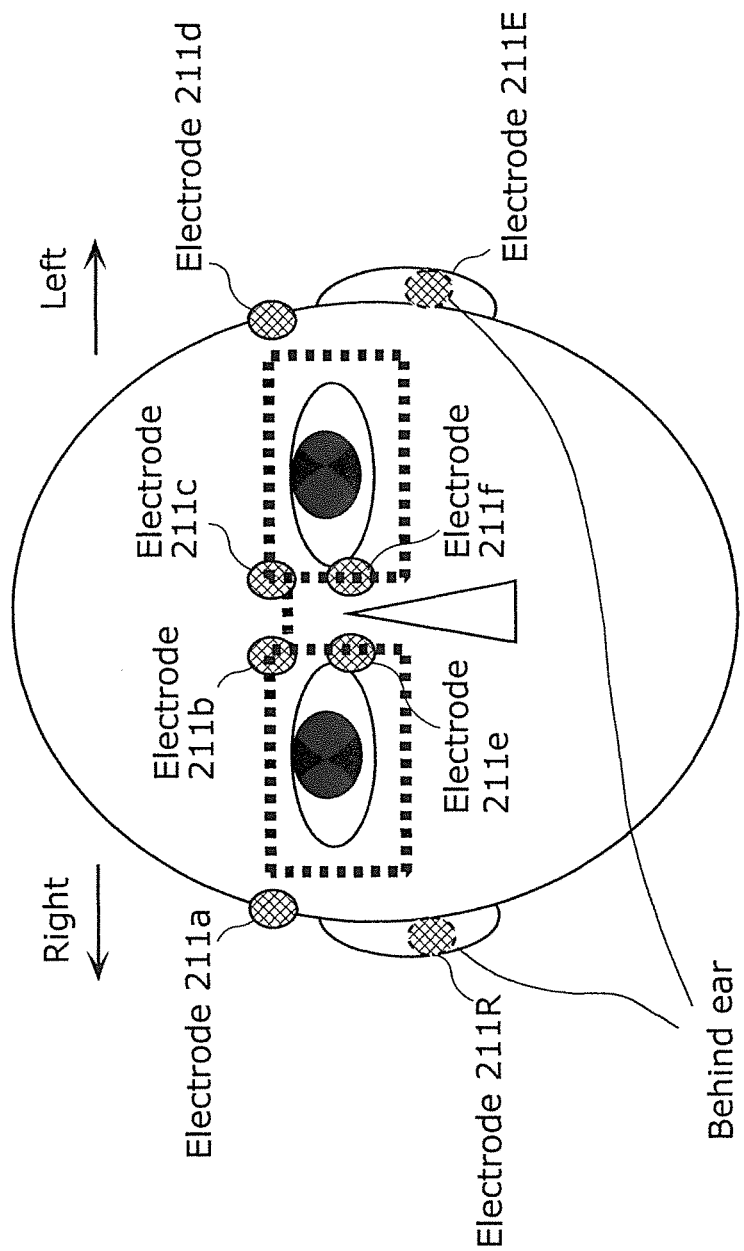

FIG. 7

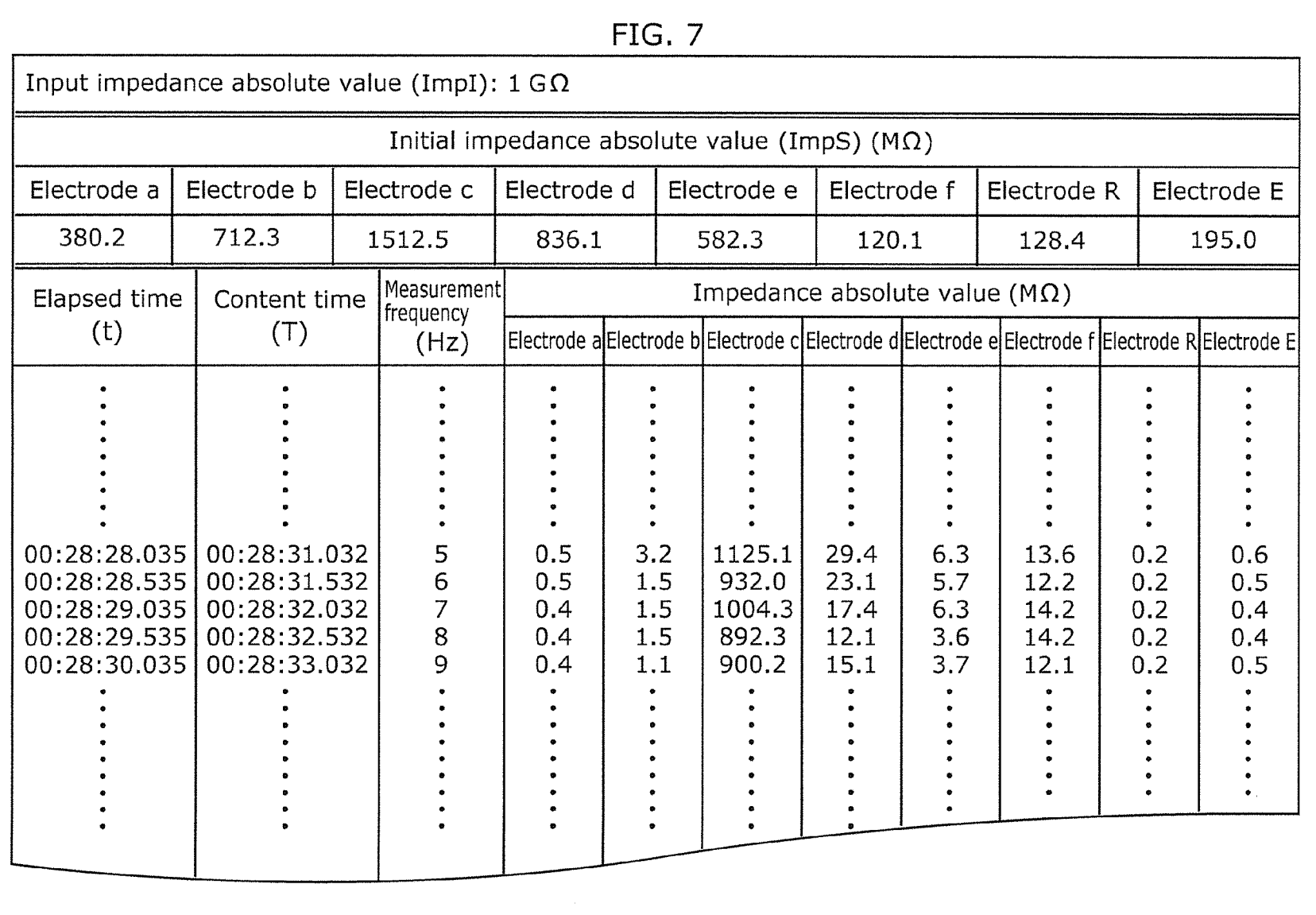

| Input impedance absolute value (ImpI): 1 GΩ | | | | | | | | | |
|---|---|---|---|---|---|---|---|---|---|
| Initial impedance absolute value (ImpS) (MΩ) | | | | | | | | | |
| Electrode a | Electrode b | Electrode c | Electrode d | Electrode e | Electrode f | Electrode R | Electrode E | | |
| 380.2 | 712.3 | 1512.5 | 836.1 | 582.3 | 120.1 | 128.4 | 195.0 | | |

| Elapsed time (t) | Content time (T) | Measurement frequency (Hz) | Impedance absolute value (MΩ) | | | | | | | |
|---|---|---|---|---|---|---|---|---|---|---|
| | | | Electrode a | Electrode b | Electrode c | Electrode d | Electrode e | Electrode f | Electrode R | Electrode E |
| ......... | ......... | ......... | ......... | ......... | ......... | ......... | ......... | ......... | ......... | ......... |
| 00:28:28.035 | 00:28:31.032 | 5 | 0.5 | 3.2 | 1125.1 | 29.4 | 6.3 | 13.6 | 0.2 | 0.6 |
| 00:28:28.535 | 00:28:31.532 | 6 | 0.5 | 1.5 | 932.0 | 23.1 | 5.7 | 12.2 | 0.2 | 0.5 |
| 00:28:29.035 | 00:28:32.032 | 7 | 0.4 | 1.5 | 1004.3 | 17.4 | 6.3 | 14.2 | 0.2 | 0.4 |
| 00:28:29.535 | 00:28:32.532 | 8 | 0.4 | 1.5 | 892.3 | 12.1 | 3.6 | 14.2 | 0.2 | 0.4 |
| 00:28:30.035 | 00:28:33.032 | 9 | 0.4 | 1.1 | 900.2 | 15.1 | 3.7 | 12.1 | 0.2 | 0.5 |
| ......... | ......... | ......... | ......... | ......... | ......... | ......... | ......... | ......... | ......... | ......... |

FIG. 8

| Amplitude of initial electrooculogram (EOGs) (μV) | | | |
|---|---|---|---|
| Electrode a - Electrode b | Electrode c - Electrode d | Electrode b - Electrode e | Electrode c - Electrode f |
| 84.6 | 72.1 | 23.6 | 38.1 |

| Elapsed time (t) | Content time (T) | Potential (μV) | | | | | |
|---|---|---|---|---|---|---|---|
| | | Electrode a | Electrode b | Electrode c | Electrode d | Electrode e | Electrode f |
| ......... | ......... | ......... | ......... | ......... | ......... | ......... | ......... |
| 00:47:06.167 | 01:06:31.032 | 2 | 1 | -1 | 5 | -3 | 5 |
| 00:47:06.177 | 01:06:31.042 | 1 | -2 | 3 | -1 | -2 | 3 |
| 00:47:06.187 | 01:06:31.052 | 18 | -13 | 12 | -21 | -10 | 8 |
| 00:47:06.197 | 01:06:31.062 | 80 | -25 | 19 | -75 | -17 | 13 |
| 00:47:06.207 | 01:06:31.072 | 89 | -40 | 39 | -88 | -32 | 27 |
| ......... | ......... | ......... | ......... | ......... | ......... | ......... | ......... |

FIG. 11

| Same direction duration (ms) | Speed: per frame (cm/frame interval) | Same direction movement logarithmic distance (log cm) | Electrooculogram measurement suitability |
|---|---|---|---|
| ..... | ..... | ..... | ..... |
| 1200≦1500⟩ | 9≦10⟩ | 2.51≦2.66⟩ | 5 |
| 900≦1200⟩ ← Data A | 9≦10⟩ | 2.39≦2.56⟩ | 4 |
| ..... | ..... | ..... | ..... |
| 300≦600⟩ | 2≦3⟩ | 1.26≦1.74⟩ | 2 |
| 0≦300⟩ | 2≦3⟩ | 0≦1.44⟩ | 1 |
| ..... | ..... | ..... | ..... |

FIG. 22A

Content C
Standard size : 62.3×110.7

Content B
Standard size : 300×555

Content A
Standard size : 300×705

| Time | Frame | Object ID | Standard three-dimensional coordinates (cm) |
|---|---|---|---|
| ... | ... | ... | ... |
| 00:28:31.032 | 102661 | 58 | (-283,130,-2000) |
|  |  | 60 | (338,-96,200) |
|  |  | 61 | (-86,-120,130) |
| 00:28:31.064 | 102662 | 58 | (-282,126,-1971) |
|  |  | 61 | (26,-98,170) |
| ... | ... | ... | ... |

FIG. 24

| Object speed (cm/frame) | Object depth position (Z axis cm) | Electrooculogram frequency (Hz) |
|---|---|---|
| ..... 4.5≦5〉<br>4≦4.5〉<br>3.5≦4〉 ..... | ..... 70≦80〉<br>70≦80〉<br>70≦80〉 ..... | ..... 7≦20〉<br>6≦20〉<br>5≦20〉 ..... |
| ..... 4.5≦5〉<br>4≦4.5〉<br>3.5≦4〉 ..... | ..... 30≦40〉<br>30≦40〉<br>30≦40〉 ..... | ..... 9≦25〉<br>8≦25〉<br>7≦25〉 ..... |

FIG. 33A

| | a | b | c | d | e | f | g | h | |
|---|---|---|---|---|---|---|---|---|---|
| Pattern 1 | Not good | Good | Good | Good | Good | Good | Not good | Good | Instruction 1 |
| Pattern 2 | Good | Not good | Not good | Good | Good | Good | Good | Good | Instruction 2 |
| Pattern 3 | Good | Good | Good | Good | Not good | Not good | Good | Good | Instruction 3 |
| ... | ... | ... | ... | ... | ... | ... | ... | ... | ... |

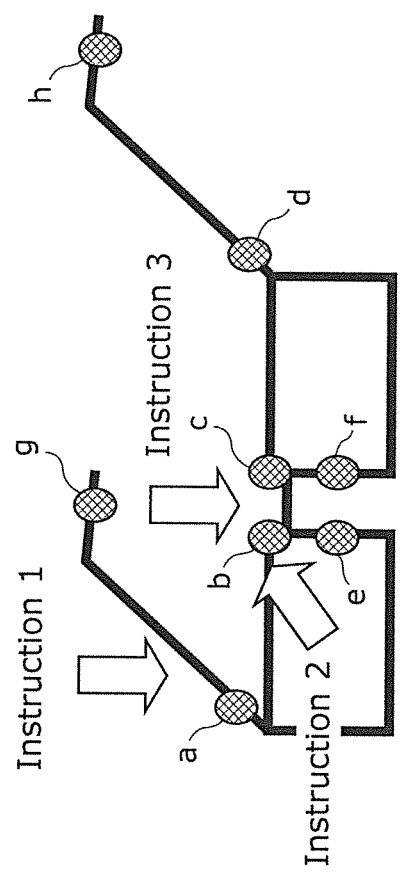

Example of instruction to viewer

EYE FATIGUE DETERMINATION APPARATUS AND EYE FATIGUE DETERMINATION METHOD

CROSS REFERENCE TO RELATED APPLICATIONS

This is a continuation application of PCT International Application No. PCT/JP2013/001356 filed on Mar. 5, 2013, designating the United States of America, which is based on and claims priority of Japanese Patent Application No. 2012-064350 filed on Mar. 21, 2012. The entire disclosures of the above-identified applications, including the specifications, drawings and claims are incorporated herein by reference in their entirety.

FIELD

One or more exemplary embodiments disclosed herein relate generally to an eye fatigue determination apparatus and eye fatigue determination method for determining a viewer's eye fatigue state when viewing stereoscopic video.

BACKGROUND

Patent Literature (PTL) 1 discloses a technique of determining a viewer's eye fatigue state based on his or her gaze point position, adjustment position, and gaze coordinate value of three-dimensional video.

PTL 2 discloses a wearable camera that measures an electrooculogram.

PTL 3 discloses a technique in which, with regard to a data change in impedance caused by electrode displacement, potential measurement in response to sound stimulation with the use of electrodes attached to the head or the neck is suspended at regular time intervals to measure an impedance and, in the case where the impedance is inappropriate, the frequency of impedance measurement is increased.

CITATION LIST

Patent Literature

[PTL 1]
Japanese Unexamined Patent Application Publication No. 2006-305325 (paragraph 0065)
[PTL 2]
Japanese Unexamined Patent Application Publication No. 2011-125693
[PTL 3]
Japanese Unexamined Patent Application Publication No. 2001-231768 (paragraphs 0006, 0008, 0009, 0016)

SUMMARY

Technical Problem

When viewing stereoscopic video, a viewer uses three-dimensional eyeglasses that switch between a right-eye shutter and a left-eye shutter synchronously with right-eye video and left-eye video displayed on a display. In the case where an electrode (or electrodes) for electrooculogram measurement is mounted on the three-dimensional eyeglasses, the impedance between the skin and the electrode changes due to sweating and the like in biopotential measurement.

The technique in PTL 3 is effective in enhancing a potential waveform relating to a specific event by signal averaging, but suffers a loss of data for a certain period in sequential potential waveform recording.

In particular, for about 30 minutes from when the electrode is placed, the electrical state between the skin and the electrode is unstable and the impedance tends to be high. After placing the electrode, the impedance decreases with time and eventually becomes stable. If the electrode temporarily comes off the skin or is displaced, however, the impedance fluctuates significantly.

In the case of measuring the electrooculogram using the electrode mounted on the three-dimensional eyeglasses and determining fatigue from the eye movement state, the electrooculogram measurement is suspended each time the impedance fluctuates as a result of the viewer adjusting the eyeglasses or the eyeglasses being displaced due to a change of the viewer's position. Thus, the conventional method has a problem that a situation where eye fatigue cannot be determined occurs frequently due to impedance fluctuations. Such a problem is not limited to the use of three-dimensional eyeglasses. For example, the same problem arises in the case of determining eye fatigue by measuring the electrooculogram with normal eyeglasses on which one or more electrodes are mounted.

One non-limiting and exemplary embodiment provides an eye fatigue determination apparatus and eye fatigue determination method that can accurately determine a viewer's eye fatigue state when viewing stereoscopic video even in the case of fluctuations in impedance between an electrode mounted on eyeglasses and the viewer's skin.

Solution to Problem

In one general aspect, the techniques disclosed here feature an eye fatigue determination apparatus including: an electrooculogram obtainment unit that obtains an electrooculogram indicating a potential measured using an electrode placed near an eye of a viewer who is viewing video content, the electrooculogram being measured in a plurality of predetermined time sections during display of the video content; an impedance obtainment unit that obtains an impedance between the electrode and the viewer's skin at a position where the electrode is placed, the impedance being measured in the plurality of predetermined time sections; an electrooculogram correction unit that corrects the electrooculogram obtained by the electrooculogram obtainment unit, based on the impedance obtained by the impedance obtainment unit; and a fatigue determination unit that determines fatigue of the viewer's eye, based on the electrooculogram corrected by the electrooculogram correction unit.

These general and specific aspects may be implemented using a system, a method, an integrated circuit, a computer program, or a computer-readable recording medium such as a CD-ROM, or any combination of systems, methods, integrated circuits, computer programs, or computer-readable recording media.

Additional benefits and advantages of the disclosed embodiments will be apparent from the Specification and Drawings. The benefits and/or advantages may be individually obtained by the various embodiments and features of the Specification and Drawings, which need not all be provided in order to obtain one or more of such benefits and/or advantages.

Advantageous Effects

One or more exemplary embodiments or features disclosed herein provide an eye fatigue determination apparatus and eye fatigue determination method that can accurately determine a viewer's eye fatigue state when viewing stereoscopic video even in the case of fluctuations in impedance between an electrode mounted on eyeglasses and the viewer's skin.

BRIEF DESCRIPTION OF DRAWINGS

These and other advantages and features will become apparent from the following description thereof taken in conjunction with the accompanying Drawings, by way of non-limiting examples of embodiments disclosed herein.

FIG. 4B is a schematic diagram showing positions at which the electrodes contact a viewer's face.

FIG. 7 is a diagram showing an example of a structure of data stored in a measured impedance storage unit in Embodiment 1.

FIG. 8 is a diagram showing an example of a structure of data stored in a measured electrooculogram storage unit in Embodiment 1.

FIG. 11 is a diagram showing an example of a structure of data stored in a movement determination table storage unit in Embodiment 1.

FIG. 22A is a diagram showing an example of a structure of data stored in a movement information storage unit in Embodiment 3.

FIG. 24 is a diagram showing an example of a structure of data stored in a speed-frequency conversion table storage unit in Embodiment 3.

FIG. 33A is a diagram showing an example of a structure of data stored in a defective electrode pattern storage unit in Variation 2 of Embodiment 1.

FIG. 33B is a schematic diagram showing an example of instructions for defect correction in Variation 2 of Embodiment 1.

DESCRIPTION OF EMBODIMENT(S)

Underlying Knowledge Forming Basis of the Present Disclosure

Figure 1:
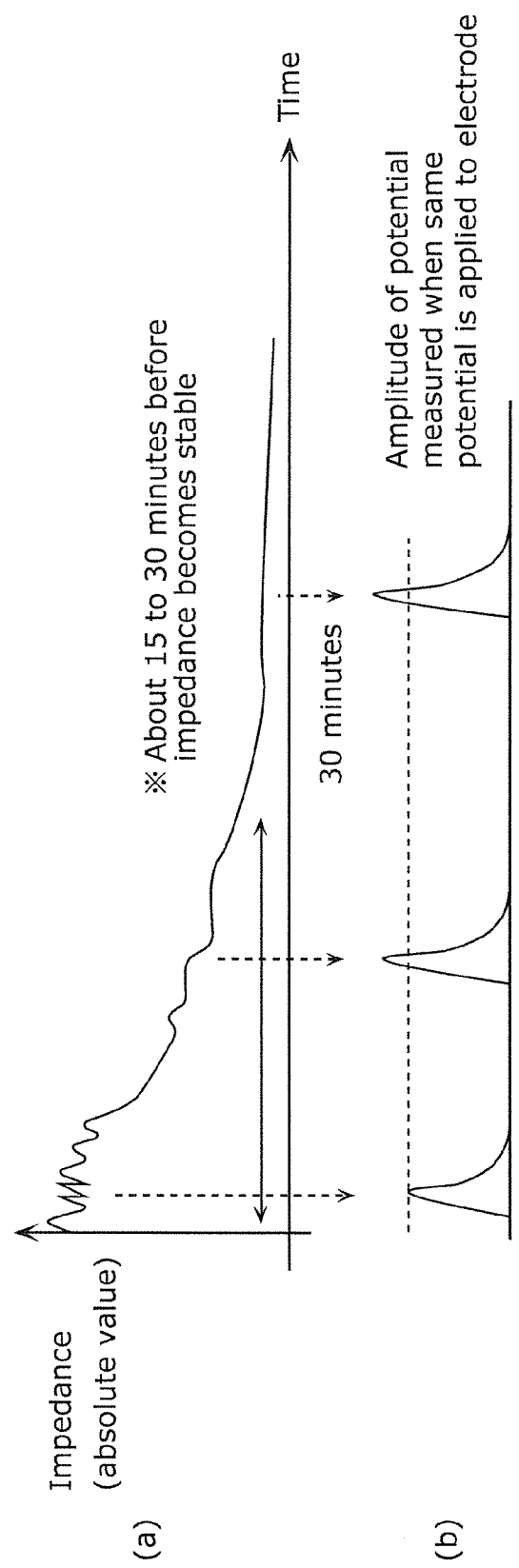
FIG. 1 is a schematic diagram showing time changes in contact impedance of an electrode and relationships between the contact impedance changing with time and the measured potential amplitude.
Figure 20:
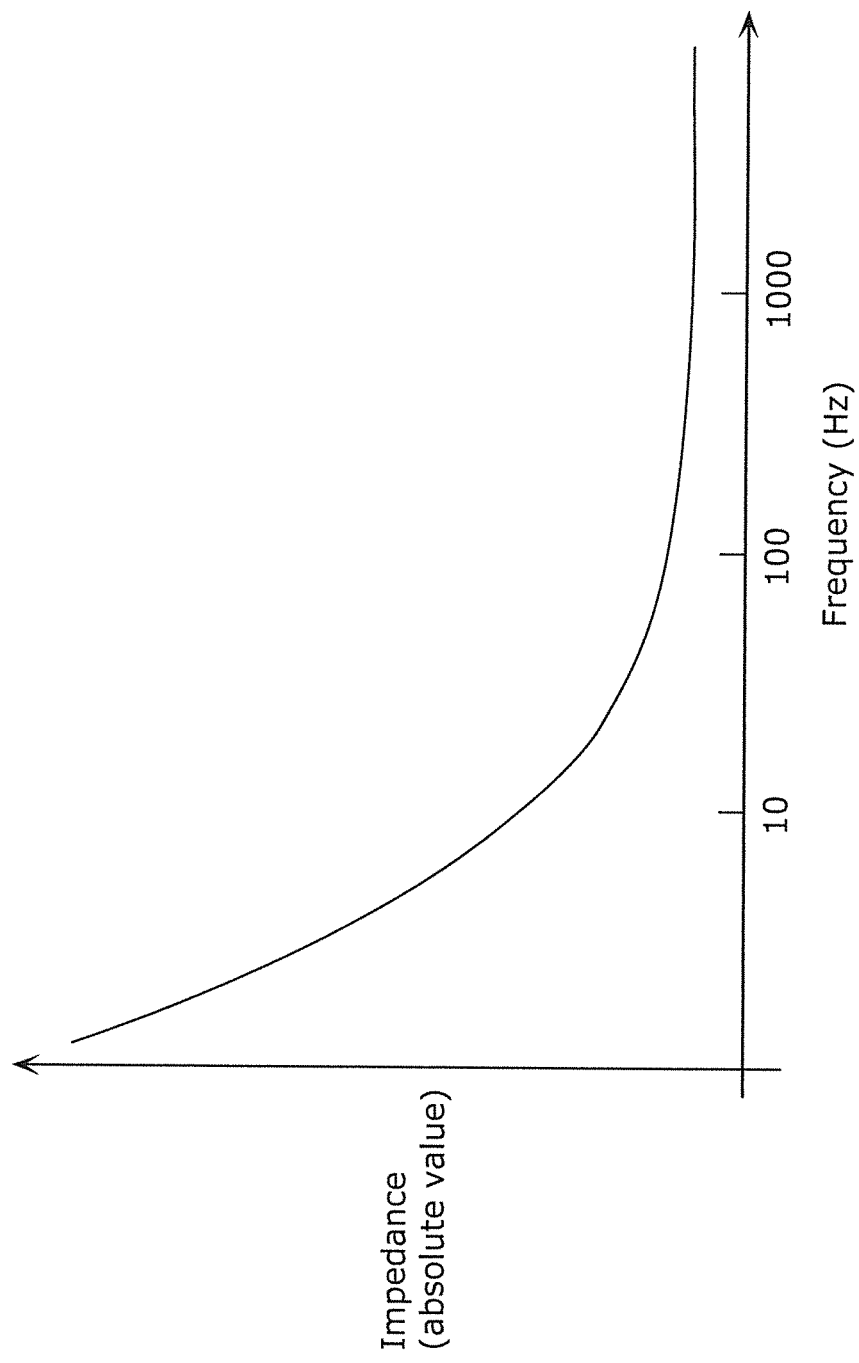
FIG. 20 is a schematic diagram showing relationships of how the contact impedance of an electrode changes depending on signal frequency.

Relationships between the contact impedance changing with time and the measured electrooculogram for about 30 minutes from when an electrode is placed are described below, before describing specific embodiments. FIG. 1 is a diagram schematically showing time changes in absolute value of the contact impedance and relationships between the absolute value of the contact impedance and the amplitude of the measured potential, in the case where an electrode for biopotential measurement is placed on the skin. (a) in FIG. 1 schematically shows the time changes in absolute value of the contact impedance. FIG. 20 in Non Patent Literature (NPL) 1 shows how the skin impedance changes with time after an electrode is placed on the skin.

[NPL 1]

Sunao Takeda, "The Technology on Electrode for Various Vital Potential", The Japanese journal of Medical Instrumentation 80(1), pp. 28-37, 2010

Immediately after the electrode is placed, the electrical resistance of the skin is high. The electrical resistance then decreases gradually, and becomes stable after 30 minutes. An example of attaching a gel electrode is shown in NPL 1. In the case where no gel is used, the absolute value of the impedance, i.e. the resistance, is higher and more unstable.

It is known that the potential measured from the electrode is inversely proportional to the contact impedance. (b) in FIG. 1 schematically shows potential measurement results when the same potential is applied to the electrode that changes in impedance. Even though the same potential is applied, the measured potential is low when the contact impedance is high, and high when the contact impedance is low.

In the case where the contact impedance changes, the amplitude of the measured potential is not steady, and it is very difficult to determine fatigue or the like from the amplitude of the potential.

In the present disclosure, the contact impedance of the electrode is measured, and the measured electrooculogram is corrected based on the absolute value of the measured impedance. This enables electrooculogram measurement and comparison to be also performed in a time section (hereafter "time section" is simply referred to as "section") in which the impedance is unstable, i.e. 30 minutes from when the electrode is placed, that is, from when the three-dimensional eyeglasses (hereafter also simply referred to as "eyeglasses") are put on to view stereoscopic video. As a result, ocular fatigue can be detected from the time change of the electrooculogram.

Particularly in the case of measuring the viewer's eye movement during video viewing using the electrooculogram, it is necessary to measure the eye movement when the viewer does not have eye fatigue. However, since the contact resistance between the electrode and the skin is unstable when the viewer puts on the eyeglasses, measuring the potential without taking the impedance into account only leads to inaccurate eye movement measurement. When measuring the electrooculogram in a laboratory or the like, the measurement is started only after the contact resistance between the electrode and the skin becomes sufficiently stable as a result of sweating or the like following the placement of the electrode. When viewing stereoscopic video for consumer use, however, it is very inconvenient if the viewer is not allowed to view video until the contact resistance becomes stable after the placement of the electrode.

In view of this, in the present disclosure, in the case of measuring the electrooculogram using the electrode mounted on the three-dimensional eyeglasses, not only the electrooculogram but also the impedance between the electrode and the skin is measured immediately after putting on the eyeglasses. This makes it possible to accurately measure the eye movement in an early stage of viewing during which the viewer does not have eye fatigue.

According to an exemplary embodiment disclosed herein, an eye fatigue determination apparatus includes: an electrooculogram obtainment unit that obtains an electrooculogram indicating a potential measured using an electrode placed near an eye of a viewer who is viewing video content, the electrooculogram being measured in a plurality of predetermined time sections during display of the video content; an impedance obtainment unit that obtains an impedance between the electrode and the viewer's skin at a position where the electrode is placed, the impedance being measured in the plurality of predetermined time sections; an electrooculogram correction unit that corrects the electrooculogram obtained by the electrooculogram obtainment unit, based on the impedance obtained by the impedance obtainment unit; and a fatigue determination unit that determines fatigue of the viewer's eye, based on the electrooculogram corrected by the electrooculogram correction unit.

Figure 2:
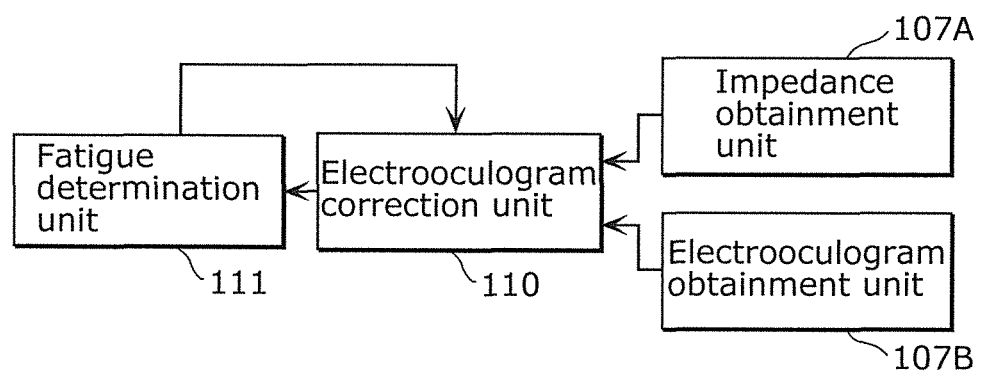
FIG. 2 is a diagram showing a structure of an eye fatigue determination apparatus according to one exemplary embodiment.

FIG. 2 is a diagram showing a structure of such an eye fatigue determination apparatus. The eye fatigue determination apparatus includes an impedance obtainment unit 107A, an electrooculogram obtainment unit 107B, an electrooculogram correction unit 110, and a fatigue determination unit 111. The detailed operations of the structural elements are as described above.

With this structure, the electrooculogram is corrected using the impedance. Therefore, even in the case where the impedance between the electrode near the viewer's eye and the viewer's skin fluctuates, the electrooculogram can be measured accurately. In particular, the electrooculogram can be measured accurately even in a time section in which the impedance is unstable, i.e. immediately after the viewer puts on the eyeglasses. As a result, the eye fatigue state can be determined accurately.

For example, the electrooculogram correction unit may correct the electrooculogram obtained by the electrooculogram obtainment unit, by multiplying the electrooculogram obtained by the electrooculogram obtainment unit by a ratio of an input impedance of the electrode to the impedance obtained by the impedance obtainment unit.

For example, the plurality of predetermined time sections may include a first time section and a second time section that are different from each other, wherein the electrooculogram obtainment unit obtains the electrooculogram measured in each of the first time section and the second time section, the impedance obtainment unit obtains the impedance measured in each of the first time section and the second time section, the electrooculogram correction unit corrects the electrooculogram measured in the first time section based on the impedance measured in the first time section, and corrects the electrooculogram measured in the second time section based on the impedance measured in the second time section, and the fatigue determination unit determines the fatigue of the viewer's eye, by comparing the electrooculogram measured in the first time section and corrected by the electrooculogram correction unit and the electrooculogram measured in the second time section and corrected by the electrooculogram correction unit.

For example, each of the plurality of predetermined time sections may be at least longer than a time length of one period of a periodic electrical signal used when the impedance obtainment unit obtains the impedance.

For example, the second time section may start at least 10 minutes after the first time section starts.

For example, the eye fatigue determination apparatus may further include: a video content obtainment unit that obtains the video content; and a measurement schedule determination unit that, from the video content obtained by the video content obtainment unit, determines an electrooculogram measurement time section in each of the first time section and the second time section, and determines an impedance measurement time section in each of the first time section and the second time section based on the determined electrooculogram measurement time section, the electrooculogram measurement time section being a time section for measuring the electrooculogram, and the impedance measurement time section being a time section for measuring the impedance, wherein the electrooculogram obtainment unit obtains the electrooculogram measured in the electrooculogram measurement time section determined by the measurement schedule determination unit, and the impedance obtainment unit obtains the impedance measured in the impedance measurement time section determined by the measurement schedule determination unit.

For example, the measurement schedule determination unit may determine the first time section and the second time section according to a movement amount of an object in the video content, the movement amount of the object in the video content included in the first time section and the movement amount of the object in the video content included in the second time section being equal to each other.

For example, the measurement schedule determination unit may, in the case where the video content is stereoscopic video content, determine the first time section and the second time section according to the movement amount of the object in the video content in a depth direction, the movement amount of the object in the video content in the depth direction included in the first time section and the movement amount of the object in the video content in the depth direction included in the second time section being equal to each other.

For example, the measurement schedule determination unit may, in the case where the video content is stereoscopic video content, determine the first time section and the second time section according to a distance of an object in the video content in a depth direction, a range of the distance of the object in the video content in the depth direction included in the first time section and a range of the distance of the object in the video content in the depth direction included in the second time section being equal to each other.

For example, the measurement schedule determination unit may determine the electrooculogram measurement time section to be longer in the case where a movement duration of an object in the video content in a depth direction is longer and a movement speed of the object in the depth direction is higher.

The eye moves more when the movement speed of the object in the depth direction is higher. Hence, the time section in which the eye moves more can be set as the electrooculogram measurement time section. This enables early determination of eye fatigue.

For example, the measurement schedule determination unit may determine the electrooculogram measurement time section to be longer in the case where a reproduction speed of the video content obtained by the video content obtainment unit is higher.

In the case where the content is reproduced at double speed, the movement speed of the object in the depth direction is higher than in the case of normal reproduction. That is, the eye moves more when the reproduction speed is higher. Hence, the time section in which the eye moves more can be set as the electrooculogram measurement time section. This enables early determination of eye fatigue.

For example, the eye fatigue determination apparatus may further include: an impedance measurement unit that measures the impedance between the electrode near the viewer's eye and the viewer's skin at the position where the electrode is placed; a frequency analysis unit that analyzes a frequency of the electrooculogram of the viewer obtained by the electrooculogram obtainment unit; and a measurement frequency determination unit that determines a frequency of a signal used for impedance measurement by the impedance measurement unit, based on the frequency of the electrooculogram of the viewer analyzed by the frequency analysis unit, wherein the impedance measurement unit measures the impedance using the signal of the frequency determined by the measurement frequency determination unit, and the impedance obtainment unit obtains the impedance measured by the impedance measurement unit.

By determining the frequency used for impedance measurement according to the frequency of the obtained electrooculogram in this way, the impedance for correcting the electrooculogram used in fatigue determination can be measured at the frequency of the electrooculogram which is the signal to be measured. This reduces the electrooculogram correction error caused by the difference in impedance depending on frequency. As a result, eye fatigue can be determined more accurately.

For example, the eye fatigue determination apparatus may further include: an impedance measurement unit that measures the impedance between the electrode near the viewer's eye and the viewer's skin at the position where the electrode is placed; and a movement information extraction unit that extracts movement information of an object in the video content obtained by the video content obtainment unit, wherein the measurement schedule determination unit includes: a frequency estimation unit that estimates a frequency of the electrooculogram of the viewer, from the movement information of the object extracted by the movement information extraction unit; and a frequency range determination unit that determines a frequency range of a signal used for impedance measurement by the impedance measurement unit, based on the frequency of the electrooculogram of the viewer estimated by the frequency estimation unit, the impedance measurement unit measures the impedance using the signal of a frequency included in the frequency range determined by the frequency range determination unit, and the impedance obtainment unit obtains the impedance measured by the impedance measurement unit.

By determining the frequency range used for impedance measurement according to the frequency of the electrooculogram estimated from the movement of the object in the video content, the impedance for correcting the electrooculogram used in fatigue determination can be measured at the frequency of the electrooculogram which is the signal to be measured. This reduces the electrooculogram correction error caused by the difference in impedance depending on frequency. As a result, eye fatigue can be determined more accurately.

For example, the eye fatigue determination apparatus may further include: an electrooculogram measurement unit that measures the electrooculogram of the viewer using the electrode near the viewer's eye; an impedance measurement unit that measures the impedance between the electrode near the viewer's eye and the viewer's skin at the position where the electrode is placed; a frequency analysis unit that analyzes a frequency of the electrooculogram of the viewer obtained by the electrooculogram obtainment unit; and a movement information extraction unit that extracts movement information of an object in the video content obtained by the video content obtainment unit, wherein the measurement schedule determination unit includes: a frequency estimation unit that estimates the frequency of the electrooculogram of the viewer, from the movement information of the object extracted by the movement information extraction unit; a frequency range determination unit that determines a frequency range of a signal used for impedance measurement by the impedance measurement unit, based on the frequency of the electrooculogram of the viewer estimated by the frequency estimation unit; and a determination unit that changes the electrooculogram measurement time section, according to a degree of agreement between the frequency range of the signal used for impedance measurement determined by the frequency range determination unit and the frequency of the electrooculogram estimated by the frequency estimation unit, the electrooculogram measurement unit measures the electrooculogram of the viewer in the electrooculogram measurement time section changed by the determination unit, the impedance measurement unit measures the impedance using the signal of a frequency included in the frequency range determined by the frequency range determination unit, the electrooculogram obtainment unit obtains the electrooculogram of the viewer measured by the electrooculogram measurement unit, and the impedance obtainment unit obtains the impedance measured by the impedance measurement unit.

By determining the frequency range used for impedance measurement according to the frequency of the electrooculogram estimated from the movement of the object in the video content, the impedance for correcting the electrooculogram used in fatigue determination can be measured at the frequency of the electrooculogram which is the signal to be measured. This reduces the electrooculogram correction error caused by the difference in impedance depending on frequency. As a result, eye fatigue can be determined more accurately.

Moreover, the electrooculogram measurement time section can be set appropriately, even in the case where the frequency obtained from the actually measured electrooculogram is different from the estimated frequency range.

For example, the determination unit may extend the electrooculogram measurement time section, in the case where the frequency of the electrooculogram analyzed by the frequency analysis unit is higher than the frequency range of the signal used for impedance measurement determined by the frequency range determination unit.

In such a case, the eye actually moves more than expected. Accordingly, eye fatigue can be determined appropriately by extending the electrooculogram measurement time section.

For example, the determination unit may reduce the electrooculogram measurement time section, in the case where the frequency of the electrooculogram analyzed by the frequency analysis unit is lower than the frequency range of the signal used for impedance measurement determined by the frequency range determination unit.

In such a case, the eye actually moves less than expected, and so there is less need to measure the electrooculogram than expected. Accordingly, eye fatigue can be determined appropriately by reducing the electrooculogram measurement time section.

For example, the measurement schedule determination unit may further include a depth movement distance calculation unit that calculates a movement distance of the object in a depth direction, from the movement information of the object extracted by the movement information extraction unit, wherein the frequency estimation unit estimates the frequency of the electrooculogram of the viewer to be higher in the case where the movement distance of the object in the depth direction between adjacent frames calculated by the depth movement distance calculation unit is longer.

This is because, when the movement distance of the object in the depth direction is longer, the eye moves more and so the frequency of the electrooculogram is higher.

For example, the electrooculogram correction unit may correct the electrooculogram, without using the impedance measured in a time section in which a change in impedance per unit time is greater than or equal to a predetermined value.

The impedance becomes unstable when, for example, the electrode is pressed. With this structure, such a time section in which the impedance is unstable is excluded when correcting the electrooculogram. Thus, the electrooculogram can be measured more accurately.

For example, the video content may be stereoscopic video content, wherein the electrode near the viewer's eye is included in a stereoscopic video viewing device worn by the viewer, and the eye fatigue determination apparatus further includes: a defective electrode pattern obtainment unit that obtains defective electrode pattern information indicating correspondence between a contact state of the electrode near the viewer's eye and instruction information for a position of the viewing device worn by the viewer; an electrode contact state determination unit that determines the contact state of the electrode near the viewer's eye, based on the impedance obtained by the impedance obtainment unit; and an adjustment instruction information generation unit that generates instruction information by obtaining, from the defective electrode pattern information obtained by the defective electrode pattern obtainment unit, the instruction information corresponding to the contact state of the electrode determined by the electrode contact state determination unit, and presents the instruction information to the viewer.

Since the contact state of the electrode can be determined from the impedance, the instruction information for correcting the displacement of the viewing device can be displayed for the viewer based on the impedance. Examples of the viewing device include eyeglasses and a head-mounted display.

For example, the eye fatigue determination apparatus may further include a screen control unit that displays a message according to the fatigue determined by the fatigue determination unit, on a screen.

With this structure, when the viewer has eye fatigue, the viewer can be prompted to stop viewing the stereoscopic video content.

For example, the eye fatigue determination apparatus may further include a screen control unit that controls the depth of the video content displayed on the screen according to the fatigue determined by the fatigue determination unit.

With this structure, when the viewer has eye fatigue, the eye fatigue can be alleviated by reducing the depth of the video content or changing the video content to two-dimensional video.

For example, the first time section may be a time section in which the viewer starts viewing the video content.

With this structure, the eye fatigue state can be determined from the change from the electrooculogram at the start of viewing the video content. The eye fatigue state can thus be measured more accurately.

These general and specific aspects may be implemented using a system, a method, an integrated circuit, a computer program, or a computer-readable recording medium such as a CD-ROM, or any combination of systems, methods, integrated circuits, computer programs, or computer-readable recording media.

Hereinafter, certain exemplary embodiments are described in greater detail with reference to the accompanying Drawings.

Each of the exemplary embodiments described below shows a general or specific example. The numerical values, shapes, materials, structural elements, the arrangement and connection of the structural elements, steps, the processing order of the steps etc. shown in the following exemplary embodiments are mere examples, and therefore do not limit the scope of the appended Claims and their equivalents. Therefore, among the structural elements in the following exemplary embodiments, structural elements not recited in any one of the independent claims are described as arbitrary structural elements.

Embodiment 1

Figure 3:
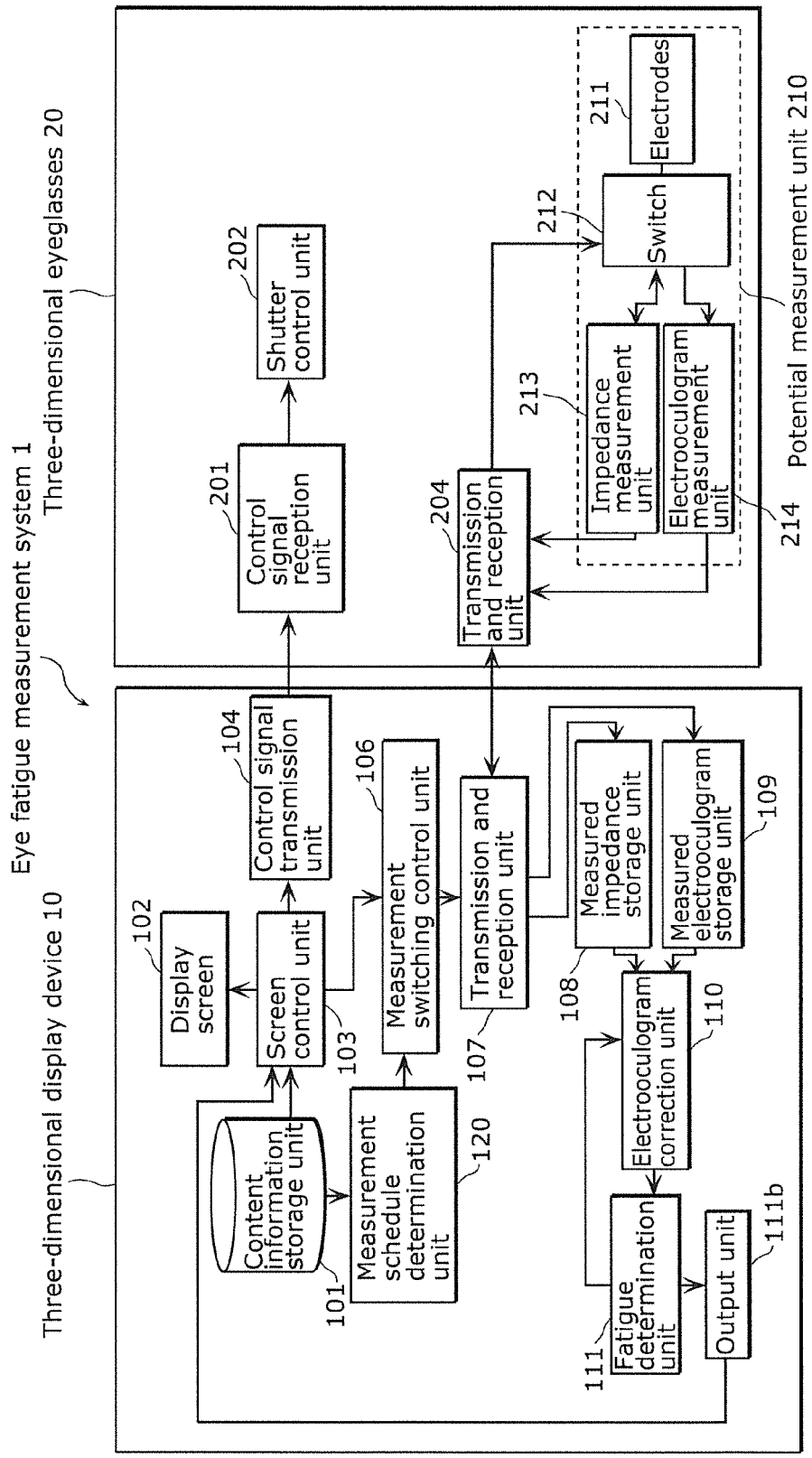
FIG. 3 is a block diagram showing an example of a structure of an eye fatigue measurement system in Embodiment 1.

FIG. 3 is a diagram showing a structure of an eye fatigue measurement system 1 of a stereoscopic video display system in Embodiment 1.

The eye fatigue measurement system 1 includes a three-dimensional display device 10 and three-dimensional eyeglasses 20.

(Three-Dimensional Eyeglasses)

The three-dimensional eyeglasses 20 are an example of a viewing device, and include a control signal reception unit 201, a shutter control unit 202, a potential measurement unit 210, and a transmission and reception unit 204.

The control signal reception unit 201 receives a control signal for synchronizing the screen display and the three-dimensional eyeglasses, from the three-dimensional display device 10.

The shutter control unit 202 opens and closes a right-eye shutter or a left-eye shutter (not shown), synchronously with a right-eye image or a left-eye image displayed on a screen.

The potential measurement unit 210 measures biopotential information of a viewer.

The transmission and reception unit 204 performs information communication with the three-dimensional display device 10.

The potential measurement unit 210 includes a plurality of electrodes 211, a switch 212, an impedance measurement unit 213, and an electrooculogram measurement unit 214.

The electrodes 211 contact parts around the viewer's eyes, and obtain the viewer's electrooculogram.

Figure 4A:
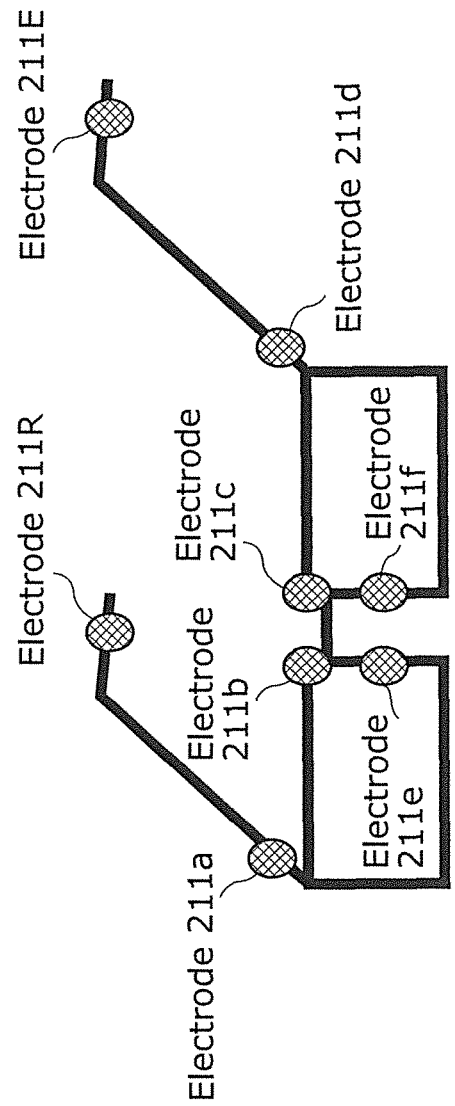
FIG. 4A is a schematic diagram showing an example of positions of electrodes on three-dimensional eyeglasses in the eye fatigue measurement system in Embodiment 1.

FIG. 4A is a diagram showing an example of the three-dimensional eyeglasses 20 including the electrodes in this embodiment.

FIG. 4B is a diagram showing points at which the electrodes 211 contact the viewer's skin when the viewer wears the three-dimensional eyeglasses 20 shown in FIG. 4A.

The measurement electrodes in this embodiment include eight electrodes in total: six electrodes 211a to 211f; a reference electrode 211R; and a body earth electrode 211E. Note that the number of electrodes is not limited to such. Hereafter, the electrodes 211a to 211f, the reference electrode 211R, and the body earth electrode 211E are also referred to as "electrodes a to f", "electrode R", and "electrode E", respectively.

The electrodes 211a and 211b are arranged at positions corresponding to both sides of the viewer's right eye in the horizontal direction, and measure the electrooculogram associated with the horizontal eye movement of the viewer's right eye.

The electrodes 211c and 211d are arranged at positions corresponding to both sides of the viewer's left eye in the horizontal direction, and measure the electrooculogram associated with the horizontal eye movement of the viewer's left eye.

The electrodes 211b and 211e are arranged at positions corresponding to both sides of the viewer's right eye in the vertical direction, and measure the electrooculogram associated with the vertical eye movement of the viewer's right eye.

The electrodes 211c and 211f are arranged at positions corresponding to both sides of the viewer's left eye in the vertical direction, and measure the electrooculogram associated with the vertical eye movement of the viewer's left eye.

The impedance measurement unit 213 measures the contact impedance of the electrodes.

Figure 5:
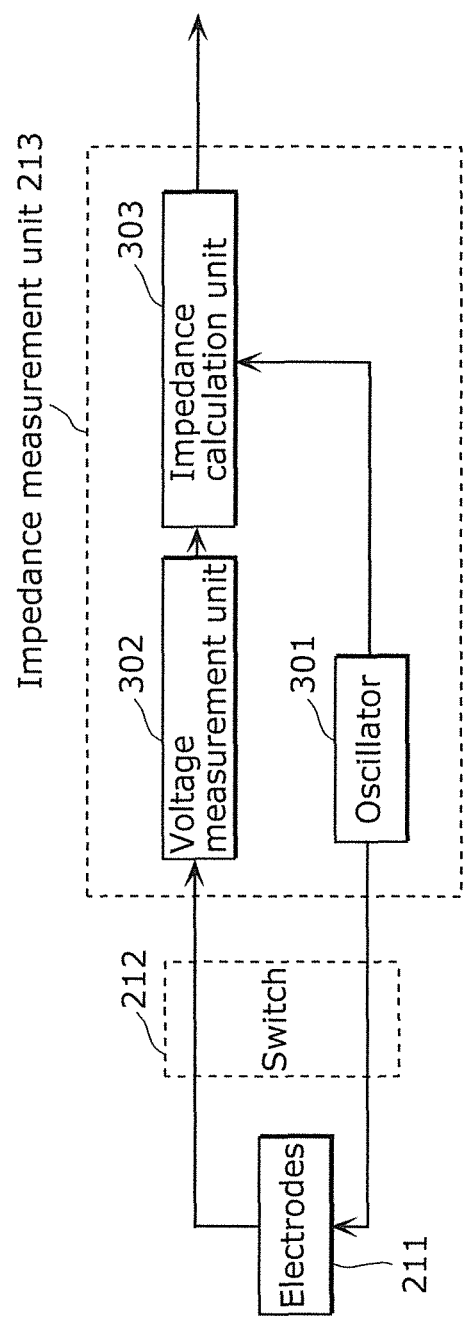
FIG. 5 is a diagram showing a detailed structure of an impedance measurement unit in Embodiment 1.

FIG. 5 is a diagram showing an example of a detailed structure of the impedance measurement unit 213. The impedance measurement unit 213 includes an oscillator 301, a voltage measurement unit 302, and an impedance calculation unit 303. The oscillator 301 generates a current for impedance measurement. The voltage measurement unit 302 measures a voltage when the current output from the oscillator 301 flows through two electrodes 211 and the living body. The impedance calculation unit 303 calculates an impedance of a circuit formed by the two electrodes 211 and the living body, from the output of the oscillator 301 and the output of the voltage measurement unit 302.

The electrooculogram measurement unit 214 measures the electrooculogram.

The switch 212 switches between impedance measurement and electrooculogram measurement.

The transmission and reception unit 204 transmits impedance measurement information or electrooculogram measurement information.

Note that the viewing device worn by the viewer is not limited to the three-dimensional eyeglasses 20. That is, the eye fatigue measurement system 1 in this embodiment is not limited to measuring eye fatigue when viewing stereoscopic video, and may measure eye fatigue when viewing two-dimensional video. In this case, the viewer wears a device such as eyeglasses that include the potential measurement unit 210 and the transmission and reception unit 204 without the control signal reception unit 201 and the shutter control unit 202, instead of the three-dimensional eyeglasses 20. For example, the viewer may wear display eyeglasses that include the control signal reception unit 201 and the shutter control unit 202, for measurement of his or her eye fatigue. The display eyeglasses are, for instance, eyeglasses that block light of a specific wavelength such as blue light.

(Three-Dimensional Display Device)

The three-dimensional display device 10 shown in FIG. 3 includes a content information storage unit 101, a display screen 102, a screen control unit 103, a control signal transmission unit 104, a measurement schedule determination unit 120, a measurement switching control unit 106, a transmission and reception unit 107, a measured impedance storage unit 108, a measured electrooculogram storage unit 109, an electrooculogram correction unit 110, a fatigue determination unit 111, and an output unit 111b.

The content information storage unit 101 stores video content (hereafter also referred to as "content") including stereoscopic video.

Figure 6:
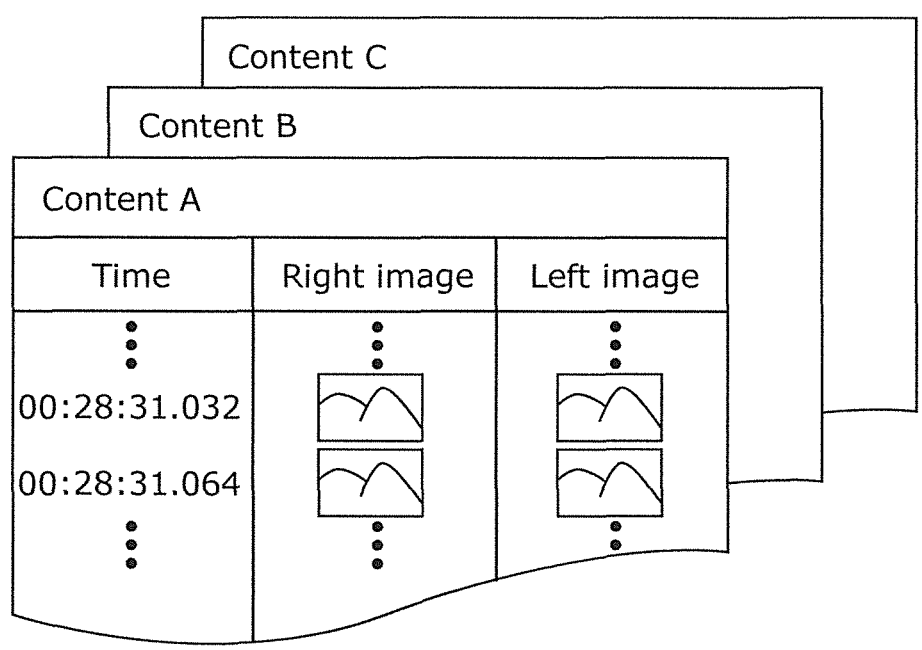
FIG. 6 is a diagram showing an example of a structure of data stored in a content information storage unit in Embodiment 1.

FIG. 6 is a diagram showing an example of information stored in the content information storage unit 101. For example, the content information storage unit 101 stores data for each content item, and the data for each content item includes: content identification information; each time from content start; and a right-eye image and a left-eye image at each time.

The screen control unit 103 performs control so that video content in the content information storage unit 101 is displayed on the display screen 102, and also generates a command signal for controlling synchronization between the display screen 102 and the three-dimensional eyeglasses 20.

The display screen 102 displays the video content.

The control signal transmission unit 104 transmits a control signal for synchronizing the screen display and the three-dimensional eyeglasses 20 to the three-dimensional eyeglasses 20, based on the command signal generated by the screen control unit 103.

The measurement schedule determination unit 120 determines, prior to image display, a schedule of whether the electrooculogram or the electrode contact impedance is measured with regard to the time information of the video content, based on the time information and the left-eye image and right-eye image of the video content stored in the content information storage unit 101.

The measurement switching control unit 106 controls switching between electrooculogram measurement and contact impedance measurement, according to the schedule determined by the measurement schedule determination unit 120.

The transmission and reception unit 107 performs information communication with the three-dimensional eyeglasses 20. The transmission and reception unit 107 receives impedance measurement information and electrooculogram measurement information from the three-dimensional eyeglasses 20. Note that the transmission and reception unit 107 functions as the impedance obtainment unit 107A and the electrooculogram obtainment unit 107B shown in FIG. 2. The impedance measurement information is, for example, the absolute value of the impedance of each electrode at each measurement time. The electrooculogram measurement information is, for example, the difference in potential between each of the electrodes 211a to 211f and the reference electrode 211R at each measurement time.

The measured impedance storage unit 108 stores the impedance measurement information received from the three-dimensional eyeglasses 20.

FIG. 7 is a diagram showing an example of information stored in the measured impedance storage unit 108. For example, the measured impedance storage unit 108 stores an absolute value of an input impedance of the electrooculogram measurement unit 214, and also stores an elapsed time, a content time, a measurement frequency, and an absolute value of an impedance of each of the electrodes a to f, the electrode R, and the electrode E. The measured impedance storage unit 108 further stores a time-averaged impedance of each electrode measured before and after an electrooculogram measurement section closest to the video display start time, as an initial impedance absolute value. Alternatively, the impedance measurement section may be either before or after the electrooculogram measurement section.

The elapsed time indicates a time elapsed from when the viewer starts viewing the stereoscopic video with the three-dimensional display device 10 and the three-dimensional eyeglasses 20. The content time indicates time information of the content stored in the content information storage unit 101, i.e. a time from the content start. The measurement frequency indicates a frequency of a current used for impedance measurement.

The measured electrooculogram storage unit 109 stores the electrooculogram measurement information received from the three-dimensional eyeglasses 20.

FIG. 8 is a diagram showing an example of information stored in the measured electrooculogram storage unit 109. For example, the measured electrooculogram storage unit 109 stores an elapsed time, a content time, and a potential difference between each of the electrodes a to f and the electrode R. The measured electrooculogram storage unit 109 further stores an amplitude of an initial electrooculogram obtained from the potential of each electrode measured in the electrooculogram measurement section closest to the video display start time. The amplitude of the initial electrooculogram will be described later. The elapsed time and the content time in FIG. 8 are time information of the same definitions as in FIG. 7. Note, however, that the sampling frequency is different from that in impedance measurement, and so the elapsed time between the pieces of data and the time interval between the content times are different from those in FIG. 7. An example where the sampling frequency is 100 Hz is shown in this embodiment. In this case, the time interval is 10 ms.

The time information shown in FIG. 7 and the time information shown in FIG. 8 as examples do not overlap each other because impedance measurement and electrooculogram measurement are not performed simultaneously.

The electrooculogram correction unit 110 corrects the electrooculogram measurement information based on the impedance measurement information.

The fatigue determination unit 111 compares the electrooculograms measured at different times and corrected, to determine the viewer's eye fatigue state.

The output unit 111b outputs the eye fatigue state determined by the fatigue determination unit 111, to the screen control unit 103. The screen control unit 103 displays a message according to the eye fatigue state received from the output unit 111b, on the display screen 102. For example, when the viewer has eye fatigue, a message prompting the viewer to rest is displayed on the display screen 102. The screen control unit 103 may control the depth of the video content displayed on the display screen 102, according to the eye fatigue state. For example, when the viewer has eye fatigue, the eye fatigue can be alleviated by reducing the depth of the video content or changing the video content to two-dimensional video.

In this embodiment, the transmission and reception unit 107 and the transmission and reception unit 204 communicate wirelessly. The communication is bidirectional communication using RF (Radio Frequency) communication, Bluetooth® communication, ZigBee®, Wi-Fi® communication, infrared communication, or the like.

Though the above describes the case where the video content display device included in the eye fatigue measurement system 1 is the three-dimensional display device 10, the display device need not necessarily be for three-dimensional display, and may be a two-dimensional image display device. The two-dimensional image display device does not include the control signal transmission unit 104, and the content information storage unit 101 stores two-dimensional video content. The screen control unit 103 controls the display screen 102, without outputting a command signal for synchronization between the display screen 102 and the eyeglasses. The measurement schedule determination unit 120 determines a schedule of whether the electrooculogram or the electrode contact impedance is measured with regard to the time information of the video content, based on the time information and the image information of the video content stored in the content information storage unit 101.

(Measurement Schedule Determination Unit)

Figure 9:
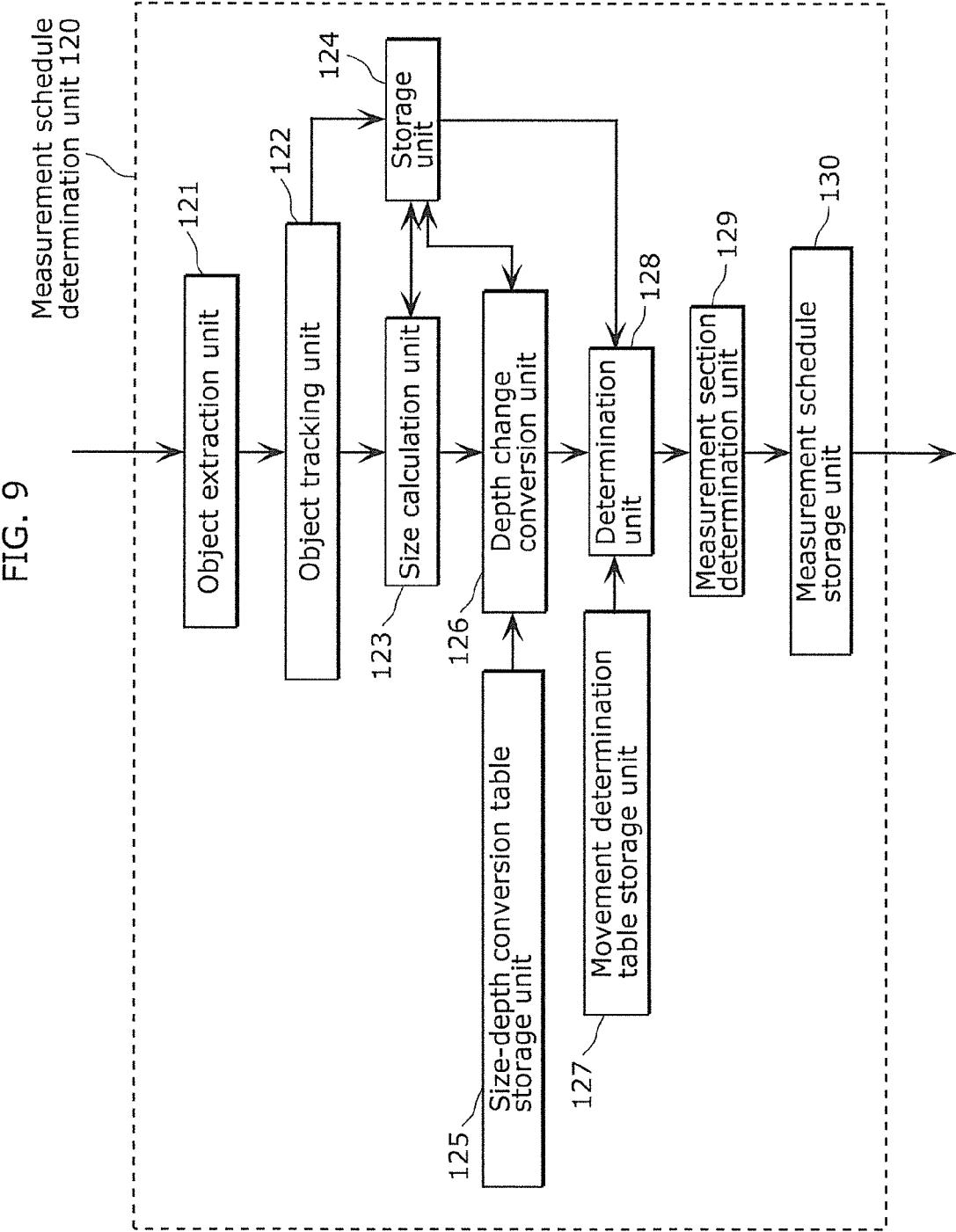
FIG. 9 is a diagram showing a detailed structure of a measurement schedule determination unit in Embodiment 1.

FIG. 9 is a diagram showing a structure of the measurement schedule determination unit 120.

The measurement schedule determination unit 120 includes an object extraction unit 121, an object tracking unit 122, a size calculation unit 123, a storage unit 124, a size-depth conversion table storage unit 125, a depth change conversion unit 126, a movement determination table storage unit 127, a determination unit 128, a measurement section determination unit 129, and a measurement schedule storage unit 130.

The object extraction unit 121 extracts an object in the right-eye image or the left-eye image, from the image information of each time of the video content stored in the content information storage unit 101.

The object tracking unit 122 tracks each object extracted by the object extraction unit 121, in the time direction.

The size calculation unit 123 analyzes, for each extracted object, a time change in area of the object with respect to the screen size.

The storage unit 124 stores time information and size information for each extracted object. The size information is a ratio to the screen size, the number of pixels, or the like.

The size-depth conversion table storage unit 125 stores predetermined relationships between: an area of an object and a rate of change of the area; and a depth and a depth change amount.

Movement of an object in the depth direction is proportional to the increase and decrease in area of the object in the screen. Accordingly, as an index for the object in the depth direction, for example an inter-frame area ratio which is a ratio between the area ratio of the object to the whole screen of the current frame and the area ratio of the object to the whole screen of the immediately previous frame is calculated and this inter-frame area ratio is divided by the area ratio to the whole screen of the immediately previous frame, to yield the degree of change of the area.

Meanwhile, when the object is smaller in depth, the area ratio of the object to the whole screen is higher, and the area change is greater even if the movement distance in the depth direction is short. Hence, the index for the degree of change of the area is multiplied by the inverse of the area ratio to the whole screen of the immediately previous frame.

Figure 10:
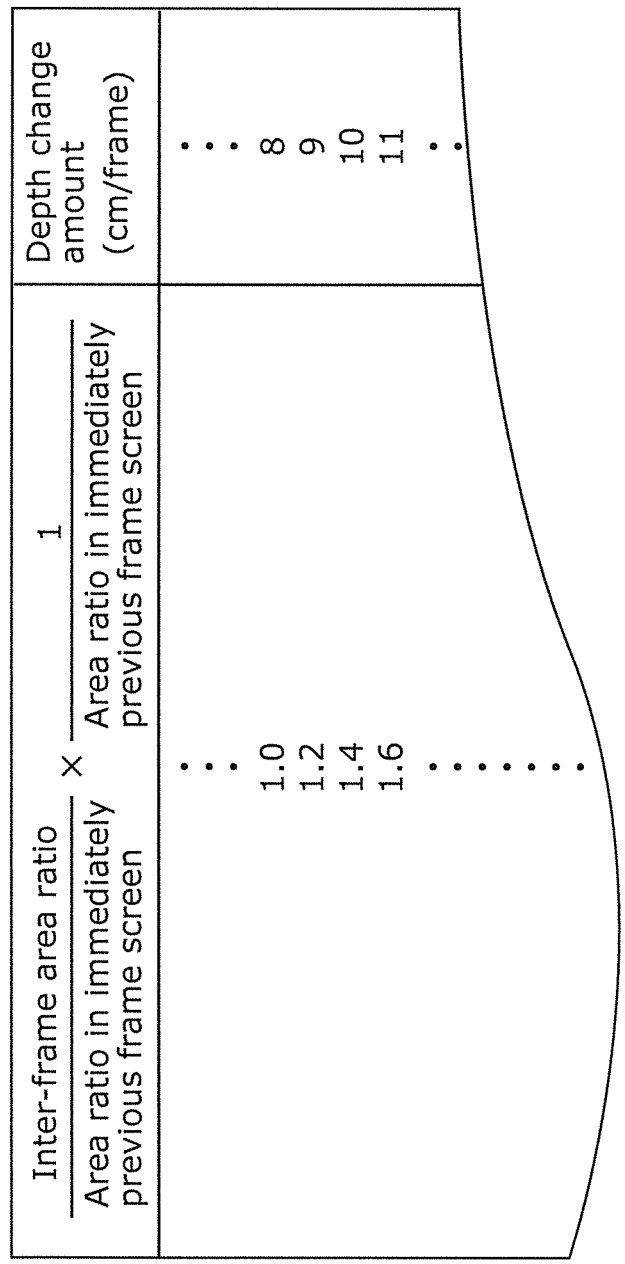
FIG. 10 is a diagram showing an example of a structure of data stored in a size-depth conversion table storage unit in Embodiment 1.

FIG. 10 is a diagram showing an example of information stored in the size-depth conversion table storage unit 125. The left column shows each value obtained by dividing the inter-frame area ratio between two consecutive frames in video content by the area ratio to the whole screen of the immediately previous frame and further multiplying the division result by the inverse of the area ratio to the whole screen of the immediately previous frame. The right column shows a predetermined depth change amount corresponding to the index shown in the left column.

For example, a table that indicates the depth change amount corresponding to the area change index calculated in this way is stored in the size-depth conversion table storage unit 125.

The depth change conversion unit 126 converts the calculation result of the size calculation unit 123 to the depth change amount, with reference to the table stored in the size-depth conversion table storage unit 125. The depth change conversion unit 126 obtains the size information of the object of the times corresponding to two consecutive frames, from the time information and size information stored in the storage unit 124. With the use of the obtained size information of each frame, the depth change conversion unit 126 calculates the result of dividing the ratio of the object area in the current frame to the object area in the previous frame by the square of the ratio of the object area to the screen size in the previous frame. The depth change conversion unit 126 then finds the depth change amount corresponding to the value calculated from the size information of each frame, with reference to the table stored in the size-depth conversion table storage unit 125.

Though the above describes the case where the relationships between: an area of an object and a rate of change of the area; and a depth change amount are fixed, the value in the table stored in the size-depth conversion table storage unit 125 differs depending on screen size. Hence, the depth change conversion unit 126 may calculate the depth change amount by multiplying the value by a coefficient corresponding to the size of the display screen 102, with reference to the table stored in the size-depth conversion table storage unit 125.

The movement determination table storage unit 127 stores determination criteria for switching between impedance measurement and electrooculogram measurement according to depth change information of objects.

FIG. 11 is a diagram showing an example of information stored in the movement determination table storage unit 127. For example, the table stored in the movement determination table storage unit 127 includes a same direction duration of an object, a speed of the object per frame, a logarithmic distance of movement of the object in the same direction, and electrooculogram measurement suitability determined beforehand from the combination of the above three conditions. The same direction duration is a time length during which the object in the video keeps moving in one direction. The speed per frame is a movement distance of the object per frame interval. The same direction movement logarithmic distance is a result of converting, to a logarithm, a movement distance in the series of movement in which the object keeps moving in one direction. The electrooculogram measurement suitability (hereafter also referred to as "suitability") is an index for determining whether or not the state is suitable for electrooculogram measurement, which is experimentally determined beforehand according to the conditions of the same direction duration, the speed per frame, and the same direction movement logarithmic distance. A higher value of the electrooculogram measurement suitability indicates more suitability to electrooculogram measurement. The absolute value of the electrooculogram is larger when the eye moves more at higher speed. The electrooculogram measurement suitability is higher in the case where the movement of the object in the video is greater and faster.

The same direction duration, the speed per frame, and the same direction movement logarithmic distance stored in the movement determination table storage unit 127 are each separated into predetermined numeric ranges as shown in FIG. 11. The electrooculogram measurement suitability corresponding to each numeric range is stored in the movement determination table storage unit 127.

Here, the movement determination table storage unit 127 may store at least two of the same direction duration, the speed per frame, and the same direction movement logarithmic distance. For instance, when the same direction duration and the speed per frame are stored in the movement determination table storage unit 127, the same direction movement logarithmic distance can be calculated from these two values.

The determination unit 128 determines the same direction duration, the speed per frame, and the same direction movement logarithmic distance, from the depth change amount of the object calculated by the depth change conversion unit 126 and the time and size stored in the storage unit 124. The determination unit 128 then determines the timing of switching between impedance measurement and electrooculogram measurement, with reference to the table stored in the movement determination table storage unit 127. For example, suppose an object is moving in the same direction for one second, with the speed per frame of 9.3 cm and the movement logarithmic distance of 2.45. The determination unit 128 extracts data A, with reference to the table stored in the movement determination table storage unit 127. The electrooculogram measurement suitability of the data A is 4. The determination unit 128 calculates the electrooculogram measurement suitability for each object included in each frame. For example in the case where at least one object whose suitability is greater than or equal to 5 is included in the frame or in the case where at least three objects whose suitability is greater than or equal to 3 are included in the frame, the determination unit 128 determines the frame as an electrooculogram measurement section. The times of the start frame and end frame of one electrooculogram measurement section are each set as the timing of switching between impedance measurement and electrooculogram measurement.

The measurement section determination unit 129 determines each time section for measuring the electrode contact impedance and each time section for measuring the viewer's electrooculogram, based on the measurement switching timing.

The measurement schedule storage unit 130 stores the measurement schedule on the time axis of the video content.

Figure 12:
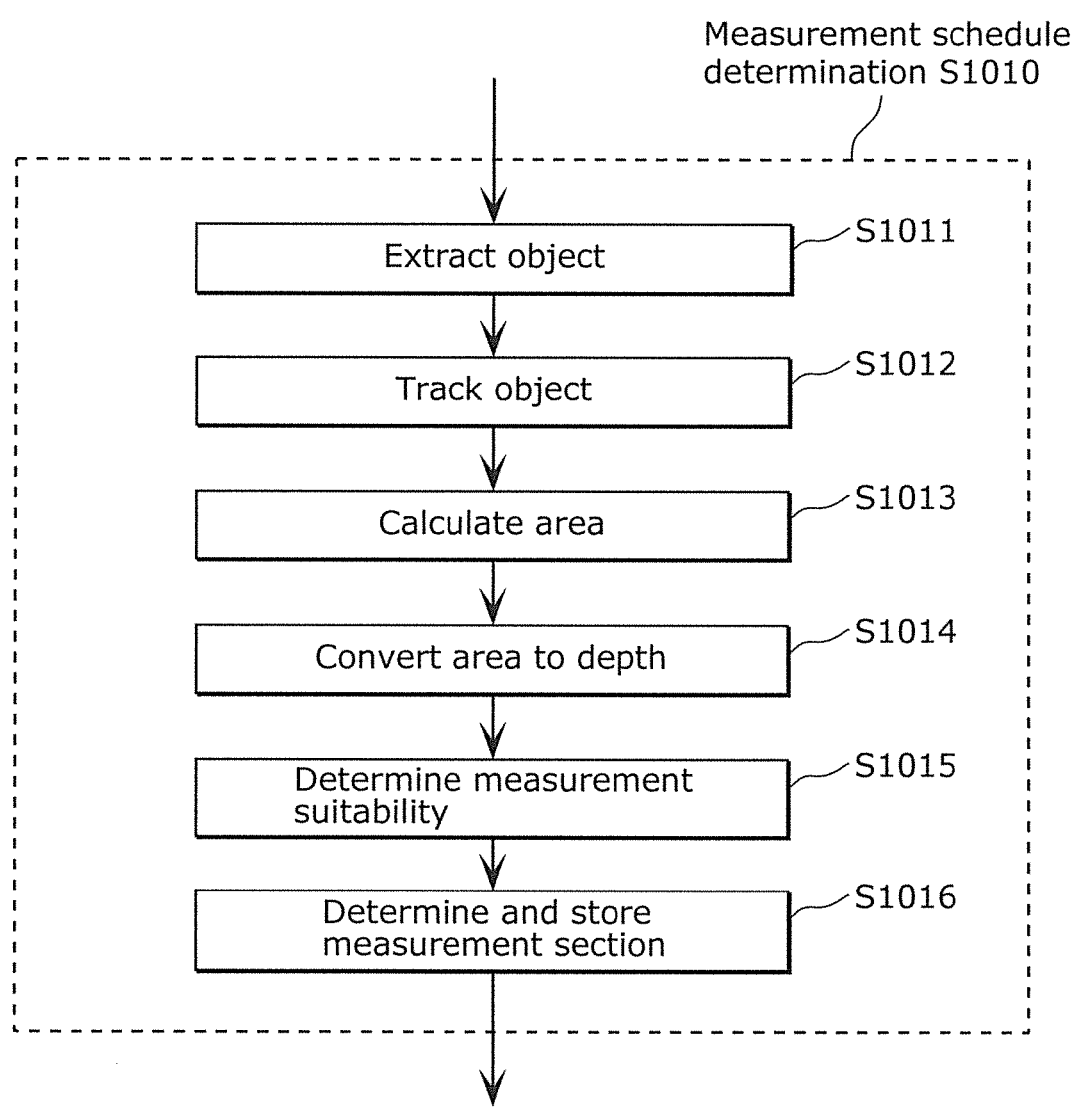
FIG. 12 is a flowchart showing an operation of the measurement schedule determination unit in Embodiment 1.
Figure 13:
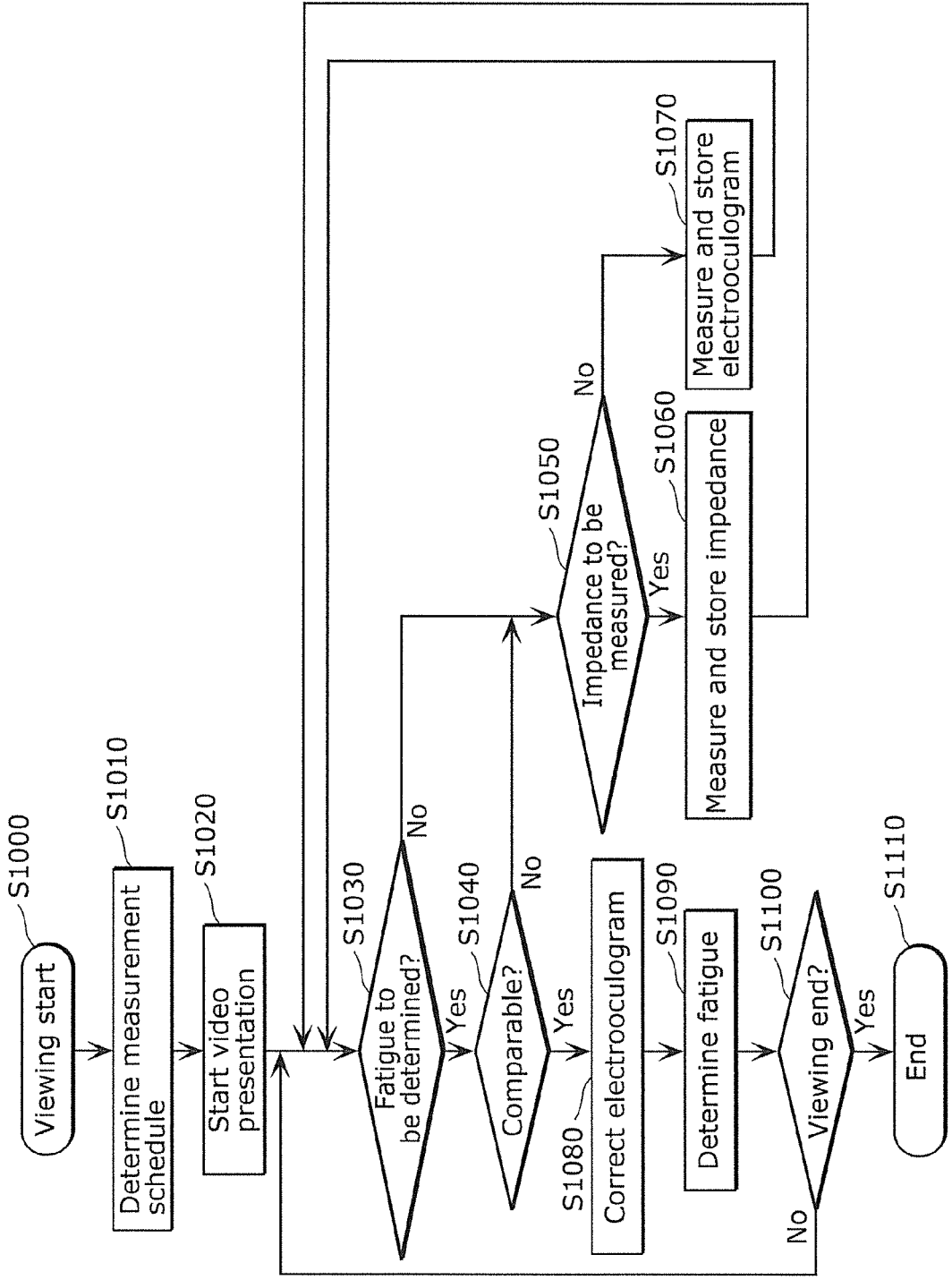
FIG. 13 is a flowchart showing an example of an operation of the eye fatigue measurement system in Embodiment 1.

FIG. 12 is a flowchart showing an operation of the measurement schedule determination unit 120, and corresponds to a measurement schedule determination step (S1010) in FIG. 13.

(Step S1011)

After the viewing starts (Step S1000 in FIG. 13), the object extraction unit 121 separates and extracts each object from the right-eye image or the left-eye image of each frame of the video. An example of the object separation method is regional division by clustering as described in NPL 2 (Ryoichi Suematsu and Hironao Yamada, "Mechatronics Textbook Series: Image Processing Engineering", Corona Publishing Co., Ltd., 2000).

(Step S1012)

The object tracking unit 122 specifies, from the objects in the frames extracted in Step S1011, the same object between the frames, and tracks the object. An example of the object tracking method is described in NPL 3 (Kenji Ikeda, Kousuke Imamura, and Hideo Hashimoto, "Video Segmentation and Moving Objects Tracking Using Spatio-Temporal Information", The journal of the Institute of Image Information and Television Engineers, Vol. 56, No. 8, pp. 1349 to 1353, 2002).

(Step S1013)

The size calculation unit 123 calculates, for each object tracked in Step S1012, the area of the object in each frame.

(Step S1014)

The depth change conversion unit 126 finds the difference in area of each object between frames, and calculates the relative change of the depth position of the object per frame, with reference to the table stored in the size-depth conversion table storage unit 125.

(Step S1015)

The change of the depth position of the object per frame indicates the movement of the object in the depth direction.

The determination unit 128 determines, according to the depth movement of each object included in the frame in the video, whether the frame is suitable for electrooculogram measurement or impedance measurement, with reference to the table stored in the movement determination table storage unit 127.

The method of the determination unit 128 determining whether or not the frame is suitable for electrooculogram measurement is described below.

For each object included in the frame, the determination unit 128 determines the corresponding electrooculogram measurement suitability with reference to the table stored in the movement determination table storage unit 127.

In the case where at least one object whose suitability is greater than or equal to 5 is included in the frame or in the case where at least three objects whose suitability is greater than or equal to 3 are included in the frame, the determination unit 128 determines the frame as an electrooculogram measurement section.

Note that any other determination criteria according to which a frame that includes an object (or objects) of high movement speed and long movement distance in the depth direction and so is expected to cause large eye movement of the viewer is determined as an electrooculogram measurement section may be used. In addition, determination criteria according to which the amount of eye movement in each electrooculogram measurement section is substantially equal in the case where the viewer does not have eye fatigue may be provided. That is, determination criteria according to which each of the movement speed and the movement distance is substantially equal in each electrooculogram measurement section may be provided.

(Step S1016)

The measurement section determination unit 129 sets consecutive frames suitable for electrooculogram measurement as an electrooculogram measurement section, and sets consecutive frames suitable for impedance measurement as an impedance measurement section. The measurement section determination unit 129 stores the measurement target for each frame in the measurement schedule storage unit 130.

For example, consecutive frames suitable for electrooculogram measurement are 12 frames. In the case where the frame rate of the video content is 60 frames per second, the time section of 12 frames corresponds to 200 milliseconds. For example when impedance measurement is performed using an electrical signal of 100 Hz, one period of the electrical signal is 10 ms. In such a case, measuring the impedance with an electrical signal of 20 periods requires 200 milliseconds. Though the frequency and the number of periods of the electrical signal used for impedance measurement may be other than these, consecutive frames constituting an impedance measurement section need to be consecutive frames of a time length greater than or equal to one period of the electrical signal used for impedance measurement.

The measurement schedule storage unit 130 may store only the switching frame or time between the electrooculogram measurement section and the impedance measurement section.

(Measured Impedance Storage Unit)

FIG. 7 is a diagram showing an example of a structure of data stored in the measured impedance storage unit 108.

The measured impedance storage unit 108 stores elapsed time information t from the video display start, time information T on the time axis of the video content, and information of the value of the impedance measured for each electrode.

In this embodiment, the measured impedance storage unit 108 further stores a signal frequency at the time of impedance measurement.

Moreover, in this embodiment, the measured impedance storage unit 108 stores not only the impedance values of the measurement electrodes a to f but also the impedance values of the reference electrode 211R and the body earth electrode 211E. Note that the measured impedance storage unit 108 may store the impedance value of a part of the electrodes 211 or the impedance values of all electrodes 211.

Though this embodiment describes the case where the measurement schedule determination unit 120 determines the image movement and sets the measurement sections for three-dimensional video content by calculating the object depth change, the measurement schedule determination unit 120 may determine the image movement for two-dimensional video content. In this case, the movement may be determined not based on the object depth change but, for example, based on the object movement amount on the screen plane per unit time. Here, the object movement amount in the two-dimensional video content is calculated by performing the object extraction process (Step S1011) and the object tracking process (Step S1012) shown in FIG. 12. In the case where a plurality of objects are present in frames of the two-dimensional video content, the object movement amount per unit time may be obtained by calculating the average or maximum movement amount of the plurality of objects as the object movement amount of each frame.

(Measured Electrooculogram Storage Unit)

FIG. 8 is a diagram showing an example of a structure of data stored in the measured electrooculogram storage unit 109.

The measured electrooculogram storage unit 109 stores elapsed time information t from the video display start, time information T on the time axis of the video content, and information of the value of the potential measured using each measurement electrode shown in FIGS. 4A and 4B.

The elapsed time information t from the video display start and the time information T on the time axis of the video content, which are stored in the measured impedance storage unit 108 and the measured electrooculogram storage unit 109, are information common to both units.

FIG. 13 is a flowchart showing an operation of the eye fatigue measurement system 1. The procedure performed by the eye fatigue measurement system 1 is described below, with reference to FIG. 13.

(Step S1000)

First, the viewer presses a power switch (not shown), to turn on the three-dimensional display device 10 and the three-dimensional eyeglasses 20. The eye fatigue measurement system 1 thus starts the operation.

(Step S1010)

The measurement schedule determination unit 120 determines, for content stored in the content information storage unit 101, each time section for impedance measurement and each time section for electrooculogram measurement on the time axis of the content.

(Step S1020)

The screen control unit 103 outputs the video of the content stored in the content information storage unit 101, to the display screen 102. At the same time, the screen control unit 103 generates a command signal for controlling synchronization between the image display on the display screen 102 and the shutter timing of the three-dimensional eyeglasses 20, and outputs the command signal to the control signal transmission unit 104. The screen control unit 103 thus starts the display of the stereoscopic video.

(Step S1030)

After the video display start, the fatigue determination unit 111 determines whether or not the current time is a fatigue determination time which is set to a predetermined time. For example, the fatigue determination unit 111 includes a timer, and stores information of the predetermined time for performing fatigue determination such as every 30 minutes from the viewing start. The fatigue determination unit 111 determines whether or not the elapsed time from the viewing start matches the predetermined time for performing fatigue determination, to determine whether or not the current time is the fatigue determination time.

In the case where the current time is the fatigue determination time in Step S1030 (Step S1030: Yes), the eye fatigue measurement system 1 proceeds to Step S1040.

In the case where the current time is not the fatigue determination time in Step S1030 (Step S1030: No), the eye fatigue measurement system 1 proceeds to Step S1050.

Though the fatigue determination unit 111 performs fatigue determination every 30 minutes in Step S1030 in this example, the fatigue determination unit 111 may perform fatigue determination at timings other than every 30 minutes, so long as at least 10 minutes have elapsed from the viewing start. There are instances where continuous viewing of stereoscopic video by children is limited to 15 minutes or less, in order to prevent adverse effects on children's vision. To promptly detect effects on vision or eyes, the time interval between the first time section and the second time section is preferably short. Meanwhile, for accurate fatigue determination, a time section of a sufficient time length for measuring the impedance and the electrooculogram is necessary. In view of this, it is desirable to set the time interval between the first time section and the second time section to at least 10 minutes, in order to promptly detect effects on vision or eyes and also ensure the measurement time for the impedance and the electrooculogram necessary for accurate fatigue determination.

(Step S1040)

The electrooculogram correction unit 110 checks whether or not new measurement data is stored in the measured impedance storage unit 108 and the measured electrooculogram storage unit 109 after immediately previous fatigue determination.

In the case of determining in Step S1040 that data stored in any of the measured impedance storage unit 108 and the measured electrooculogram storage unit 109 is insufficient for fatigue determination (Step S1040: No), the eye fatigue measurement system 1 proceeds to Step S1050.

In the case of determining in Step S1040 that data sufficient for fatigue determination is stored in the measured impedance storage unit 108 and the measured electrooculogram storage unit 109 (Step S1040: Yes), the eye fatigue measurement system 1 proceeds to Step S1080.

(Step S1050)

In Step S1050, the measurement switching control unit 106 checks whether or not the currently displayed video is video in a time section for impedance measurement on the time axis of the content.

In the case where the currently displayed video is in the time section for impedance measurement (Step S1050: Yes), the measurement switching control unit 106 generates a first command signal for performing impedance measurement, and outputs the first command signal to the transmission and reception unit 107 in the three-dimensional display device 10. The transmission and reception unit 107 transmits the first command signal received from the measurement switching control unit 106.

The transmission and reception unit 204 in the three-dimensional eyeglasses 20 receives the first command signal from the transmission and reception unit 107, and connects the switch 212 to the impedance measurement unit 213. As a result, the impedance measurement unit 213 enters a state of being capable of measuring the contact impedance of each electrode 211, and outputs data of the measured contact impedance to the transmission and reception unit 204 in the three-dimensional eyeglasses 20.

The transmission and reception unit 204 transmits the data received from the impedance measurement unit 213, to the three-dimensional display device 10.

(Step S1060)

The transmission and reception unit 107 in the three-dimensional display device 10 receives the data from the transmission and reception unit 204, and stores the data in the measured impedance storage unit 108.

(Step S1070)

In the case where the currently displayed video is not video in the time section for impedance measurement in Step S1050 (Step S1050: No), the measurement switching control unit 106 generates a second command signal for performing electrooculogram measurement, and outputs the second command signal to the transmission and reception unit 107 in the three-dimensional display device 10. The transmission and reception unit 107 transmits the second command signal received from the measurement switching control unit 106, to the three-dimensional eyeglasses 20. The transmission and reception unit 204 in the three-dimensional eyeglasses 20 receives the second command signal from the transmission and reception unit 107, and connects the switch 212 to the electrooculogram measurement unit 214. As a result, the electrooculogram measurement unit 214 enters a state of being capable of measuring the electrooculogram using the electrodes 211, and outputs data of the measured electrooculogram to the transmission and reception unit 204 in the three-dimensional eyeglasses 20. The transmission and reception unit 204 transmits the data received from the electrooculogram measurement unit 214, to the three-dimensional display device 10. The transmission and reception unit 107 in the three-dimensional display device 10 receives the data from the transmission and reception unit 204, and stores the data in the measured electrooculogram storage unit 109.

After Step S1060 or S1070, the eye fatigue measurement system 1 returns to Step S1030.

(Step S1080)

The electrooculogram correction unit 110 extracts the electrooculogram measured in the time closest to the video display start time, from the measured electrooculogram storage unit 109. The electrooculogram correction unit 110 also extracts the impedances before and after the measurement time section of the extracted electrooculogram, from the measured impedance storage unit 108. The electrooculogram correction unit 110 corrects the extracted electrooculogram using the impedances before and after the electrooculogram measurement time section, and outputs the corrected electrooculogram to the fatigue determination unit 111. In the case where only the impedance before or after the electrooculogram measurement time section is stored in the measured impedance storage unit 108, the extracted electrooculogram is corrected using the impedance before or after the electrooculogram measurement time section.

(Step S1090)

The fatigue determination unit 111 determines, with regard to the electrooculogram measured using the same electrode or the same electrode set and corrected in Step S1080, the viewer's fatigue based on the ratio between the average amplitude of the electrooculogram measured in the time closest to the video display start time and the average amplitude of the electrooculogram measured most recently. The fatigue determination method will be described later. The electrode set mentioned here is a pair of electrodes in the case where the potential difference between two electrodes is used as the measurement value.

(Step S1100)

The screen control unit 103 determines whether or not input for turning off the three-dimensional display device 10 or ending the viewing is made by the viewer by, for example, pressing the power switch (not shown), via the power switch or other input means (not shown).

(Step S1110)

In the case where input for turning off the three-dimensional display device 10 or ending the viewing is made in Step S1100, the eye fatigue measurement system 1 ends the operation (Step S1110).

In the case where there is no input for turning off the three-dimensional display device 10 or ending the viewing in Step S1100, the eye fatigue measurement system 1 returns to Step S1030. By repeatedly performing Steps S1030 to S1100, the eye fatigue measurement system 1 sequentially determines the viewer's fatigue during video display.

The time interval at which Steps S1030 to S1100 are repeated is, for example, 10 seconds. The fatigue determination unit 111 determines fatigue based on the elapsed time from the video display start. On the other hand, the measurement switching control unit 106 controls the time section switching based on the time on the time axis of the video content.

In the correction in Step S1080 and the fatigue determination in Step S1090, the electrooculogram data measured in the electrooculogram measurement section closest to the video display start time from among the electrooculogram data stored in the measured electrooculogram storage unit 109 and the impedance data measured in the impedance measurement sections before and after the electrooculogram measurement section are used as reference values.

Meanwhile, the electrooculogram data most recently stored in the measured electrooculogram storage unit 109 and the impedance data measured in the impedance measurement sections before and after the electrooculogram measurement section are used as data for determining the current fatigue.

The amplitude of the electrooculogram is proportional to the inverse of the ratio between the input impedance of the electrooculogram measurement unit 214 and the contact impedance of the electrode 211. Since the input impedance of the electrooculogram measurement unit 214 is fixed, the amplitude of the electrooculogram varies according to the contact impedance of the electrode 211.

Let EOGs be the value of the amplitude of the electrooculogram data measured in the electrooculogram measurement section closest to the video display start time, EOGm be the value of the amplitude of the electrooculogram data measured in the electrooculogram measurement section closest to the current time, Xs be the true value of the amplitude of the electrooculogram data measured in the electrooculogram measurement section closest to the video display start time, Xm be the true value of the amplitude of the electrooculogram data measured in the electrooculogram measurement section closest to the current time, ImpI be the input impedance of the electrooculogram measurement unit 214, ImpS be the average contact impedance of the electrode 211 measured before and after the electrooculogram measurement section closest to the video display start time, and ImpM be the average contact impedance of the electrode 211 measured before and after the electrooculogram measurement section closest to the current time. The measured electrooculograms EOGs and EOGm can be respectively represented by the following Expressions 1 and 2.

[Math. 1]

$$EOGs = X_s \frac{1}{Im\,pI/Im\,pS} \quad \text{(Expression 1)}$$

$$EOG_m = Xm \frac{1}{Im\,pI/Im\,pM}. \quad \text{(Expression 2)}$$

The input impedance, the measured contact impedance of the electrode 211, and the average contact impedance of the electrode 211 measured before and after the electrooculogram measurement section closest to the video display start time are stored in the measured impedance storage unit 108 as shown in FIG. 7 as an example.

The value of the amplitude of electrooculogram data is the difference between the maximum and minimum values of the time waveform generated by calculating the potential difference between two electrodes at each measurement time point. It is assumed here that the maximum and minimum values of the time waveform are the maximum and minimum values of the time waveform in a measurement section. The two electrodes are, for example, the electrodes a and b, the electrodes c and d, the electrodes b and e, or the electrodes c and f as shown in FIG. 8. The two electrodes are desirably a pair of electrodes placed at the positions between which one or two eyes are present. The electrooculogram measurement data of each electrode at each measurement time point and the amplitude of the electrooculogram data measured in the electrooculogram measurement section closest to the video display start time are stored in the measured electrooculogram storage unit 109 as shown in FIG. 8 as an example.

Figure 14:
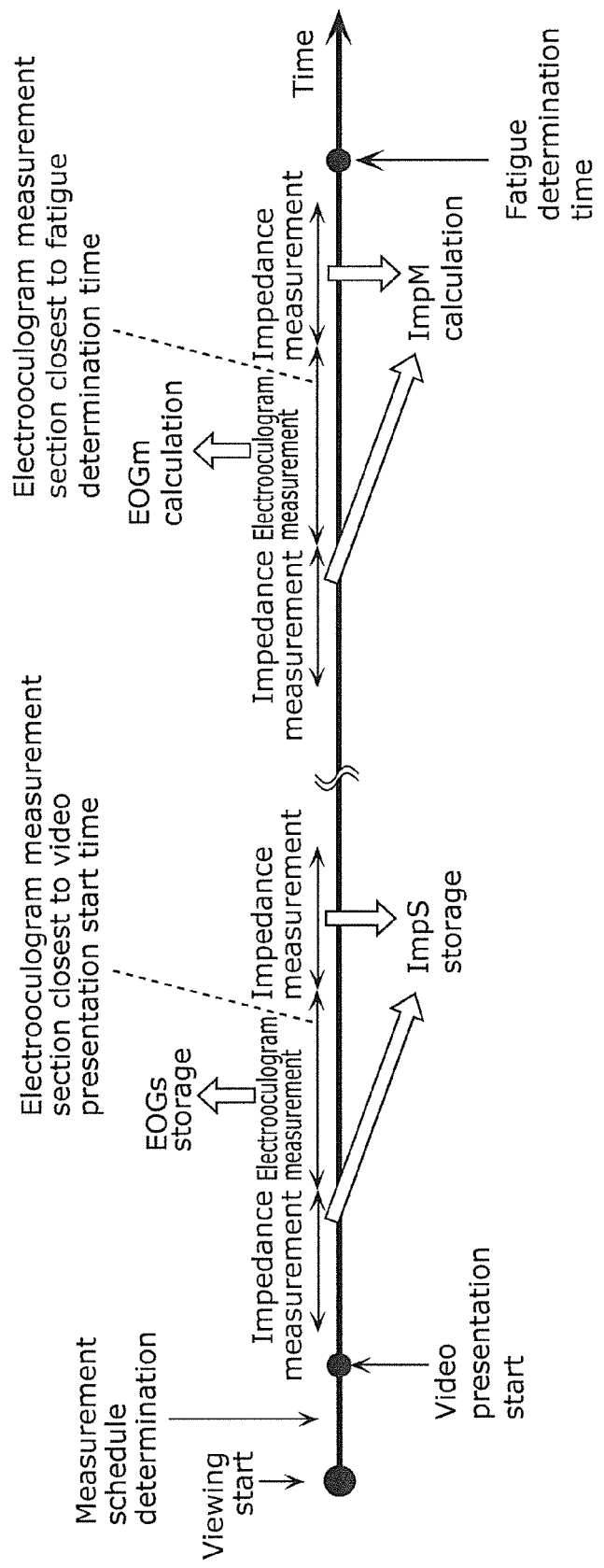
FIG. 14 is a schematic diagram showing measurement schedule determination, impedance measurement, electrooculogram measurement, and fatigue determination after viewing start in chronological order in Embodiment 1.

FIG. 14 is a schematic diagram showing time relationships between impedance measurement and electrooculogram measurement. After the viewing start, the measurement schedule determination is performed first, and the video display starts. EOGs is generated from the electrooculogram data measured in the first electrooculogram measurement section after the video display start, and stored in the measured electrooculogram storage unit 109. EOGm is generated from the electrooculogram data measured in the electrooculogram measurement section that precedes the predetermined fatigue determination time and is closest to the fatigue determination time.

To measure fatigue caused by video viewing, it is necessary to compare the eye state at the time of video viewing start and the eye state during video viewing or at the time of video viewing end.

Precisely, there is a need to compare Xs and Xm when following exactly the same visual index by the eye movement in the same manner. It is, however, impossible to conduct test using exactly the same visual index in video content. Accordingly, for example, the long-time average amplitude of about 1 to 5 minutes is subjected to comparison. The use of the long-time average smooths out content discrepancies. The above-mentioned two expressions are unchanged even when EOGs and EOGm denote the measured values of the long-time averages and Xs and Xm denote the true values of the long-time averages. For example, in the case of using the ratio of Xm to Xs in the method of comparing Xs and Xm, the ratio is written as shown in the following Expression 3. Thus, the eye state comparison can be performed by correcting the measured electrooculogram using the measured impedance.

[Math. 2]

$$\frac{Xm}{Xs} = \frac{EOG_m(Im\,PI/Im\,pM)}{EOGs(Im\,pI/Im\,pS)} = \frac{EOGm/Im\,pM}{EOGs/Im\,pS} \quad \text{(Expression 3)}$$

The fatigue determination unit 111 determines that the viewer has eye fatigue in the case where the value of Xm/Xs is less than 0.75, as an example.

Though the above describes the case where the ratio between Xm and Xs is used for fatigue determination, other determination methods such as using the difference between Xm and Xs are also applicable.

Though the above describes the case where the amplitude of the electrooculogram is the difference between the maximum and minimum values in the measurement section, the electrooculogram may be calculated as follows: the potential difference between peaks in the time waveform of the potential difference between two electrodes in the measurement section is calculated, and the average of the inter-peak potential difference is set as the amplitude of the electrooculogram. Alternatively, the root mean square of the potential difference in the time waveform of the potential difference between two electrodes in the measurement section may be set as the amplitude.

Thus, the depth movement of the object included in the video content is used as the index to switch between impedance measurement and electrooculogram measurement. Moreover, the electrooculogram is corrected using the contact impedance of the electrode measured in the time section near the electrooculogram measurement section, and the eye state upon video viewing start and the eye state upon fatigue determination are compared using the corrected electrooculogram. By comparing the untired eye state immediately after video viewing start and the eye state after continuous video viewing while eliminating the effects of impedance fluctuations immediately after video viewing start and impedance fluctuations caused by, for example, adjusting the eyeglasses, the viewer's fatigue can be detected more accurately.

The elapsed time from the video display start and the time on the time axis of the video content are stored in both the measured impedance storage unit 108 and the measured electrooculogram storage unit 109. This enables necessary electrooculogram and impedance to be extracted even in the case where an operation performed by the viewer on the video such as a pause or rewinding and reproduction causes a lag between the time from the video display start and the time on the time axis of the content.

In Embodiment 1, the movement of the object included in the video content in the depth direction is used as the index to switch between the impedance measurement section and the electrooculogram measurement section. In this method, however, the speed of the movement in the depth direction changes in the case where the viewer fast-forwards the video or reproduces the video in slow motion. In slow-motion reproduction, the speed of the eye movement during viewing is expected to be lower, which is not suitable for electrooculogram measurement. When the viewer fast-forwards the video or reproduces the video at double speed, on the other hand, the speed of the eye movement is expected to be higher, which is suitable for electrooculogram measurement. Hence, the measurement schedule storage unit 130 stores not only the measurement target but also the electrooculogram measurement suitability for each frame or each time on the time axis of the video content.

In the case where the viewer changes the reproduction speed of the video via input means (not shown), the screen control unit 103 outputs reproduction speed information to the measurement switching control unit 106.

The reproduction speed information is, for example, information of the ratio of the reproduction speed to the normal reproduction speed.

With reference to the electrooculogram measurement suitability stored in the measurement schedule storage unit 130, the measurement switching control unit 106 rewrites the measurement schedule so that, during slow-motion reproduction, electrooculogram measurement is performed in the case where the electrooculogram measurement suitability is higher and, during fast forwarding or double-speed reproduction, electrooculogram measurement is performed even in the case where the electrooculogram measurement suitability is lower. The measurement switching control unit 106 then outputs a measurement switching control signal.

Figure 15:
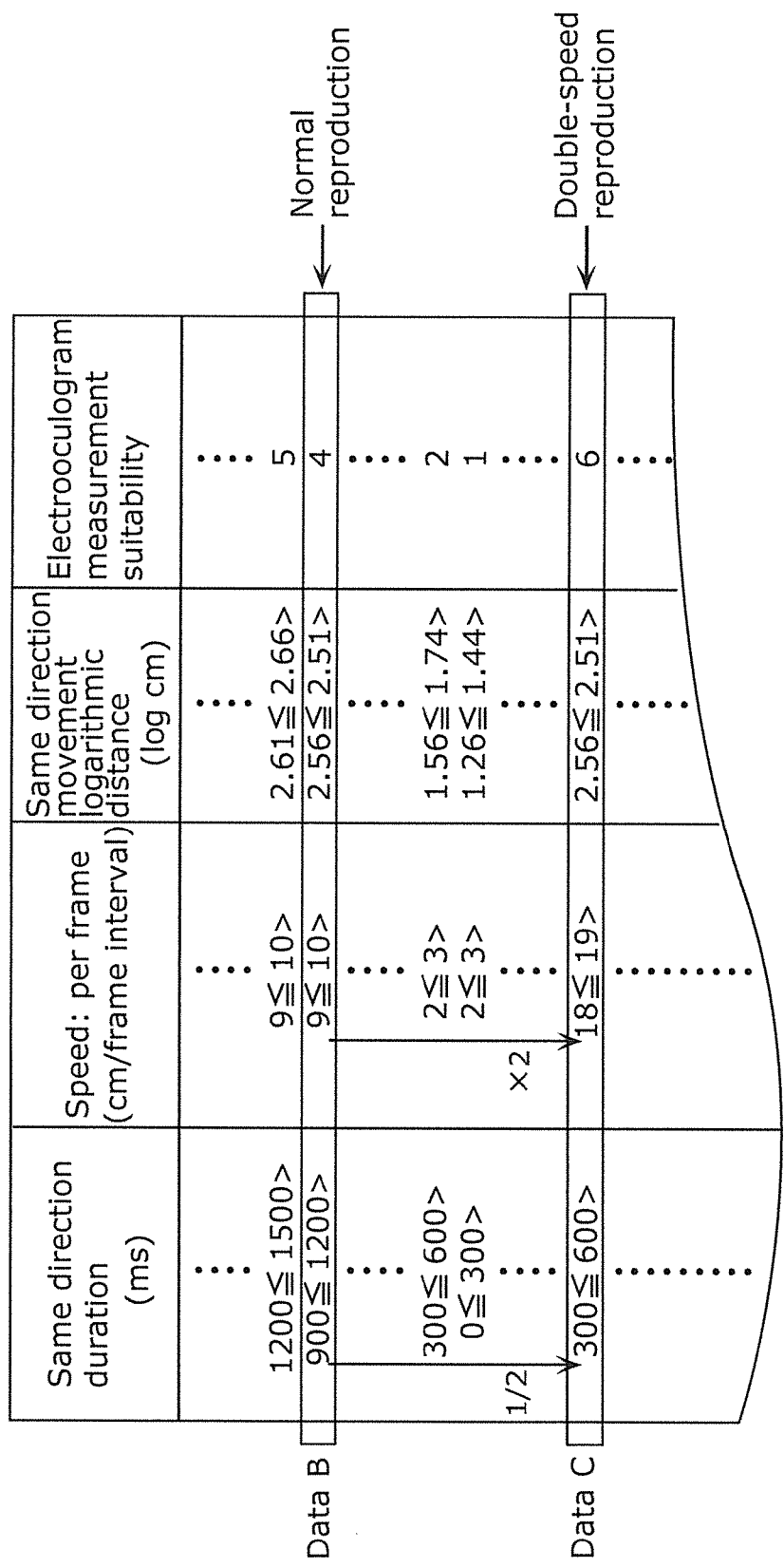
FIG. 15 is a schematic diagram showing an example of a change in electrooculogram measurement suitability in double-speed reproduction in Embodiment 1.

FIG. 15 is a diagram showing an example of a change of electrooculogram measurement suitability in double-speed reproduction.

For instance, when an object is reproduced at normal speed, the same direction duration is 1 second (1000 ms), the speed per frame is 9.3 cm, and the same direction movement logarithmic distance is 2.45. In this case, data B is extracted, where the electrooculogram measurement suitability of the object is 4. When the object is reproduced at double speed, on the other hand, the same direction duration is 500 ms, the speed per frame is 18.6 cm, and the same direction movement logarithmic distance is 2.45. In this case, data C is extracted, where the electrooculogram measurement suitability of the object is 6.

In double-speed reproduction, the movement time of the object for determining the electrooculogram measurement suitability is reduced by half while the speed of the object for determining the electrooculogram measurement suitability is doubled, so that the movement logarithmic distance is unchanged. The electrooculogram measurement suitability is higher in double-speed reproduction than in normal-speed reproduction. The measurement switching control unit 106 in this embodiment does not obtain the movement information of each object, and so changes the switching criteria for the electrooculogram measurement suitability based on the reproduction speed information. The measurement switching control unit 106 also instructs the measurement schedule determination unit 120 to re-determine the measurement schedule based on the reproduction speed information. In this way, the switching between electrooculogram measurement and impedance measurement can be made at appropriate timing even when the viewer changes the reproduction speed.

For instance, the measurement schedule is changed for a predetermined period such as 5 minutes from when a reproduction speed-related operation such as fast forwarding is performed. Each time a reproduction speed-related operation is performed, the measurement schedule for the predetermined period from the time of the operation is changed. If no operation is performed, the time section is extended to change the measurement schedule. The determination criteria for the movement of the object in the depth direction are thus changed according to the reproduction speed during viewing. This enables eye movement measurement suitable for fatigue determination to be performed even when the expected eye movement state changes as a result of the viewer changing the reproduction speed such as by slow-motion reproduction, fast forwarding, or double-speed reproduction.

Figure 16:
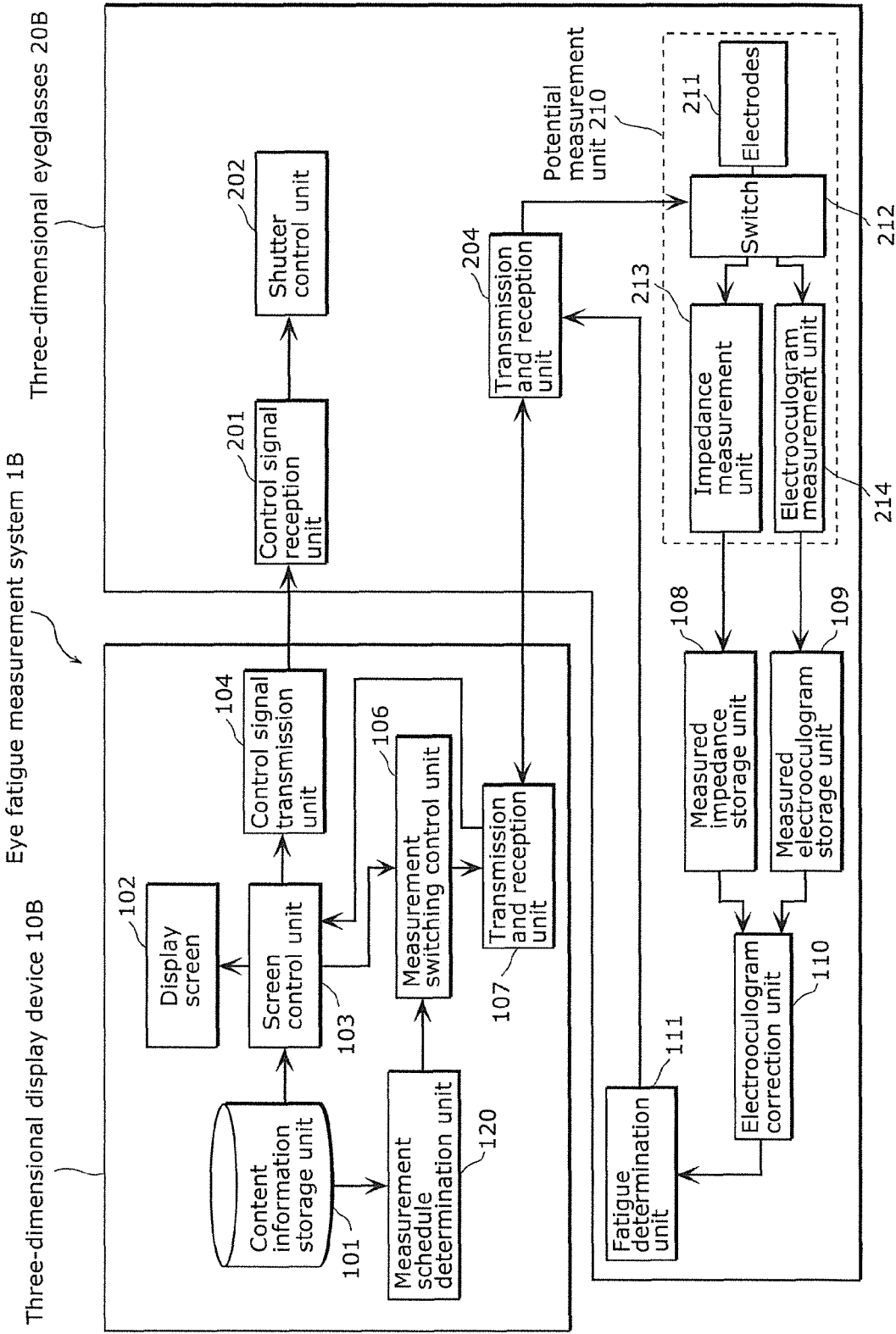
FIG. 16 is a block diagram showing an example of another structure of the eye fatigue measurement system in Embodiment 1.

Embodiment 1 describes the case where the three-dimensional eyeglasses 20 include the potential measurement unit 210 and the transmission and reception unit 204 as shown in FIG. 3. As another example, as shown in FIG. 16, the potential measurement unit 210, the measured impedance storage unit 108, the measured electrooculogram storage unit 109, the electrooculogram correction unit 110, and the fatigue determination unit 111 may be included not in a three-dimensional display device 10B but in three-dimensional eyeglasses 20B so that the three-dimensional eyeglasses 20B perform Steps S1030 to S1090.

In such a case, the transmission and reception unit 204 receives the measurement switching control signal from the transmission and reception unit 107 in the three-dimensional display device 10B, and transmits the fatigue determination result to the transmission and reception unit 107. The transmission and reception unit 107 outputs the received fatigue determination result to the screen control unit 103.

From among the potential measurement unit 210, the electrodes 211, the switch 212, the impedance measurement unit 213, and the electrooculogram measurement unit 214 included in the potential measurement unit 210, the measured impedance storage unit 108, the measured electrooculogram storage unit 109, the electrooculogram correction unit 110, and the fatigue determination unit 111, the structural elements other than the electrodes 211 may be included in any of the three-dimensional eyeglasses 20B and the three-dimensional display device 10B.

Embodiment 1 describes the case where the switch 212 switches between the impedance measurement unit 213 and the electrooculogram measurement unit 214 so as to measure the electrooculogram in each section suitable for electrooculogram measurement and measure the impedance in the other sections. As an alternative, the switch 212 may be capable of switching among the impedance measurement unit 213, the electrooculogram measurement unit 214, and the earth, thus providing a section in which neither electrooculogram measurement nor impedance measurement is performed. In such a case, for example, the time length of the time section for impedance measurement is fixed, and the impedance measurement unit 213 measures the impedance only in the section of the predetermined time such as 1 second immediately before the electrooculogram measurement and in the section of the predetermined time such as 1 second immediately after the electrooculogram measurement. As a result of measuring the impedance only in each of the time sections closer to the electrooculogram measurement, an impedance value closer to that during the electrooculogram measurement can be obtained as the measured impedance. This enables the electrooculogram correction unit 110 to correct the electrooculogram more accurately using the more accurate impedance, and therefore enables the fatigue determination unit 111 to determine fatigue more accurately.

Embodiment 2

Figure 17:
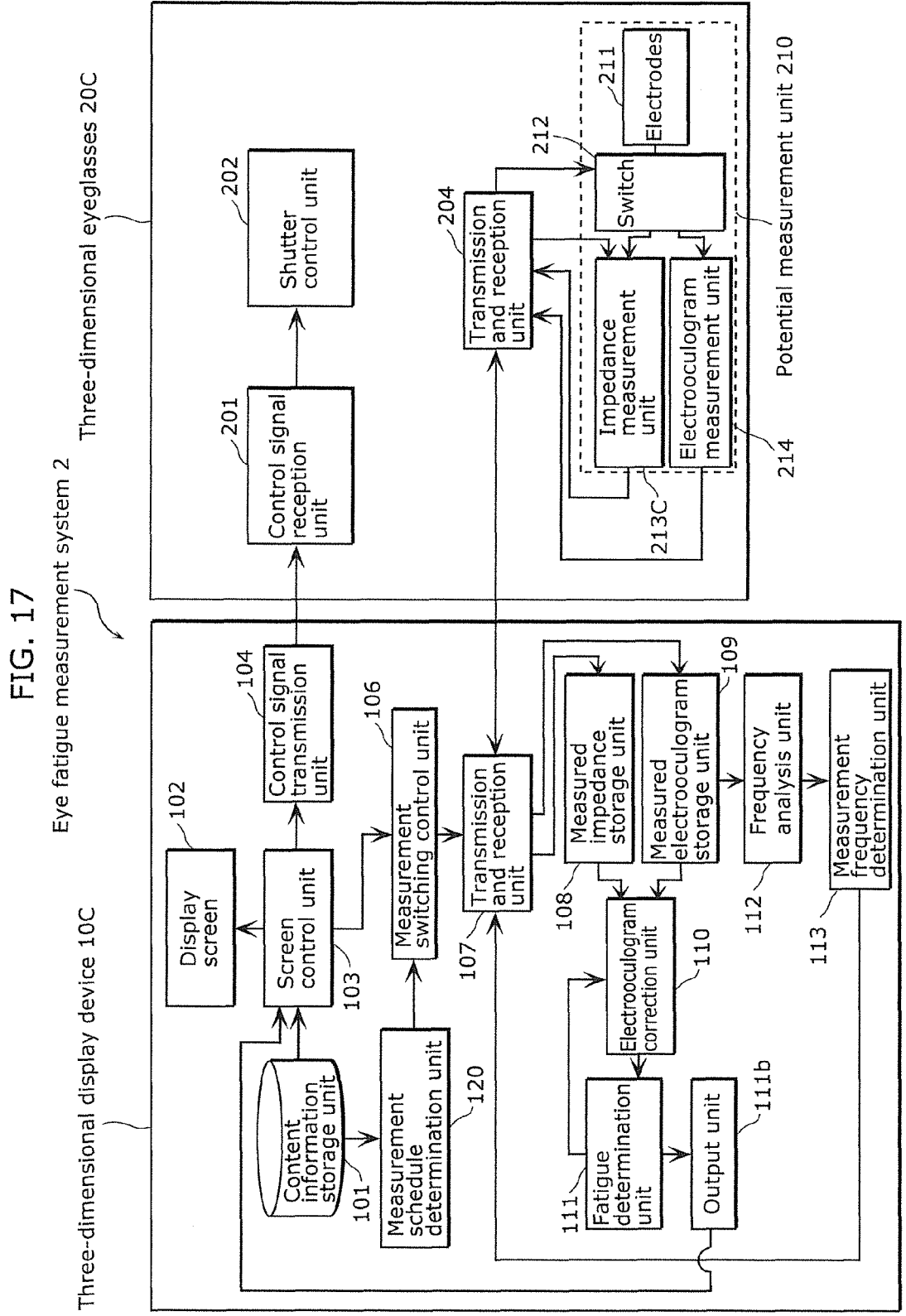
FIG. 17 is a block diagram showing an example of a structure of an eye fatigue measurement system in Embodiment 2.

FIG. 17 is a diagram showing a structure of an eye fatigue measurement system 2 in Embodiment 2.

The eye fatigue measurement system 2 includes a three-dimensional display device 10C and three-dimensional eyeglasses 20C.

The three-dimensional display device 10C includes a frequency analysis unit 112 and a measurement frequency determination unit 113, in addition to the structure of the three-dimensional display device 10. The three-dimensional eyeglasses 20C include an impedance measurement unit 213C instead of the impedance measurement unit 213. The same parts as those in FIG. 3 are given the same reference signs, and their description is omitted as appropriate.

The frequency analysis unit 112 analyzes the frequency of the electrooculogram stored in the measured electrooculogram storage unit 109.

The measurement frequency determination unit 113 determines the frequency of the output signal used for impedance measurement, based on the frequency of the electrooculogram output from the frequency analysis unit 112.

Figure 18:
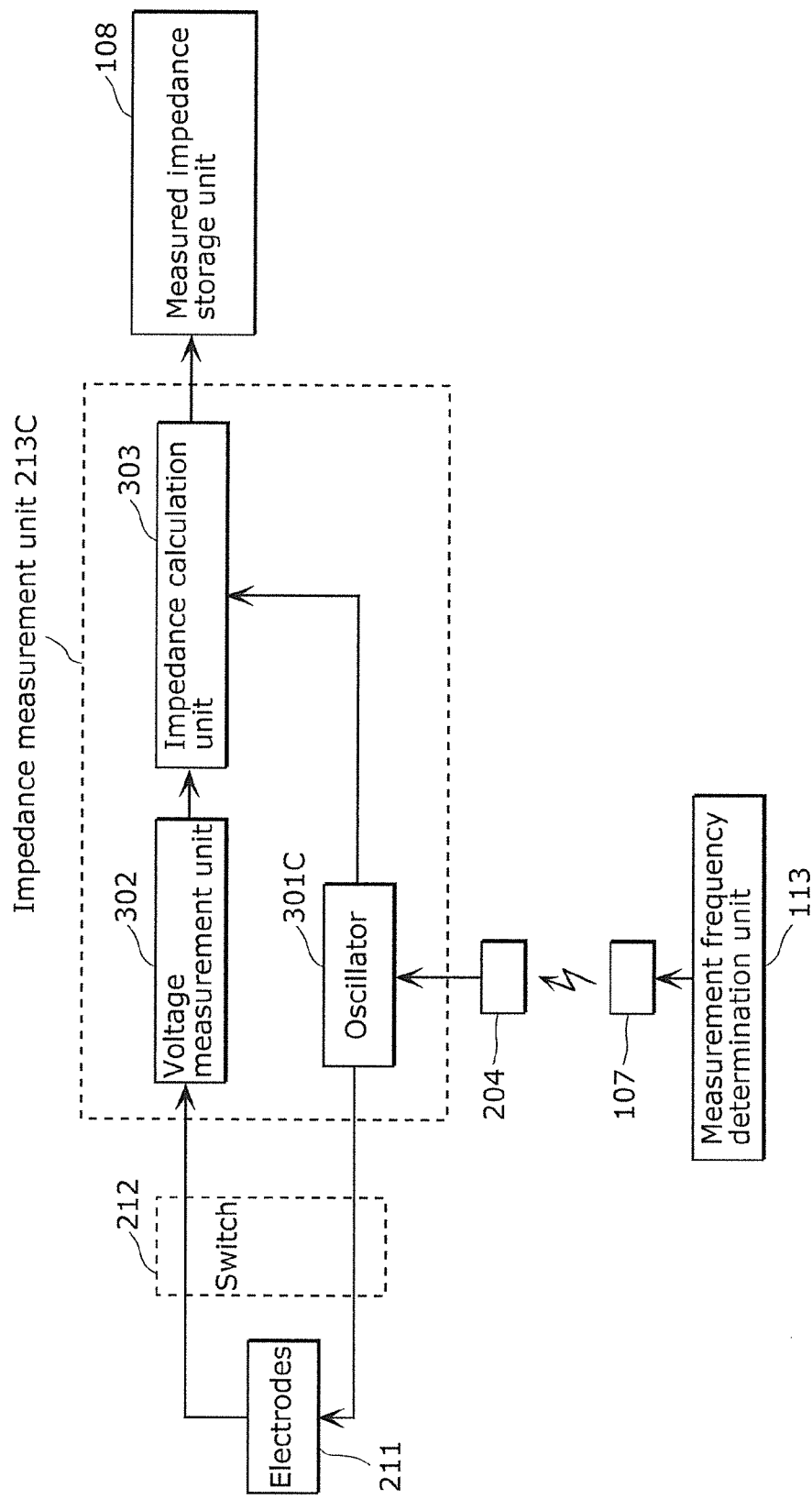
FIG. 18 is a diagram showing a detailed structure of an impedance measurement unit in Embodiment 2.

FIG. 18 is a diagram showing a detailed structure of the impedance measurement unit 213C in the three-dimensional eyeglasses 20C.

The impedance measurement unit 213C includes an oscillator 301C, the voltage measurement unit 302, and the impedance calculation unit 303.

The oscillator 301C generates the signal for impedance measurement. The oscillator 301C uses the frequency determined by the measurement frequency determination unit 113 and received from the transmission and reception unit 107 via the transmission and reception unit 204, as the oscillation frequency.

The voltage measurement unit 302 measures the voltage of the signal received from the electrodes 211 via the switch 212.

The impedance calculation unit 303 calculates the impedance by comparing the voltage value output from the oscillator 301C and the voltage value measured by the voltage measurement unit 302.

Figure 19:
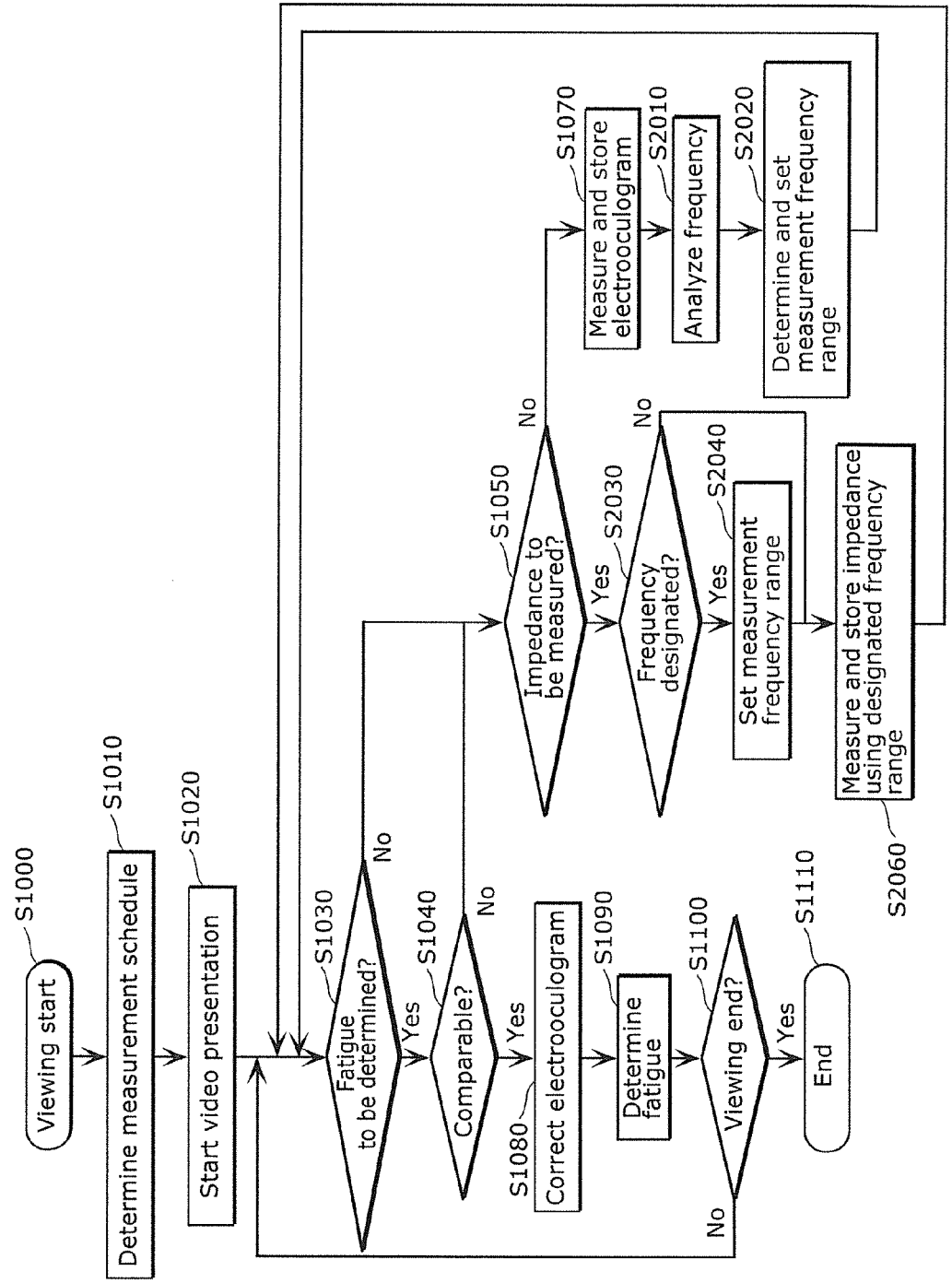
FIG. 19 is a flowchart showing an example of an operation of the eye fatigue measurement system in Embodiment 2.

FIG. 19 is a flowchart showing an operation of the eye fatigue measurement system 2 in Embodiment 2. The flowchart shown in FIG. 19 is the same as the flowchart shown in FIG. 13, except that Steps S2010, S2020, S2030, and S2040 are added and Step S1060 is replaced with Step S2060.

Steps S1000 to S1050 and S1070 in FIG. 19 are the same as those in FIG. 13.
(Step S1050)

The measurement switching control unit 106 checks whether or not the currently displayed video is video in a time section for impedance measurement.

In the case where the currently displayed video is in the time section for impedance measurement, the measurement switching control unit 106 generates the first command signal for performing impedance measurement, and outputs the first command signal to the transmission and reception unit 107.

The transmission and reception unit 107 transmits the first command signal to the three-dimensional eyeglasses 20C. The transmission and reception unit 204 in the three-dimensional eyeglasses 20C receives the first command signal from the transmission and reception unit 107, and connects the switch 212 to the impedance measurement unit 213C. As a result, the impedance measurement unit 213C enters a state of being capable of measuring the contact impedance of each electrode 211.
(Step S1070)

In the case of determining in Step S1050 that the currently displayed video is not video in the time section for impedance measurement, on the other hand, the measurement switching control unit 106 generates a control signal for connecting the switch to the electrooculogram measurement unit 214, and outputs the control signal to the transmission and reception unit 107 in the three-dimensional display device 10C. The transmission and reception unit 107 transmits the control signal received from the measurement switching control unit 106. The transmission and reception unit 204 in the three-dimensional eyeglasses 20C receives the signal from the transmission and reception unit 107, and connects the switch 212 to the electrooculogram measurement unit 214. As a result, the electrooculogram measurement unit 214 enters a state of being capable of measuring the electrooculogram using the electrodes 211, and outputs data of the measured electrooculogram to the transmission and reception unit 204 in the three-dimensional eyeglasses 20C. The transmission and reception unit 204 transmits the data received from the electrooculogram measurement unit 214. The transmission and reception unit 107 in the three-dimensional display device 10C receives the data from the transmission and reception unit 204, and stores the data in the measured electrooculogram storage unit 109.
(Step S2010)

The frequency analysis unit 112 analyzes the frequency of the electrooculogram data stored in the measured electrooculogram storage unit 109.
(Step S2020)

The measurement frequency determination unit 113 determines the frequency range of the signal used for impedance measurement, according to the output of the frequency analysis unit 112.

For example, in the case where the frequency of the electrooculogram is 12 Hz to 16 Hz, the measurement frequency determination unit 113 sets the frequency range of 10 Hz to 40 Hz that includes the frequency range of the electrooculogram with at least a 10% allowance above and below the frequency of the electrooculogram. Though the allowance upon setting the frequency range is 10% in this example, the allowance may be other than this value.
(Step S2030)

The impedance measurement unit 213C checks whether or not a signal for designating the measurement frequency range determined in Steps S2010 and S2020 is received from the transmission and reception unit 204.

In the case where the measurement frequency range designation signal is received (Step S2030: Yes), the eye fatigue measurement system 2 proceeds to Step S2040.

In the case where the measurement frequency range designation signal is not received (Step S2030: No), the eye fatigue measurement system 2 proceeds to Step S2060.
(Step S2040)

The frequency of the oscillator 301C is set according to the measurement frequency range designation signal determined in Steps S2010 and S2020 and received by the oscillator 301C from the transmission and reception unit 204. For example, the range of 10 Hz to 1000 Hz is set in the oscillator 301C as an initial value of the measurement frequency range.
(Step S2060)

The oscillator 301C outputs the measurement signal of predetermined voltage and current to the reference electrode of the electrodes 211, according to the frequency range set in the oscillator 301C. The voltage measurement unit 302 measures the voltage obtained from the electrode 211 other than the reference electrode.

The impedance calculation unit 303 calculates the impedance at the signal frequency of the output of the oscillator 301C, from the signal output from the oscillator 301C and the voltage obtained from the electrode 211. The calculated impedance is stored in the measured impedance storage unit 108.

After Step S2060 or S2020, the eye fatigue measurement system 2 returns to Step S1030.

By sequentially setting the frequency range for impedance measurement according to the frequency of the measured electrooculogram in this way, the impedance for correcting the electrooculogram used in fatigue determination can be measured at the frequency of the electrooculogram which is the signal to be measured.

FIG. 20 is a diagram schematically showing relationships between the impedance and the frequency. When the frequency is lower, the impedance is higher. In frequencies lower than 10 Hz, the difference in impedance depending on frequency is significant. Since the frequency of the electrooculogram is often below 10 Hz, the impedance significantly differs depending on the frequency of the electrooculogram. Therefore, the extent to which the impedance influences the amplitude of the electrooculogram differs depending on the frequency of the electrooculogram.

With the structure in this embodiment, the electrooculogram correction error caused by the difference in impedance depending on frequency can be reduced. As a result, eye fatigue can be determined more accurately.

Here, the measurement schedule determination unit 120 is not an essential structural element. In detail, the measurement schedule of the electrooculogram and the contact impedance determined by the measurement schedule determination unit 120 may be included in the video content stored in the content information storage unit 101 in association with the time information of the content, as auxiliary information. In such a case, the measurement switching control unit 106 controls the switching between electrooculogram measurement and contact impedance measurement, with reference to the auxiliary information of the video content.

Embodiment 3

Figure 21:
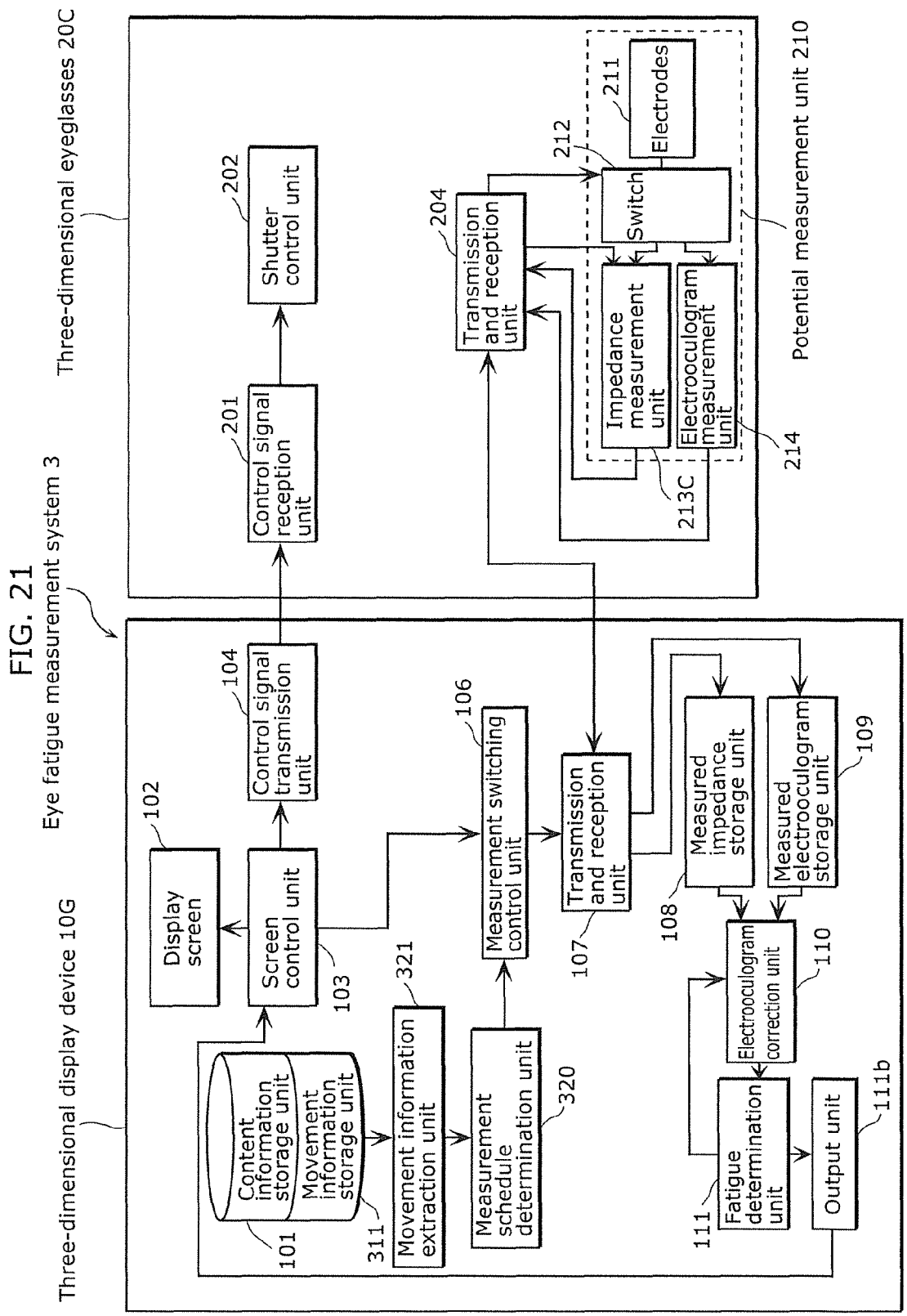
FIG. 21 is a block diagram showing an example of a structure of an eye fatigue measurement system in Embodiment 3.

FIG. 21 is a diagram showing a structure of an eye fatigue measurement system 3 in Embodiment 3.

The eye fatigue measurement system 3 includes a three-dimensional display device 10G and the three-dimensional eyeglasses 20C.

The three-dimensional display device 10G includes a measurement schedule determination unit 320 instead of the measurement schedule determination unit 120 in the three-dimensional display device 10 shown in FIG. 3, and further includes a movement information storage unit 311 and a movement information extraction unit 321. The other structure is the same as that of the three-dimensional display device 10. The three-dimensional eyeglasses 20C have the same structure as the three-dimensional eyeglasses 20C shown in FIG. 17. The same parts as those in FIG. 3 or 17 are given the same reference signs, and their description is omitted as appropriate.

With the structure in this embodiment, electrooculogram measurement and impedance measurement can be performed at appropriate timing based on movement information of an object displayed on the screen, and also the impedance can be measured at a frequency corresponding to predicted electrooculogram.

The movement information storage unit 311 stores movement information of each object in content video corresponding to content information.

The movement information extraction unit 321 extracts movement information of each object from the movement information storage unit 311.

The measurement schedule determination unit 320 determines the frequency range of the signal used for impedance measurement based on object speed, and also determines the time section for electrooculogram measurement and the time section for impedance measurement.

FIG. 22A is a diagram showing an example of movement information of video content stored in the movement information storage unit 311. For example, the movement information storage unit 311 stores data for each content item. In detail, the movement information storage unit 311 stores content identification information and standard screen size information of the content. The movement information storage unit 311 also stores a time from the start of the content video, a frame number, an ID of each object in the video content on a frame basis, and a virtual barycentric coordinate position (standard three-dimensional coordinates) of the object upon content generation. The content identification information and the time are the same as the information stored in the content information storage unit 101.

Figure 22B:
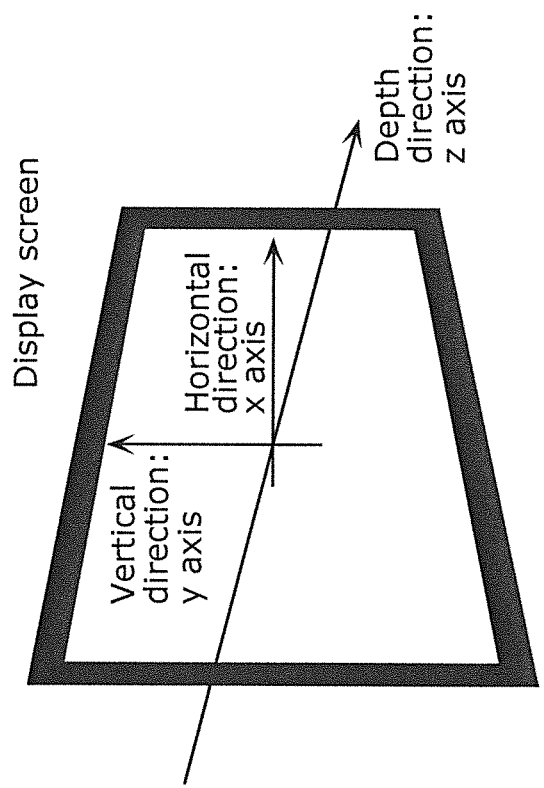
FIG. 22B is a diagram showing an example of coordinate axes for representing movement information.

FIG. 22B is a diagram showing an example of arrangement of coordinate axes in the standard three-dimensional coordinates of movement information. The horizontal direction and vertical direction of a plane parallel to the display screen are respectively the x axis and the y axis, and the direction perpendicular to the display screen is the z axis as the depth direction. The center of the display screen is the origin. The right direction and left direction of the display screen are respectively the positive and negative sides of the x axis, and the up direction and down direction of the display screen are respectively the positive and negative sides of the y axis. The direction forward from the display screen is the positive side of the z axis, and the direction backward from the display screen is the negative side of the z axis.

Figure 23:
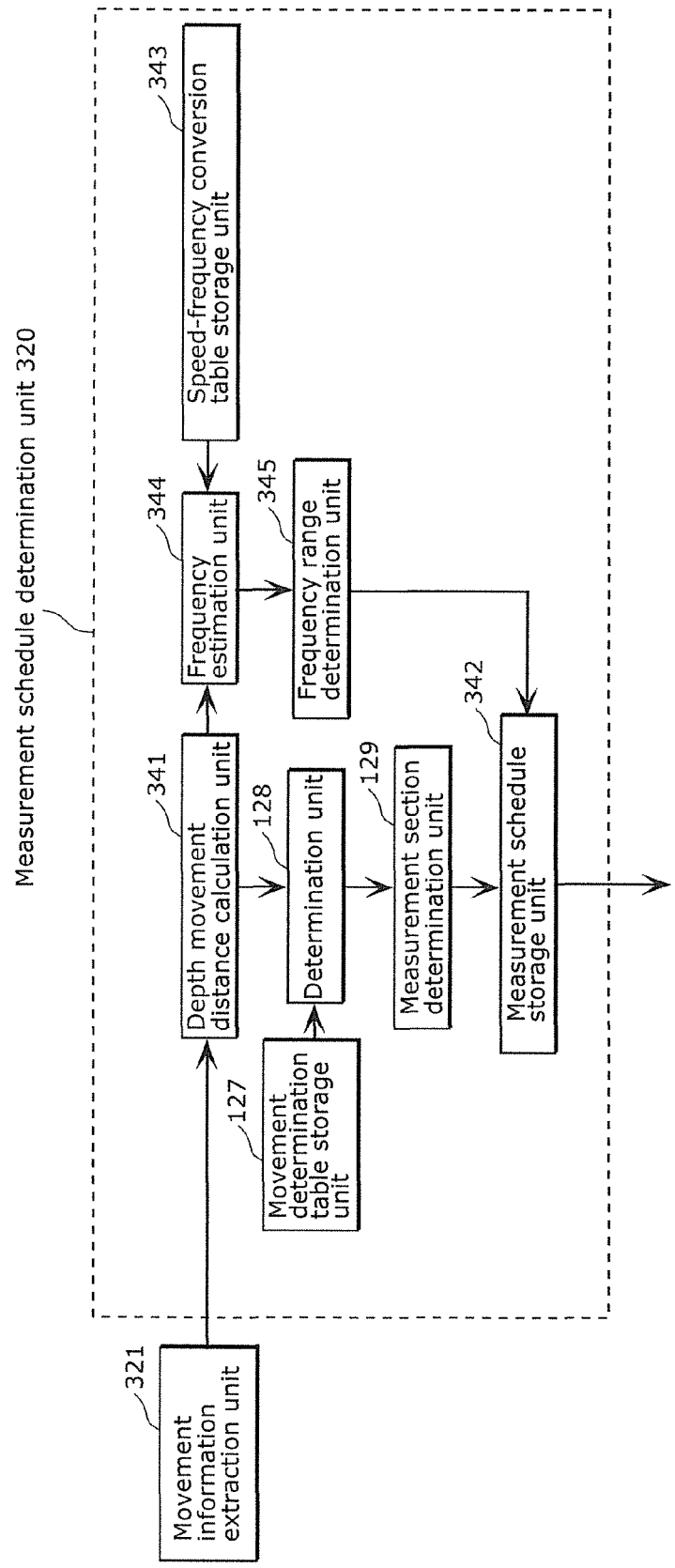
FIG. 23 is a diagram showing a detailed structure of a measurement schedule determination unit in Embodiment 3.

FIG. 23 is a diagram showing a detailed structure of the measurement schedule determination unit 320.

The measurement schedule determination unit 320 includes a depth movement distance calculation unit 341, the movement determination table storage unit 127, the determination unit 128, the measurement section determination unit 129, a speed-frequency conversion table storage unit 343, a frequency estimation unit 344, a frequency range determination unit 345, and a measurement schedule storage unit 342.

The depth movement distance calculation unit 341 calculates the movement distance of the object in the depth direction, from the movement information of the object. The movement information is stored as depth coordinates in the standard screen size, as shown in FIG. 22A. The depth movement distance calculation unit 341 stores the screen size of the display screen 102. Based on the ratio between the screen size of the display screen 102 and the standard size of the content stored in the movement information storage unit 311, the depth movement distance calculation unit 341 converts the three-dimensional coordinates of the object to the coordinate position in the screen size of the display screen 102, to calculate the movement distance in the depth direction.

The movement determination table storage unit 127 stores the determination criteria for switching between impedance measurement and electrooculogram measurement according to depth change information of objects as shown in FIG. 11.

The determination unit 128 determines the timing of switching between impedance measurement and electrooculogram measurement, based on the object movement information calculated by the depth movement distance calculation unit 341 and the determination criteria stored in the movement determination table storage unit 127.

The measurement section determination unit 129 determines the time section for measuring the electrode contact impedance and the time section for measuring the viewer's electrooculogram, based on the measurement switching timing.

The speed-frequency conversion table storage unit 343 stores correspondence information between the object speed and the frequency of the viewer's electrooculogram.

FIG. 24 is a diagram showing an example of information stored in the speed-frequency conversion table storage unit 343.

The speed-frequency conversion table storage unit 343 stores a movement speed and depth position of an object in video in the case where the video is displayed in the screen size of the display screen 102, and an electrooculogram frequency that is based on predicted eye movement when the viewer gazes at the object and that corresponds to the object speed and position.

The frequency estimation unit 344 estimates the frequency of the electrooculogram from the object movement information and depth position calculated by the depth movement distance calculation unit 341, with reference to the table stored in the speed-frequency conversion table storage unit 343.

The frequency range determination unit 345 determines the frequency range of the signal for impedance measurement, from the estimated frequency of the electrooculogram.

The measurement schedule storage unit 342 stores the measurement schedule on the time axis of the video content, and the frequency range of the impedance measurement signal for each frame calculated by the frequency range determination unit 345.

Figure 25:
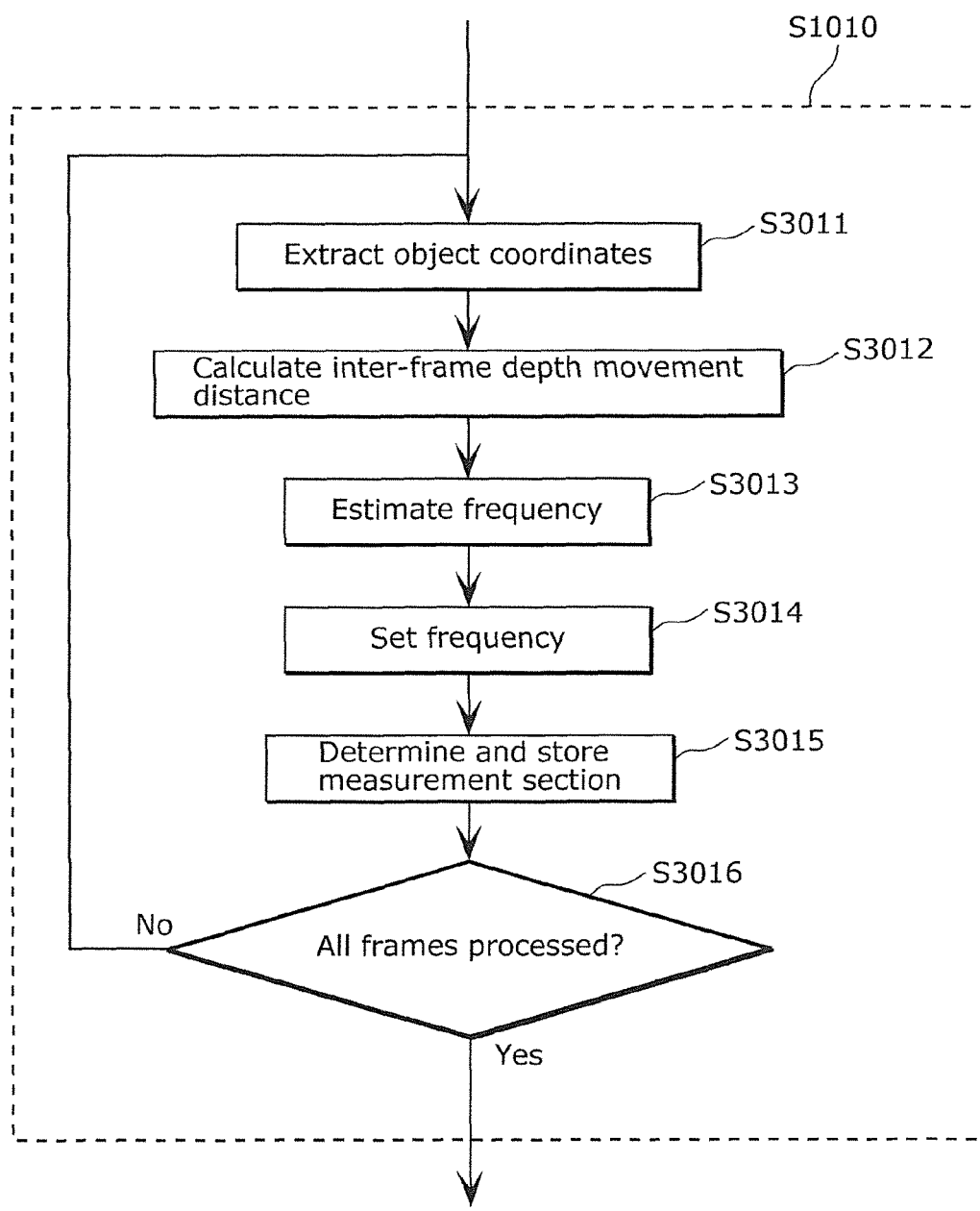
FIG. 25 is a flowchart showing an example of an operation of the measurement schedule determination unit in Embodiment 3.

The overall operation in Embodiment 3 is the same as that in Embodiment 1 shown in FIG. 13, and so its description is omitted. The detailed operation in Step S1010 in FIG. 13 is described below, with reference to FIG. 25. FIG. 25 is a flowchart showing the process on a frame basis.

(Step S3011)

The movement information extraction unit 321 extracts the coordinates of each object included in the frame, from the movement information stored in the movement information storage unit 311.

(Step S3012)

The depth movement distance calculation unit 341 calculates, from the coordinates of each object included in adjacent frames such as the current frame and the immediately following frame, the inter-frame movement distance of the object in the depth direction.

(Step S3013)

The frequency estimation unit 344 estimates the frequency of the electrooculogram corresponding to the depth movement distance between the adjacent frames calculated in Step S3012, i.e. the speed of the object in the depth direction, with reference to the table stored in the speed-frequency conversion table storage unit 343.

(Step S3014)

The frequency range determination unit 345 sets the value obtained by multiplying the frequency estimated in Step S3013 by 0.8 as the minimum value of the frequency range, and sets the maximum value of the frequency estimated in Step S3013 as the maximum value of the frequency range. The frequency range determination unit 345 thus determines the frequency range.

Though the above describes the case where the value obtained by multiplying the frequency by 0.8 is used as the minimum value in order to set the frequency range including the estimate of the electrooculogram frequency, the frequency range including the estimated frequency may be set by other methods.

(Step S3015)

The determination unit 128 determines, according to the depth movement of each object included in the frame, whether the frame is suitable for electrooculogram measurement or impedance measurement, with reference to the table stored in the movement determination table storage unit 127.

Whether or not the frame is suitable for electrooculogram measurement is determined based on the electrooculogram measurement suitability on a frame basis according to the movement of the object in the depth direction, as in Embodiment 1. As an alternative, a time section in which the frame is included and in which the depth movement speed or movement amount of an object in video is substantially equal to the depth movement speed or movement amount of an object in video in a time section upon viewing start which is suitable for electrooculogram measurement may be extracted, with the electrooculogram measurement section and the impedance measurement section being determined from the extracted time section. For example, "substantially equal" mentioned here means that the difference in object movement speed or object movement amount between the frame and the viewing start is within a predetermined range.

In the case of two-dimensional video, a time section in which the frame is included and in which the on-screen movement speed or movement amount of an object in video is substantially equal to the on-screen movement speed or movement amount of an object in video in a time section upon viewing start which is suitable for electrooculogram measurement may be extracted, with the electrooculogram measurement section and the impedance measurement section being determined from the extracted time section.

As another alternative, a time section in which the frame is included and in which the depth range of an object in video is substantially equal to the depth range of an object in video in a time section upon viewing start which is suitable for electrooculogram measurement may be extracted to determine the electrooculogram measurement section and the impedance measurement section. For example, "substantially equal" mentioned here means that the difference between the maximum depth of the object in the video in the time section including the frame and the maximum depth of the object in the video in the time section upon viewing start which is suitable for electrooculogram measurement and the difference between the minimum depth of the object in the video in the time section including the frame and the minimum depth of the object in the video in the time section upon viewing start which is suitable for electrooculogram measurement are both within a predetermined range.

The measurement section determination unit 129 sets consecutive frames suitable for electrooculogram measurement as the electrooculogram measurement section, sets a section other than the electrooculogram measurement section as the impedance measurement section, and stores the sections in the measurement schedule storage unit 342. The measurement schedule storage unit 342 stores, for each frame of the video, the measurement target during display of the frame. The measurement schedule storage unit 342 also extracts and stores, for the impedance measurement section, the frequency range of the signal for impedance measurement calculated in the frame of the electrooculogram measurement section closest in time to the frame, from among each frequency range of the signal for impedance measurement determined in Step S3014.

This makes it possible to measure the impedance corresponding to the frequency of the electrooculogram to be measured.

(Step S3016)

The depth movement distance calculation unit 341 determines whether or not all frames in the video content have been processed.

In the case of determining in Step S3014 that all frames have been processed, the eye fatigue measurement system 3 proceeds to Step S1020. In the case of determining in Step S3014 that all frames have not been processed, the eye fatigue measurement system 3 returns to Step S3011.

As shown in FIG. 20, in the frequency range in which the frequency of the electrooculogram is low, the impedance significantly differs depending on signal frequency. By sequentially setting the frequency range for impedance measurement according to the frequency of the electrooculogram estimated from the object movement in the video content as in this embodiment, the impedance for correcting the electrooculogram used in fatigue determination can be measured using the signal corresponding to the frequency of the electrooculogram which is the signal to be measured. This reduces the correction error caused by the difference in impedance depending on frequency. As a result, eye fatigue can be determined more accurately.

Here, the movement information storage unit 311, the movement information extraction unit 321, and the measurement schedule determination unit 320 are not essential structural elements. In detail, the frequency range of the signal used for impedance measurement, the time section for electrooculogram measurement, and the time section for impedance measurement, which are determined by the measurement schedule determination unit 320, may be included in the video content stored in the content information storage unit 101 in association with the time information of the content, as auxiliary information. In such a case, the measurement switching control unit 106 controls the switching between electrooculogram measurement and contact impedance measurement, with reference to the auxiliary information of the video content. Further, the impedance measurement unit 213C measures the impedance using the signal of the frequency range included in the auxiliary information of the video content.

Embodiment 4

Figure 26:
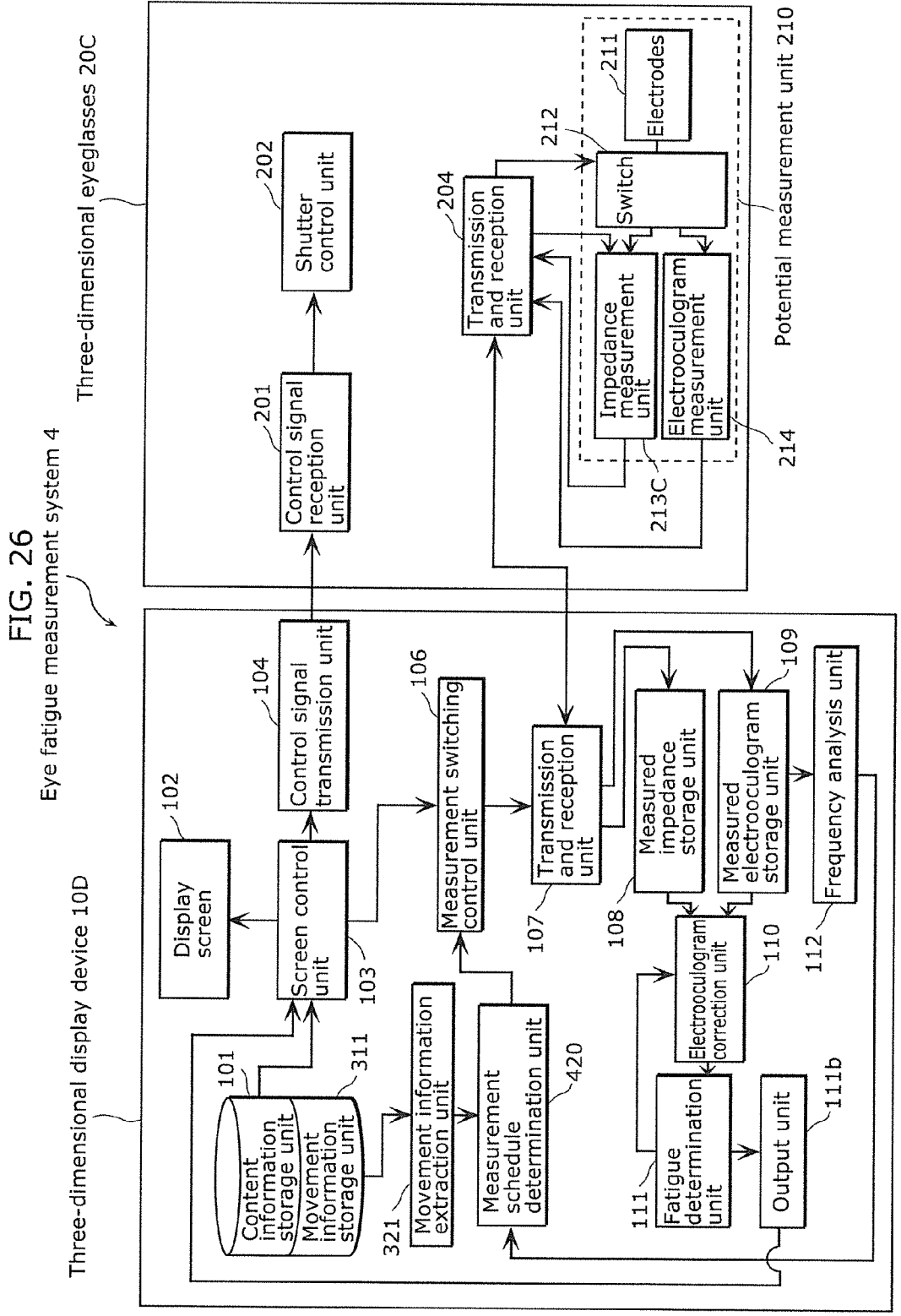
FIG. 26 is a block diagram showing an example of a structure of an eye fatigue measurement system in Embodiment 4.

FIG. 26 is a diagram showing a structure of an eye fatigue measurement system 4 in Embodiment 4.

Embodiment 4 combines Embodiments 2 and 3.

The eye fatigue measurement system 4 includes a three-dimensional display device 10D and the three-dimensional eyeglasses 20C.

The three-dimensional display device 10D includes a measurement schedule determination unit 420 instead of the measurement schedule determination unit 320 in the three-dimensional display device 10G shown in FIG. 21, and further includes the frequency analysis unit 112. The three-dimensional eyeglasses 20C have the same structure as the three-dimensional eyeglasses 20C shown in FIG. 17, and so their description is omitted. The same parts as those in FIG. 21 or 17 are given the same reference signs, and their description is omitted as appropriate.

The three-dimensional display device 10D includes the content information storage unit 101, the display screen 102, the screen control unit 103, the control signal transmission unit 104, the movement information storage unit 311, the movement information extraction unit 321, the measurement schedule determination unit 420, the measurement switching control unit 106, the transmission and reception unit 107, the measured impedance storage unit 108, the measured electrooculogram storage unit 109, the electrooculogram correction unit 110, the fatigue determination unit 111, the output unit 111b, and the frequency analysis unit 112.

The measurement schedule determination unit 420 determines the time section for electrooculogram measurement and the time section for impedance measurement and also determines the frequency range of the signal used for impedance measurement, based on the electrooculogram frequency estimated from the object speed in the video content and the frequency analysis result of the measured electrooculogram.

Figure 27:
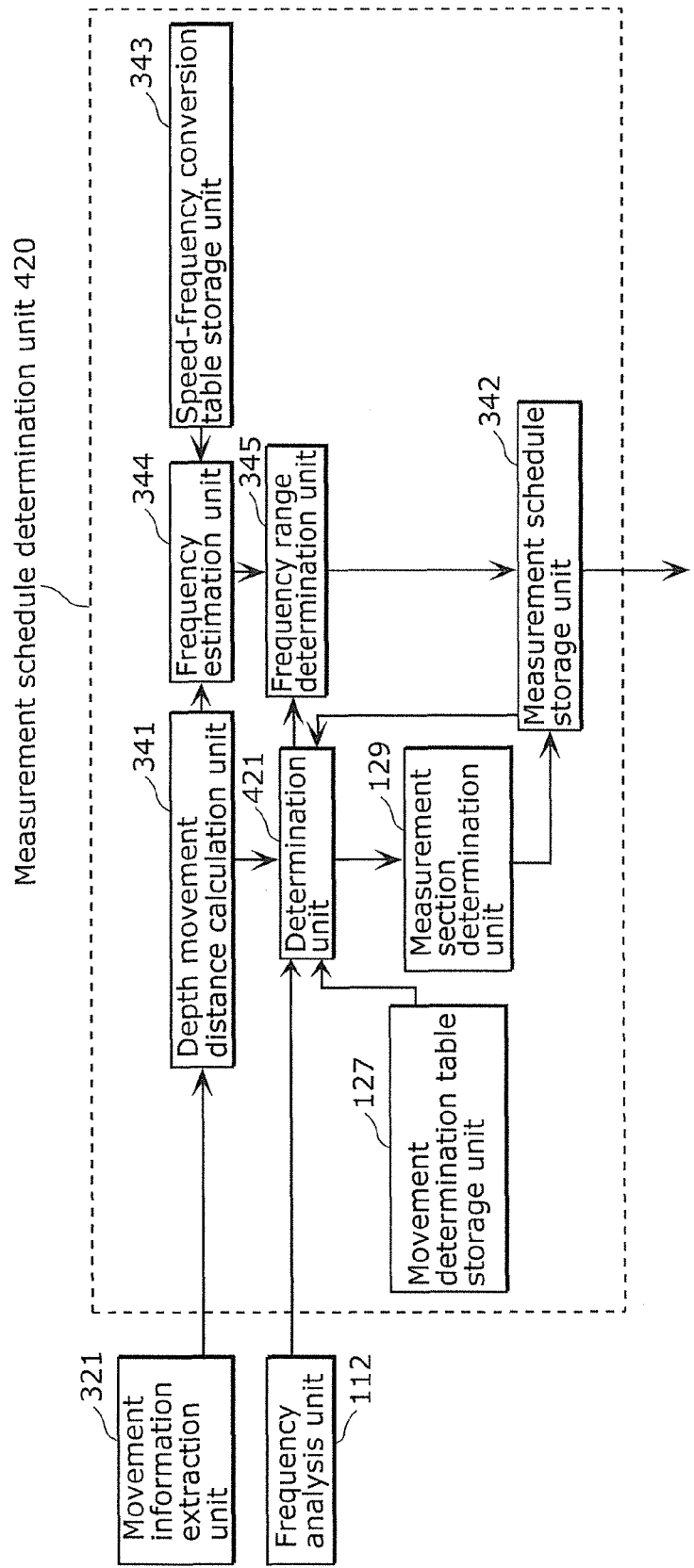
FIG. 27 is a diagram showing a detailed structure of a measurement schedule determination unit in Embodiment 4.

FIG. 27 is a diagram showing a detailed structure of the measurement schedule determination unit 420. The structure shown in FIG. 27 is the same as the structure shown in FIG. 23, except that the determination unit 128 is replaced with a determination unit 421. The same parts as those in FIG. 23 are given the same reference signs, and their description is omitted as appropriate. The measurement schedule determination unit 420 includes the depth movement distance calculation unit 341, the movement determination table storage unit 127, the determination unit 421, the measurement section determination unit 129, the speed-frequency conversion table storage unit 343, the frequency estimation unit 344, the frequency range determination unit 345, and the measurement schedule storage unit 342.

The determination unit 421 determines the timing of switching between impedance measurement and electrooculogram measurement based on the object movement information, and modifies the timing of switching between impedance measurement and electrooculogram measurement based on the frequency analysis result of the measured electrooculogram.

Figure 28:
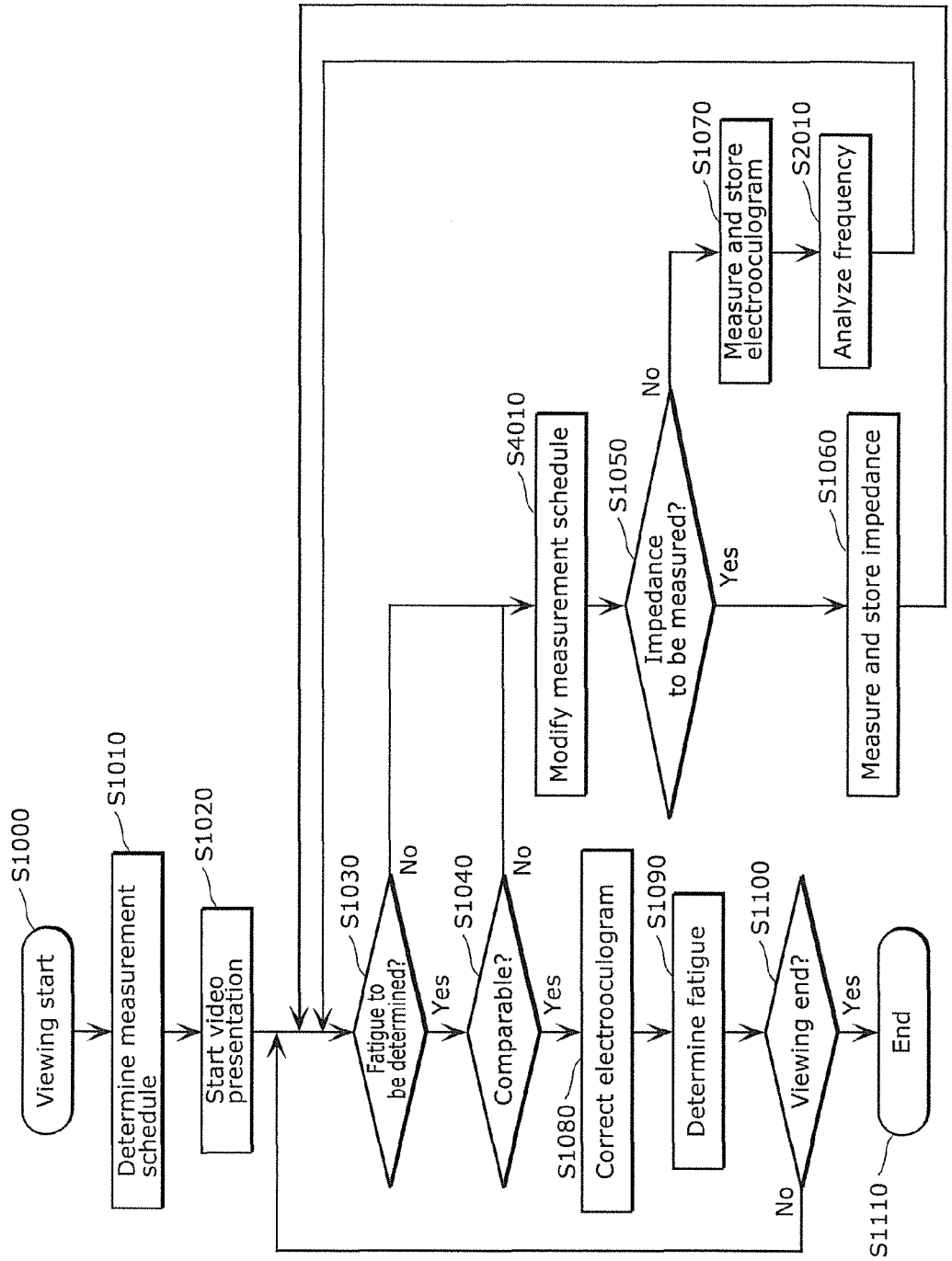
FIG. 28 is a flowchart showing an example of an operation of the eye fatigue measurement system in Embodiment 4.

FIG. 28 is a flowchart showing an operation of the eye fatigue measurement system 4 in Embodiment 4. The flowchart in FIG. 28 includes Steps S2010 and S4010 in addition to the flowchart in FIG. 13, where the other steps are the same as those in FIG. 13. The procedure performed by the eye fatigue measurement system 4 is described below with reference to FIG. 28, while omitting the description of the same operations as those in FIG. 13 as appropriate.

First, the viewer presses the power switch (not shown), to turn on the three-dimensional display device 10D and the three-dimensional eyeglasses 20C. The eye fatigue measurement system 4 thus starts the operation (Step S1000). The measurement schedule determination unit 120 determines, for the content stored in the content information storage unit 101, each time section for impedance measurement and each time section for electrooculogram measurement on the time axis of the content (Step S1010). The details of Step S1010 are the same as those of Step S1010 in Embodiment 3. Next, the screen control unit 103 outputs the video of the content stored in the content information storage unit 101, to the display screen 102. At the same time, the screen control unit 103 outputs the control signal for controlling the shutter timing of the three-dimensional eyeglasses 20C, to the control signal transmission unit 104. The screen control unit 103 thus starts the display of the stereoscopic video (Step S1020). The fatigue determination unit 111 determines whether or not the current time is the predetermined fatigue determination time (Step S1030). In the case of determining in Step S1030 that the current time is the fatigue determination time, the eye fatigue measurement system 4 proceeds to Step S1040. In the case of determining in Step S1030 that the current time is not the fatigue determination time, the eye fatigue measurement system 4 proceeds to Step S4010. In Step S1040, the electrooculogram correction unit 110 checks whether or not measurement data sufficient for fatigue determination is stored in the measured impedance storage unit 108 and the measured electrooculogram storage unit 109 (Step S1040). In the case of determining in Step S1040 that data stored in any of the measured impedance storage unit 108 and the measured electrooculogram storage unit 109 is insufficient for fatigue determination, the eye fatigue measurement system 4 proceeds to Step S4010. In the case of determining in Step S1040 that data sufficient for fatigue determination is stored in the measured impedance storage unit 108 and the measured electrooculogram storage unit 109, the eye fatigue measurement system 4 proceeds to Step S1080.

In Step S4010, the measurement schedule determination unit 420 compares the frequency range of the impedance measurement signal determined in Step S1010 and stored in the measurement schedule storage unit 342 and the frequency of the electrooculogram analyzed by the frequency analysis unit 112, and modifies the measurement schedule corresponding to a predetermined period, such as 10 minutes, from the current time (Step S4010).

Figure 29:
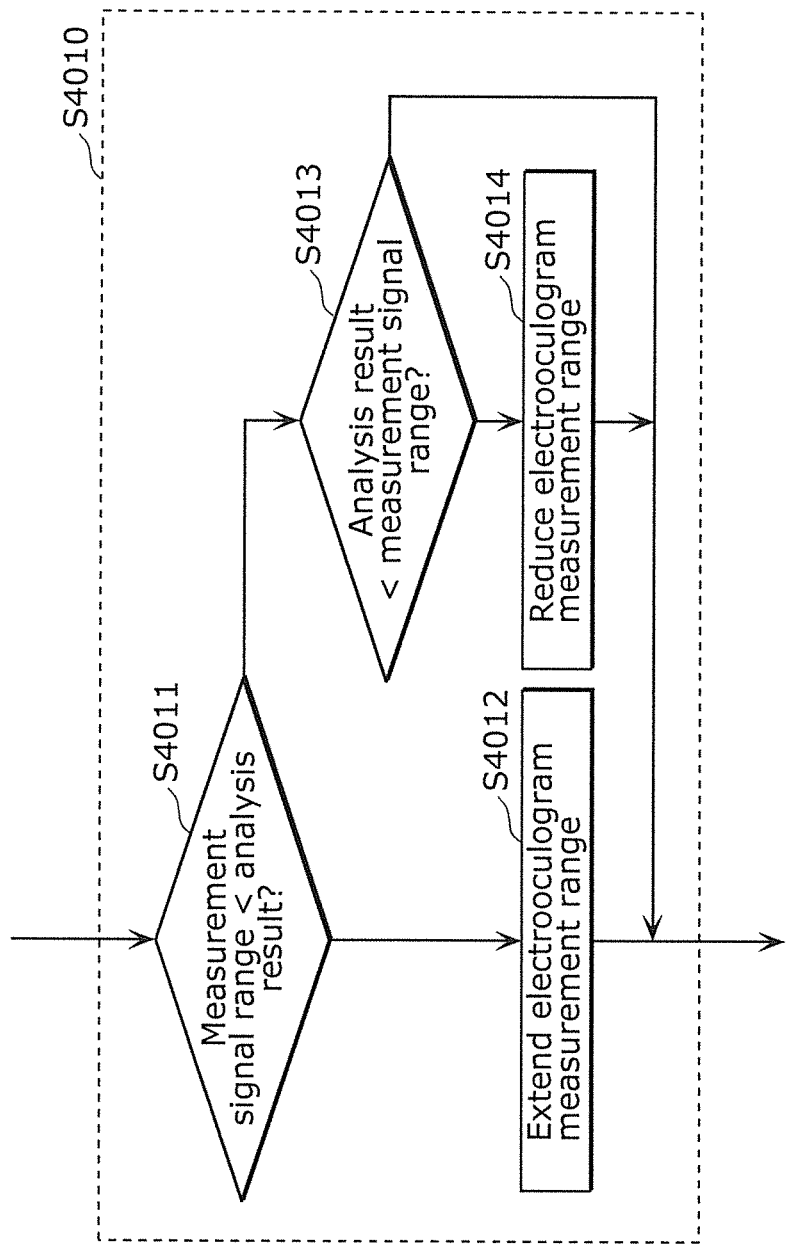
FIG. 29 is a detailed flowchart showing a measurement schedule modification process (Step S4010 in FIG. 28) in Embodiment 4.

FIG. 29 is a flowchart showing Step S4010 in detail.

The determination unit 421 compares the frequency range of the impedance measurement signal and the frequency of the electrooculogram (Step S4011). In the case where the frequency range of the impedance measurement signal is lower than the analyzed frequency of the electrooculogram in Step S4011, the measurement section determination unit 129 extends the electrooculogram measurement section (Step S4012). For example, in the case of video of 60 frames, i.e. video of 60 Hz, the measurement section determination unit 129 extends the electrooculogram measurement section by 1 second. In the case where the frequency range of the impedance measurement signal is higher than the analyzed frequency of the electrooculogram or the analyzed frequency of the electrooculogram is included in the frequency range of the impedance measurement signal in Step S4011, the determination unit 421 determines whether or not the analyzed frequency of the electrooculogram is lower than the frequency of the impedance measurement signal (Step S4013). In the case where the analyzed frequency of the electrooculogram is lower than the frequency of the impedance measurement signal in Step S4013, the measurement section determination unit 129 reduces the electrooculogram measurement section (Step S4014). For example, in the case of video of 60 frames, i.e. video of 60 Hz, the measurement section determination unit 129 reduces the electrooculogram measurement section by 1 second. In the case where the analyzed frequency of the electrooculogram is included in the frequency range of the impedance measurement signal in Step S4013, the measurement section is not modified.

In Step S1050, the measurement switching control unit 106 checks whether or not the currently displayed video is video in a time section for impedance measurement (Step S1050). In the case where the currently displayed video is video in the time section for impedance measurement, the measurement switching control unit 106 generates a control signal for connecting the switch 212 to the impedance measurement unit 213C, and outputs the control signal to the transmission and reception unit 107 in the three-dimensional display device 10D. The transmission and reception unit 107 transmits the control signal. The transmission and reception unit 204 in the three-dimensional eyeglasses 20C receives the control signal from the transmission and reception unit 107, and connects the switch 212 to the impedance measurement unit 213C. As a result, the impedance measurement unit 213C enters a state of being capable of measuring the contact impedance of each electrode 211. The impedance measurement unit 213C sets the frequency of the oscillator 301C to the measurement frequency range stored in the measurement schedule storage unit 342. The oscillator 301C outputs the measurement signal of predetermined voltage and current to the reference electrode of the electrodes 211, according to the frequency range set in the oscillator 301C. The voltage measurement unit 302 measures the voltage obtained from the electrode 211 other than the reference electrode. The impedance calculation unit 303 calculates the impedance at the frequency of the signal output from the oscillator 301C, from the signal output from the oscillator 301C and the voltage obtained from the electrode 211. The calculated impedance is stored in the measured impedance storage unit 108 (Step S1060).

In the case where the currently displayed video is not video in the time section for impedance measurement in Step S1050, the measurement switching control unit 106 generates a control signal for connecting the switch 212 to the electrooculogram measurement unit 214, and outputs the control signal to the transmission and reception unit 107 in the three-dimensional display device 10D. The transmission and reception unit 107 transmits the control signal received from the measurement switching control unit 106, to the three-dimensional eyeglasses 20C. The transmission and reception unit 204 in the three-dimensional eyeglasses 20C receives the control signal from the transmission and reception unit 107, and connects the switch 212 to the electrooculogram measurement unit 214. As a result, the electrooculogram measurement unit 214 enters a state of being capable of measuring the electrooculogram using the electrodes 211, and outputs data of the measured electrooculogram to the transmission and reception unit 204 in the three-dimensional eyeglasses 20C. The transmission and reception unit 204 transmits the data received from the electrooculogram measurement unit 214, to the three-dimensional display device 10D. The transmission and reception unit 107 in the three-dimensional display device 10D receives the data from the transmission and reception unit 204, and stores the data in the measured electrooculogram storage unit 109 (Step S1070). The frequency analysis unit 112 analyzes the frequency of the electrooculogram data stored in the measured electrooculogram storage unit 109 (Step S2010).

After Step S1060 or S2010, the eye fatigue measurement system 4 returns to Step S1030.

In Step S1080, the electrooculogram correction unit 110 extracts the electrooculogram measured in the time closest to the video display start time, from the measured electrooculogram storage unit 109. The electrooculogram correction unit 110 also extracts the impedances before and after the measurement time section of the extracted electrooculogram, from the measured impedance storage unit 108. The electrooculogram correction unit 110 corrects the extracted electrooculogram using the impedances before and after the electrooculogram measurement time section (Step S1080), and outputs the corrected electrooculogram to the fatigue determination unit 111. The fatigue determination unit 111 determines, with regard to the electrooculogram measured using the same electrode or the same electrode set and corrected in Step S1080, the viewer's fatigue based on the ratio between the average amplitude of the electrooculogram measured in the time closest to the video display start time and the average amplitude of the electrooculogram measured most recently (Step S1090).

The screen control unit 103 determines whether or not input for turning off the three-dimensional display device 10D or ending the viewing is made by the viewer by, for example, pressing the power switch (not shown), via the power switch or other input means (not shown) (Step S1100). In the case where input for turning off the three-dimensional display device 10D or ending the viewing is made in Step S1100, the eye fatigue measurement system 4 ends the operation (Step S1110). In the case where there is no input for turning off the three-dimensional display device 10D or ending the viewing in Step S1100, the eye fatigue measurement system 4 returns to Step S1030. By repeatedly performing Steps S1030 to S1100, the eye fatigue measurement system 4 sequentially determines the viewer's fatigue during video display.

Thus, the frequency range for impedance measurement is sequentially set according to the frequency obtained by modifying the frequency of the electrooculogram estimated from the object movement in the video content using the frequency of the measured electrooculogram. By doing so, the impedance for correcting the electrooculogram used in fatigue determination can be measured at the frequency of the electrooculogram which is the signal to be measured. This reduces the correction error caused by the difference in impedance depending on frequency. As a result, eye fatigue can be determined more accurately.

Though the above describes the case where the measurement schedule determination unit 420 sets, as the electrooculogram measurement section, the section in which the frequency of the electrooculogram estimated by the frequency estimation unit 344 matches the frequency of the electrooculogram analyzed by the frequency analysis unit 112, the process is not limited to this. The measurement schedule determination unit 420 may further compare the frequency estimated by the frequency estimation unit 344 and the frequency of the actually measured electrooculogram, and modify the table stored in the speed-frequency conversion table storage unit 343 to optimize the correspondence between the object movement in the video content and the frequency of the viewer's electrooculogram.

Variation 1

As shown in FIG. 1, the contact between the electrode and the skin is unstable and so the impedance fluctuates significantly immediately after putting on the eyeglasses. For example, when the viewer, upon putting the three-dimensional eyeglasses 20 on his or her skin, moves the three-dimensional eyeglasses 20 to adjust its position, the impedance fluctuates significantly. Therefore, in the period in which the viewer is putting on the three-dimensional eyeglasses 20, it is difficult to correct the electrooculogram using the impedance with sufficient accuracy.

On the other hand, the change in impedance due to physiological phenomena such as sweating gradually decreases after putting on the three-dimensional eyeglasses 20. In this case, it is possible to correct the electrooculogram using the impedance with sufficient accuracy.

In this variation, when the change in impedance per unit time falls below a predetermined value, the eye fatigue measurement system recognizes that the manipulation of the eyeglasses by the viewer ends, and starts the electrooculogram correction.

Figure 30:
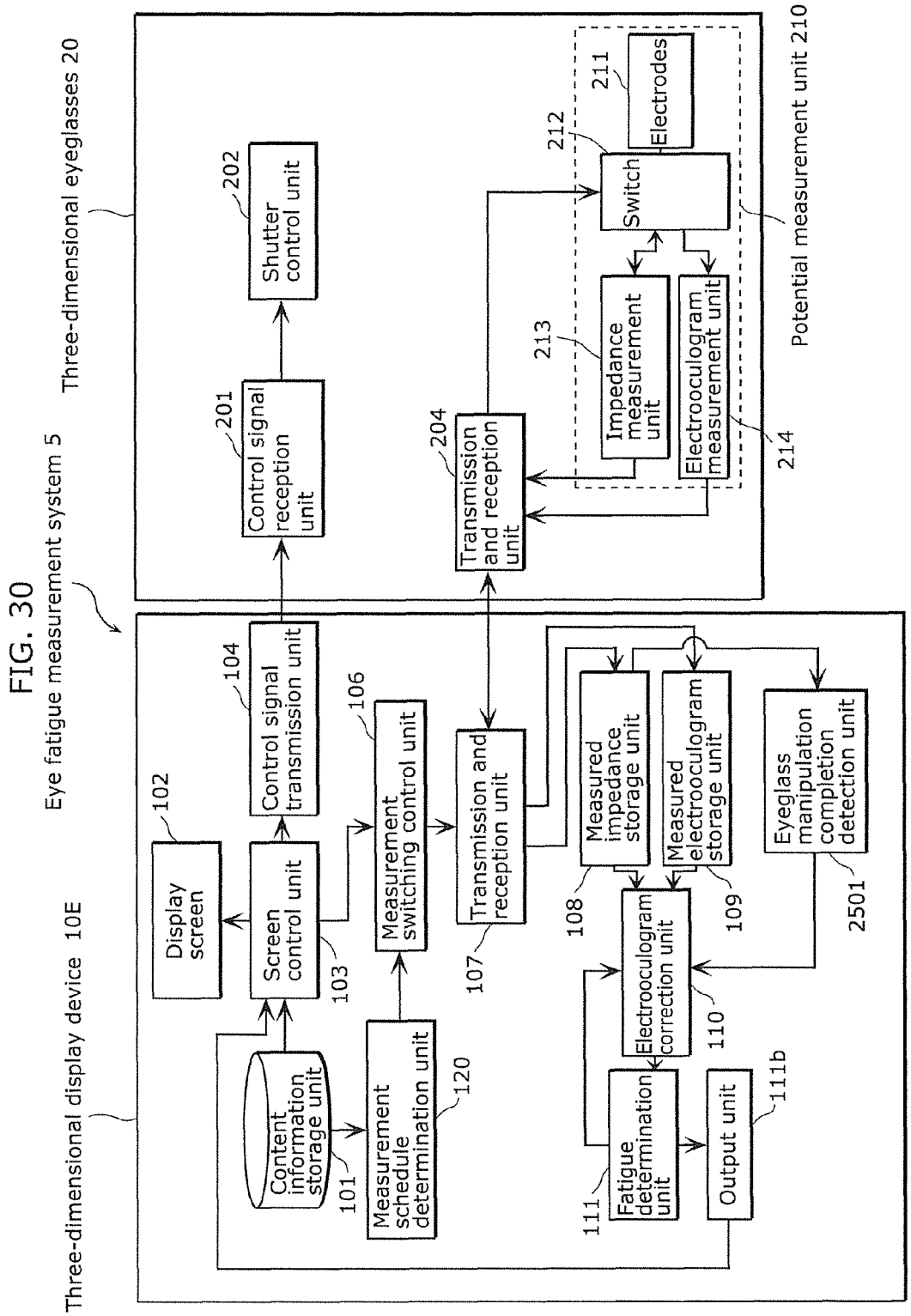
FIG. 30 is a block diagram showing an example of a structure of an eye fatigue measurement system in Variation 1 of Embodiment 1.

FIG. 30 is a diagram showing a structure of the eye fatigue measurement system in this variation. An eye fatigue measurement system 5 includes a three-dimensional display device 10E and the three-dimensional eyeglasses 20.

The three-dimensional display device 10E includes an eyeglass manipulation completion detection unit 2501 in addition to the structure of the three-dimensional display device 10 in Embodiment 1 shown in FIG. 3.

The eyeglass manipulation completion detection unit 2501 detects whether or not the manipulation of the eyeglasses by the viewer has completed, from time series data of the impedance.

An operation in this variation is briefly described below.

Figure 31:
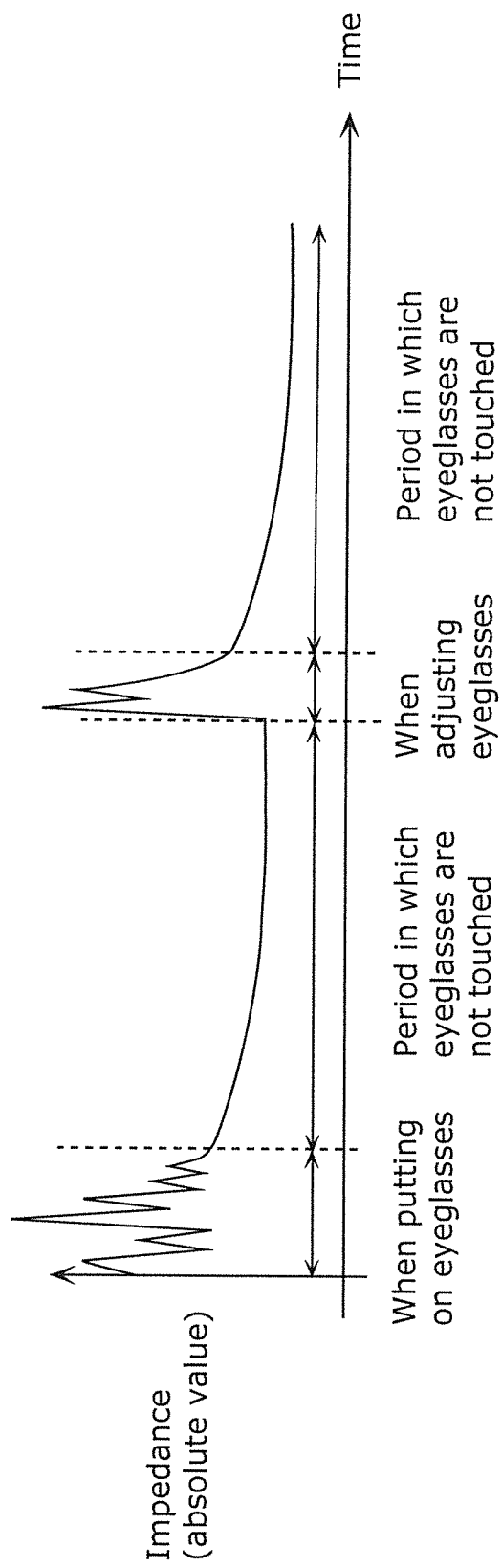
FIG. 31 is a schematic diagram showing relationships between the contact impedance of an electrode changing with time and the eyeglass wearing operation.

The measured impedance storage unit 108 stores the time series data of the impedance measured by the viewer's eyeglasses. For example, suppose data is obtained with intervals of 500 ms at a predetermined frequency, as shown in FIG. 31. For several seconds after the viewer puts on the three-dimensional eyeglasses 20, the viewer is touching the eyeglasses, so that the impedance is unstable due to the change in contact part between the skin and the electrode. After the viewer completes putting on the eyeglasses and the contact part between the skin and the electrode becomes stable, on the other hand, the impedance tends to decease gradually due to the viewer sweating or the like. If the viewer directly touches the eyeglasses and moves the position of the eyeglasses in order to adjust the eyeglasses, the impedance increases again and becomes unstable.

Accordingly, whether the viewer is adjusting the eyeglasses to change the physical position of the eyeglasses or the viewer is not touching the eyeglasses can be determined from the change in impedance.

In detail, in the case where the change in impedance in 1 second is greater than or equal to a predetermined value such as 100 k$\Omega$, it is determined that the viewer is touching the eyeglasses. In the case where the change in impedance in 1 second is less than a predetermined value such as 100 k$\Omega$, it is determined that the viewer is not touching the eyeglasses. For example, the change in impedance may be expressed by the difference between the maximum impedance and the minimum impedance in a predetermined time section, or by the variance of the impedance in a predetermined time section.

When the impedance changes significantly, it is difficult to correct the electrooculogram accurately using such an impedance value. Accordingly, the electrooculogram is corrected only in the state where the viewer is not touching the eyeglasses.

As a result of the above operation, the state where the viewer has completed putting on the eyeglasses can be recognized based on the impedance, and the electrooculogram correction can be started from this state.

Though this variation describes the case where whether or not the viewer has completed putting on the eyeglasses is determined, it is also possible to detect the state of contact between the skin and the electrode from the impedance.

For example, in the case where the skin and the electrode are not in contact, an impedance value greater than or equal to a predetermined value such as 1 M$\Omega$ is measured. The electrooculogram correction may be suppressed in such a case.

Variation 2

In Embodiment 1, the impedance is measured at each electrode, and the electrooculogram is corrected using the measured impedance. In Variation 2, the impedance of each electrode is further subjected to comparison, to enable the state of the eyeglasses to be estimated from the contact state of the electrodes on the viewer.

In particular, the impedance between the skin and the electrode can be reduced by pressing the electrode. Hence, which part of the eyeglasses needs to be pressed can be determined from the electrode contact state. This makes it possible to provide information, such as the viewer needs to press the right temple of the eyeglasses downward or the viewer needs to press the bridge of the eyeglasses on the nose, through a television screen or the like.

Figure 32:
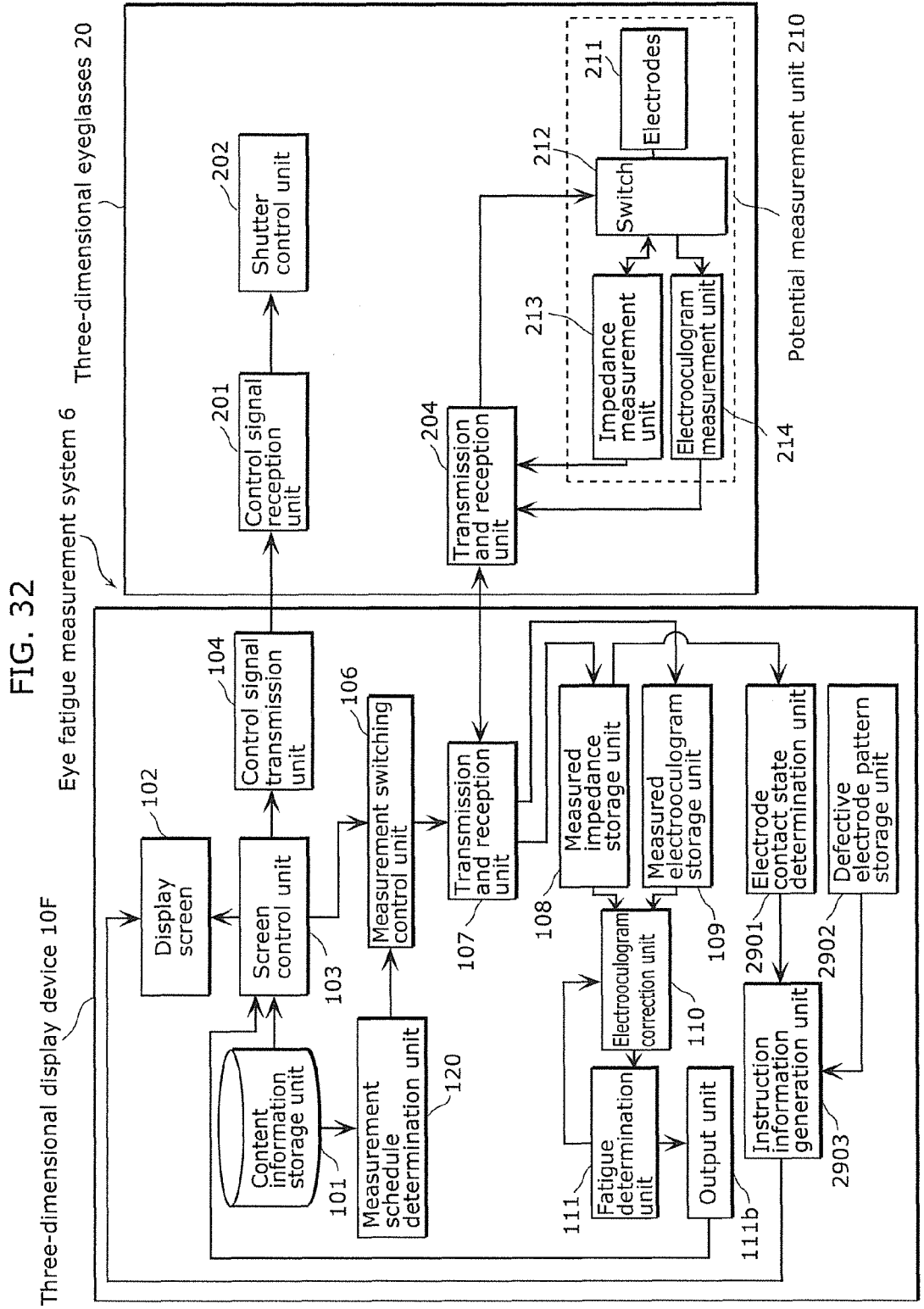
FIG. 32 is a block diagram showing an example of a structure of an eye fatigue measurement system in Variation 2 of Embodiment 1.

FIG. 32 is a diagram showing a structure in this variation. An eye fatigue measurement system 6 includes a three-dimensional display device 10F and the three-dimensional eyeglasses 20.

The three-dimensional display device 10F includes an electrode contact state determination unit 2901, a defective electrode pattern storage unit 2902, and an instruction information generation unit 2903, in addition to the structure of the three-dimensional display device 10 in Embodiment 1 shown in FIG. 3.

The electrode contact state determination unit 2901 estimates the contact state of each electrode with the skin from the time series information of the impedance stored in the measured impedance storage unit 108.

The defective electrode pattern storage unit 2902 stores each defective electrode combination pattern when putting on the eyeglasses and an eyeglass position adjustment instruction corresponding to the combination pattern, in association with each other.

The instruction information generation unit 2903 generates an adjustment instruction to the viewer, from the contact states of the plurality of electrodes detected by the electrode contact state determination unit 2901 and the defective electrode patterns stored in the defective electrode pattern storage unit 2902.

A detailed operation is described below.

The electrode contact state determination unit 2901 determines the contact state of each electrode mounted on the eyeglasses. For example, eight electrodes are mounted on the eyeglasses shown in FIG. 4A. In the case where the impedance measured at any of the electrodes is greater than or equal to a predetermined value such as 500 kΩ, the contact state of the electrode with the skin is not good.

The defective electrode pattern storage unit 2902 stores, for each combination of electrodes with poor contact state, information of which part of the eyeglasses a load needs to be applied to in which direction, in order to improve the contact state. FIG. 33A is a diagram showing an example of such information. For instance, in the case where the contact states of the electrodes a and g are not good as in a pattern 1, there is a possibility that the right temple of the eyeglasses is loose. Accordingly, an instruction (instruction 1) to apply a downward load to the right temple as shown in FIG. 33B is notified to the viewer. In the case where the contact states of the electrodes b and c are not good as in a pattern 2, the electrodes b and c need to be in contact with the viewer's forehead. Accordingly, an instruction (instruction 2) to apply a load from the front of the eyeglasses as shown in FIG. 33B is notified to the viewer. The defective electrode pattern storage unit 2902 thus stores the correspondence table for instructing the viewer to apply a load to which part of the eyeglasses in which direction when defective electrodes are detected.

Figure 34:
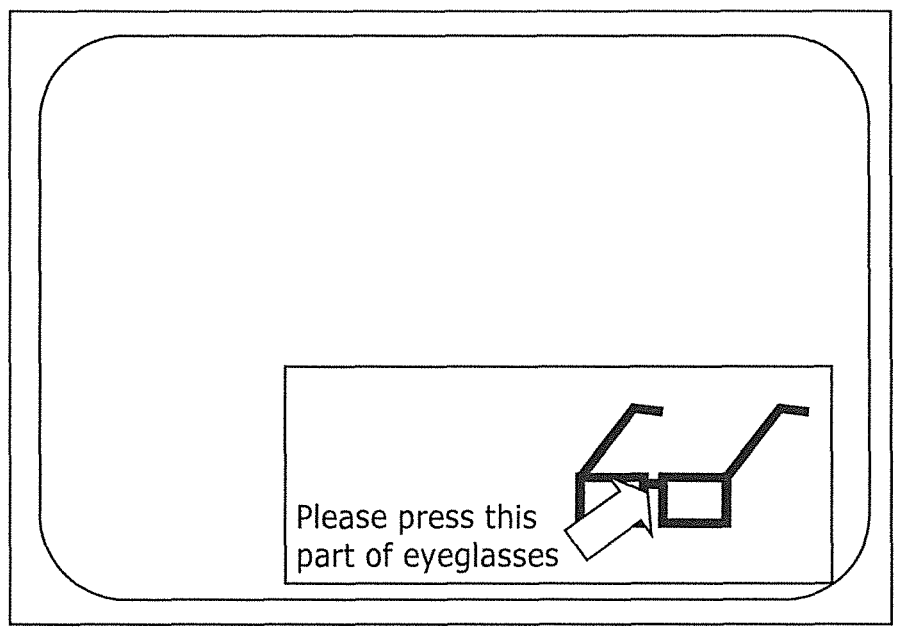
FIG. 34 is a diagram showing an example of a display screen for displaying an instruction to a viewer in Variation 2 of Embodiment 1.

The instruction information generation unit 2903 obtains the defective electrode information detected by the electrode contact state determination unit 2901, selects an instruction to the viewer corresponding to the defective electrode pattern stored in the defective electrode pattern storage unit 2902, and generates information to be displayed on the display screen 102. For example, in the case where the electrode contact state determination unit 2901 detects the electrodes b and c as defective electrodes, the instruction information generation unit 2903 generates image information of the instruction 2. The instruction information generation unit 2903 then displays information as shown in FIG. 34, on the display screen 102.

Each of the structural elements in each of the above-described embodiments may be configured in the form of an exclusive hardware product, or may be realized by executing a software program suitable for the structural element. Each of the structural elements may be realized by means of a program executing unit, such as a CPU and a processor, reading and executing the software program recorded on a recording medium such as a hard disk or a semiconductor memory. Here, the software program for realizing the eye fatigue determination apparatus according to each of the embodiments is a program described below.

The program causes a computer to execute an eye fatigue determination method including: obtaining an electrooculogram indicating a potential measured using an electrode placed near an eye of a viewer who is viewing stereoscopic video content, the electrooculogram being measured in predetermined time sections during display of the video content; obtaining an impedance between the electrode and the viewer's skin at a position where the electrode is placed, the impedance being measured in the predetermined time sections; correcting the electrooculogram obtained in the obtaining of the electrooculogram, based on the impedance obtained in the obtaining of the impedance; and determining fatigue of the viewer's eye, based on the electrooculogram corrected in the correcting.

The herein disclosed subject matter is to be considered descriptive and illustrative only, and the appended Claims are of a scope intended to cover and encompass not only the particular embodiments disclosed, but also equivalent structures, methods, and/or uses.

For example, though the above describes the case where the viewer wears the eyeglasses, the viewer may wear a head-mounted display including a potential measurement unit instead of the eyeglasses.

INDUSTRIAL APPLICABILITY

The eye fatigue determination apparatus according to one or more exemplary embodiments disclosed herein is widely applicable to a video display system in which stereoscopic video is viewed using three-dimensional eyeglasses, and is useful for displaying stereoscopic video on movie screens, TVs, and computer display screens. The eye fatigue determination apparatus according to one or more exemplary embodiments disclosed herein is applicable not only to content viewing but also to image display devices in medical equipment such as diagnostic imaging devices and endoscopes, games and training systems such as simulated vehicle ride and surgery, and the like. The eye fatigue determination apparatus according to one or more exemplary embodiments disclosed herein is also applicable not only to stereoscopic video viewing but also to display of two-dimensional video. In detail, a viewer's fatigue when viewing two-dimensional video can be determined by attaching a potential measurement unit to eyeglasses that block light of a specific wavelength such as blue light for eye fatigue prevention.

The invention claimed is:

1. An eye fatigue determination apparatus comprising:
a video content obtainment unit configured to obtain video content;
a measurement schedule determination unit configured to, from the video content obtained by the video content obtainment unit, determine an electrooculogram measurement time section in each of a first time section and a second time section during display of the video content, and determine an impedance measurement time section in each of the first time section and the second time section based on the determined electrooculogram measurement time section, the electrooculogram measurement time section being a time section for measuring an electrooculogram, and the impedance measurement time section being a time section for measuring an impedance;
an electrooculogram obtainment unit configured to obtain the electrooculogram indicating a potential measured using an electrode placed near an eye of a viewer who is viewing the video content, the electrooculogram being measured in each of the first time section and the second time section which are determined by the measurement schedule determination unit;
an impedance obtainment unit configured to obtain the impedance between the electrode and the viewer's skin at a position where the electrode is placed, the impedance being measured in each of the first time section and the second time section which are determined by the measurement schedule determination unit;
an electrooculogram correction unit configured to correct the electrooculogram measured in the first time section based on the impedance measured in the first time section, and correct the electrooculogram measured in the second time section based on the impedance measured in the second time section; and
a fatigue determination unit configured to determine fatigue of the viewer's eye, by comparing the electrooculogram measured in the first time section and corrected by the electrooculogram correction unit and the electrooculogram measured in the second time section and corrected by the electrooculogram correction unit,
wherein the measurement schedule determination unit is configured to determine the first time section and the second time section according to a movement amount of an object in the video content, the movement amount of the object in the video content included in the first time section and the movement amount of the object in the video content included in the second time section being equal to each other.

2. The eye fatigue determination apparatus according to claim 1,
wherein the measurement schedule determination unit is configured to, in the case where the video content is stereoscopic video content, determine the first time section and the second time section according to the movement amount of the object in the video content in a depth direction, the movement amount of the object in the video content in the depth direction included in the first time section and the movement amount of the object in the video content in the depth direction included in the second time section being equal to each other.

3. The eye fatigue determination apparatus according to claim 1,
wherein the measurement schedule determination unit is configured to, in the case where the video content is stereoscopic video content, determine the first time section and the second time section according to a distance of an object in the video content in a depth direction, a range of the distance of the object in the video content in the depth direction included in the first time section and a range of the distance of the object in the video content in the depth direction included in the second time section being equal to each other.

4. An eye fatigue determination apparatus comprising:
a video content obtainment unit configured to obtain video content;
a measurement schedule determination unit configured to, from the video content obtained by the video content obtainment unit, determine an electrooculogram measurement time section in each of a first time section and a second time section during display of the video content, and determine an impedance measurement time section in each of the first time section and the second time section based on the determined electrooculogram measurement time section, the electrooculogram measurement time section being a time section for measuring an electrooculogram, and the impedance measurement time section being a time section for measuring an impedance;
an electrooculogram obtainment unit configured to obtain the electrooculogram indicating a potential measured using an electrode placed near an eye of a viewer who is viewing the video content, the electrooculogram being measured in each of the first time section and the second time section which are determined by the measurement schedule determination unit;
an impedance obtainment unit configured to obtain the impedance between the electrode and the viewer's skin at a position where the electrode is placed, the impedance being measured in each of the first time section and the second time section which are determined by the measurement schedule determination unit;
an electrooculogram correction unit configured to correct the electrooculogram measured in the first time section based on the impedance measured in the first time section, and correct the electrooculogram measured in the second time section based on the impedance measured in the second time section; and
a fatigue determination unit configured to determine fatigue of the viewer's eye, by comparing the electrooculogram measured in the first time section and corrected by the electrooculogram correction unit and the electrooculogram measured in the second time section and corrected by the electrooculogram correction unit,
wherein the measurement schedule determination unit is configured to determine the electrooculogram measurement time section to be longer in the case where a movement duration of an object in the video content in a depth direction is longer and a movement speed of the object in the depth direction is higher.

5. An eye fatigue determination apparatus comprising:
a video content obtainment unit configured to obtain video content;
a measurement schedule determination unit configured to, from the video content obtained by the video content obtainment unit, determine an electrooculogram measurement time section in each of a first time section and a second time section during display of the video content, and determine an impedance measurement time section in each of the first time section and the second time section based on the determined electrooculogram measurement time section, the electrooculogram measurement time section being a time section for measuring an electrooculogram, and the impedance measurement time section being a time section for measuring an impedance;

an electrooculogram obtainment unit configured to obtain the electrooculogram indicating a potential measured using an electrode placed near an eye of a viewer who is viewing the video content, the electrooculogram being measured in each of the first time section and the second time section which are determined by the measurement schedule determination unit;

an impedance obtainment unit configured to obtain the impedance between the electrode and the viewer's skin at a position where the electrode is placed, the impedance being measured in each of the first time section and the second time section which are determined by the measurement schedule determination unit;

an electrooculogram correction unit configured to correct the electrooculogram measured in the first time section based on the impedance measured in the first time section, and correct the electrooculogram measured in the second time section based on the impedance measured in the second time section; and a fatigue determination unit configured to determine fatigue of the viewer's eye, by comparing the electrooculogram measured in the first time section and corrected by the electrooculogram correction unit and the electrooculogram measured in the second time section and corrected by the electrooculogram correction unit, wherein the measurement schedule determination unit is configured to determine the electrooculogram measurement time section to be longer in the case where a reproduction speed of the video content obtained by the video content obtainment unit is higher.

6. The eye fatigue determination apparatus according to claim 1, further comprising:

an impedance measurement unit configured to measure the impedance between the electrode near the viewer's eye and the viewer's skin at the position where the electrode is placed;

a frequency analysis unit configured to analyze a frequency of the electrooculogram of the viewer obtained by the electrooculogram obtainment unit; and a measurement frequency determination unit configured to determine a frequency of a signal used for impedance measurement by the impedance measurement unit, based on the frequency of the electrooculogram of the viewer analyzed by the frequency analysis unit, wherein the impedance measurement unit is configured to measure the impedance using the signal of the frequency determined by the measurement frequency determination unit, and the impedance obtainment unit is configured to obtain the impedance measured by the impedance measurement unit.

7. The eye fatigue determination apparatus according to claim 1, further comprising:

an impedance measurement unit configured to measure the impedance between the electrode near the viewer's eye and the viewer's skin at the position where the electrode is placed; and a movement information extraction unit configured to extract movement information of an object in the video content obtained by the video content obtainment unit, wherein the measurement schedule determination unit includes:

a frequency estimation unit configured to estimate a frequency of the electrooculogram of the viewer, from the movement information of the object extracted by the movement information extraction unit; and a frequency range determination unit configured to determine a frequency range of a signal used for impedance measurement by the impedance measurement unit, based on the frequency of the electrooculogram of the viewer estimated by the frequency estimation unit, the impedance measurement unit is configured to measure the impedance using the signal of a frequency included in the frequency range determined by the frequency range determination unit, and the impedance obtainment unit is configured to obtain the impedance measured by the impedance measurement unit.

8. The eye fatigue determination apparatus according to claim 1, further comprising:

an electrooculogram measurement unit configured to measure the electrooculogram of the viewer using the electrode near the viewer's eye;

an impedance measurement unit configured to measure the impedance between the electrode near the viewer's eye and the viewer's skin at the position where the electrode is placed;

a frequency analysis unit configured to analyze a frequency of the electrooculogram of the viewer obtained by the electrooculogram obtainment unit; and a movement information extraction unit configured to extract movement information of an object in the video content obtained by the video content obtainment unit, wherein the measurement schedule determination unit includes:

a frequency estimation unit configured to estimate the frequency of the electrooculogram of the viewer, from the movement information of the object extracted by the movement information extraction unit;

a frequency range determination unit configured to determine a frequency range of a signal used for impedance measurement by the impedance measurement unit, based on the frequency of the electrooculogram of the viewer estimated by the frequency estimation unit; and a determination unit configured to change the electrooculogram measurement time section, according to a degree of agreement between the frequency range of the signal used for impedance measurement determined by the frequency range determination unit and the frequency of the electrooculogram estimated by the frequency estimation unit, the electrooculogram measurement unit is configured to measure the electrooculogram of the viewer in the electrooculogram measurement time section changed by the determination unit, the impedance measurement unit is configured to measure the impedance using the signal of a frequency included in the frequency range determined by the frequency range determination unit, the electrooculogram obtainment unit is configured to obtain the electrooculogram of the viewer measured by the electrooculogram measurement unit, and the impedance obtainment unit is configured to obtain the impedance measured by the impedance measurement unit.

9. The eye fatigue determination apparatus according to claim 8,
wherein the determination unit is configured to extend the electrooculogram measurement time section, in the case where the frequency of the electrooculogram analyzed by the frequency analysis unit is higher than the frequency range of the signal used for impedance measurement determined by the frequency range determination unit.

10. The eye fatigue determination apparatus according to claim 8,
wherein the determination unit is configured to reduce the electrooculogram measurement time section, in the case where the frequency of the electrooculogram analyzed by the frequency analysis unit is lower than the frequency range of the signal used for impedance measurement determined by the frequency range determination unit.

11. The eye fatigue determination apparatus according to claim 7,
wherein the measurement schedule determination unit further includes
a depth movement distance calculation unit configured to calculate a movement distance of the object in a depth direction, from the movement information of the object extracted by the movement information extraction unit, and
the frequency estimation unit is configured to estimate the frequency of the electrooculogram of the viewer to be higher in the case where the movement distance of the object in the depth direction between adjacent frames calculated by the depth movement distance calculation unit is longer.

12. The eye fatigue determination apparatus according to claim 1,
wherein the electrooculogram correction unit is configured to correct the electrooculogram, without using the impedance measured in a time section in which a change in impedance per unit time is greater than or equal to a predetermined value.

13. The eye fatigue determination apparatus according to claim 1,
wherein the video content is stereoscopic video content,
the electrode near the viewer's eye is included in a stereoscopic video viewing device worn by the viewer, and
the eye fatigue determination apparatus further comprises:
a defective electrode pattern obtainment unit configured to obtain defective electrode pattern information indicating correspondence between a contact state of the electrode near the viewer's eye and instruction information for a position of the viewing device worn by the viewer;
an electrode contact state determination unit configured to determine the contact state of the electrode near the viewer's eye, based on the impedance obtained by the impedance obtainment unit; and
an adjustment instruction information generation unit configured to generate instruction information by obtaining, from the defective electrode pattern information obtained by the defective electrode pattern obtainment unit, the instruction information corresponding to the contact state of the electrode determined by the electrode contact state determination unit, and present the instruction information to the viewer.

* * * * *